US010294195B2

(12) United States Patent
Funayama et al.

(10) Patent No.: US 10,294,195 B2
(45) Date of Patent: May 21, 2019

(54) DIAMINE CROSSLINKING AGENTS, CROSSLINKED ACIDIC POLYSACCHARIDES AND MEDICAL MATERIALS

(71) Applicant: Seikagaku Corporation, Tokyo (JP)

(72) Inventors: Sho Funayama, Tokyo (JP); Yosuke Yasuda, Tokyo (JP); Akihiro Takezawa, Tokyo (JP); Katsuya Takahashi, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 90 days.

(21) Appl. No.: 15/115,331

(22) PCT Filed: Jan. 30, 2015

(86) PCT No.: PCT/JP2015/052725
§ 371 (c)(1),
(2) Date: Jul. 29, 2016

(87) PCT Pub. No.: WO2015/115609
PCT Pub. Date: Aug. 6, 2015

(65) Prior Publication Data
US 2017/0001948 A1 Jan. 5, 2017

(30) Foreign Application Priority Data
Jan. 31, 2014 (JP) ................. 2014-018018

(51) Int. Cl.
| A61L 27/20 | (2006.01) |
| A61L 31/04 | (2006.01) |
| C07C 237/06 | (2006.01) |
| C08B 37/00 | (2006.01) |
| C08B 37/08 | (2006.01) |
| C07C 219/06 | (2006.01) |
| C08B 11/12 | (2006.01) |
| C07C 255/58 | (2006.01) |
| C08B 15/00 | (2006.01) |
| C08K 5/16 | (2006.01) |
| C07C 327/06 | (2006.01) |

(52) U.S. Cl.
CPC ............ *C07C 219/06* (2013.01); *A61L 27/20* (2013.01); *A61L 31/042* (2013.01); *C07C 237/06* (2013.01); *C07C 255/58* (2013.01); *C07C 327/06* (2013.01); *C08B 11/12* (2013.01); *C08B 15/005* (2013.01); *C08B 37/0069* (2013.01); *C08B 37/0072* (2013.01); *C08B 37/0084* (2013.01); *C08K 5/16* (2013.01); *C07C 2601/02* (2017.05)

(58) Field of Classification Search
CPC ... C07C 219/06; C07C 237/06; C07C 327/06; C08B 37/0069; C08B 37/0072; C08B 11/12; C08B 37/0084; A61L 31/042; A61L 27/20

USPC ...................................................... 536/3, 124
See application file for complete search history.

(56) References Cited

U.S. PATENT DOCUMENTS

| 5,466,878 | A | 11/1995 | Junin et al. |
| 5,527,893 | A * | 6/1996 | Burns ................. A61K 9/0019 |
| | | | 514/53 |
| 5,642,363 | A | 6/1997 | Smith |
| 6,229,009 | B1 | 5/2001 | Lambert et al. |
| 6,288,043 | B1 | 9/2001 | Spiro et al. |
| 6,831,172 | B1 | 12/2004 | Barbucci et al. |
| 2008/0279807 | A1 | 11/2008 | Belcheva et al. |
| 2012/0277310 | A1 | 11/2012 | Stein et al. |
| 2014/0051879 | A1 | 2/2014 | Belcheva et al. |

FOREIGN PATENT DOCUMENTS

| DE | 10307390 A1 | 9/2004 |
| EP | 341745 A1 | 11/1989 |
| EP | 2353612 A1 | 8/2011 |

(Continued)

OTHER PUBLICATIONS

Nicolaides et al. Azaserine, Synthetic Studies. II. J. Am. Chem. Soc., 76 (11):2887-2891, 1954. (Year: 1954).*
Extended European Search Report issued in corresponding European Application No. 15743701.3 dated Aug. 17, 2017 (16 pages).
Petra Eiselt et al: "Rigidity of Two-Component Hydrogels Prepared from Alginate and Poly(ethylene glycol)-Diamines", Macromolecules, vol. 32, No. 17, Aug. 1, 1999 (Aug. 1, 1999), pp. 5561-5566, XP55290730 (6 pages).

(Continued)

Primary Examiner — Yih-Horng Shiao
(74) Attorney, Agent, or Firm — Osha Liang LLP

(57) ABSTRACT

The invention provides a diamine crosslinking agent for acidic polysaccharides consisting of a diamine compound having a primary amino group at both terminals and an ester or thioester bond in the molecule, wherein the number of atom in the linear chain between at least one of the amino groups and the carbonyl carbon in the ester or thioester is 1 to 5; in particular, a diamine crosslinking agent for acidic polysaccharides which is represented by the general formula (I) below:

$$H_2N\underset{R^1\ H}{\overset{}{\diagup}}X\underset{O}{\overset{}{\diagdown}}Z\underset{}{\overset{R^2\ H}{\diagup}}NH_2 \quad (I)$$

[the symbols in the formula are as described in the specification]; a crosslinked acidic polysaccharide obtained by forming crosslinks by amide bonding between the amino groups in the diamine crosslinking agent and carboxyl groups in an acidic polysaccharide; and a medical material including the crosslinked product.

14 Claims, 4 Drawing Sheets

(56) References Cited

FOREIGN PATENT DOCUMENTS

| | | | |
|---|---|---|---|
| GB | 822908 A | 11/1959 | |
| JP | 39-18115 B1 | 8/1964 | |
| JP | 673102 A | 3/1994 | |
| JP | 2000070356 A | 3/2000 | |
| JP | 2001501228 A | 1/2001 | |
| JP | 2002529549 A | 9/2002 | |
| JP | 2002529550 A | 9/2002 | |
| JP | 2003502389 A | 1/2003 | |
| JP | 2009529068 A | 8/2009 | |
| JP | 2011505362 A | 2/2011 | |
| JP | 2013503688 A | 2/2013 | |
| JP | 2013166929 A | 8/2013 | |
| WO | 1996034618 A1 | 11/1996 | |
| WO | 98/12228 A1 | 3/1998 | |
| WO | 9844950 A1 | 10/1998 | |
| WO | 1999010385 A1 | 3/1999 | |
| WO | 1999011703 A1 | 3/1999 | |
| WO | 2000/027886 A1 | 5/2000 | |
| WO | 01057093 A1 | 8/2001 | |
| WO | 02/053526 A1 | 7/2002 | |
| WO | 0374099 A1 | 9/2003 | |
| WO | 2009/073437 A1 | 6/2009 | |
| WO | 2011/028031 A2 | 3/2011 | |

OTHER PUBLICATIONS

Kuen Yong Lee et al: "Controlling Mechanical and Swelling Properties of Alginate Hydrogels Independently by Cross-Linker Type and Cross-Linking Density", Macromolecules, vol. 33, No. 11, May 1, 2000 (May 1, 2000), pp. 4291-4294, XP55395603 (4 pages).
Petra Eiselt et al: "Proceedings Published 2000 by the American Chemical Society Controlled Mechanical Properties of Alginate Hydrogels Bycross-Linking With Poly(Ethylene Glycol)-Diamines", Polymer Reprints, vol. 41, Jan. 1, 2000 (Jan. 1, 2000), pp. 295-296, XP55395693 (2 pages).
Yujiang Fan et al: "Synthesis and Biodegradation of poly(ester amide)s containing amino acid residues: The effect of the stereoisomeric composition of L- and D-phenylalanines on the enzymatic degradation of the polymers", Journal of Polymer Science, Part A:Polymer Chemistry, vol. 40, No. 3, Jan. 3, 2002 (Jan. 3, 2002), pp. 385-392, XP55395412 (8 pages).
Yujiang Fan et al: "Synthesis and specific biodegradation of novel polyesteramides containing amino acid residues", Journal of Polymer Science, Part A:Polymer Chemistry, vol. 39, No. 9, May 1, 2001 (May 1, 2001), pp. 1318-1328, XP55395442 (11 pages).
Database CA [Online] Chemical Abstracts Service, Columbus, Ohio, US; Nagawa, Masatoshi et al: "Novel peptides", XP002772784 (2 pages), Accessed on Mar. 8, 2017.
S. Sakakibara et al: "An Approach to the Specific Cleavage of Peptide Bonds. I. The Acyl Migration in Dipeptides Containing Hydroxyaamino Acids in Anhydrous Hydrogen Fluoride", Journal of the American Chemical Society, vol. 84, No. 24, Dec. 1, 1962 (Dec. 1, 1962), pp. 4921-4928, XP55396194 (8 pages).
E.Sondheimer, A New Synthesis of a-L-Aspartyl-L-leucine, Journal of Organic Chemistry, 1965, Vol.30, No. 2, 665-666.
E.D.Nicolaides, R.D.Westland and E.L.Wittle, Azaserine, Synthetic Studies. 11, Journal of the American Chemical Society, 1954, vol. 76, 2887-2891.
Jason A. Burdick et al. "Hyaluronic Acid Hydrogels for Biomedical Applications" Adv. Mater., 2011, 23 (12), H41-56.
Amnon Sintov et al. "Cross-linked chondroitin sulphate: characterization for drug delivery purposes" Biomaterials, 1995, vol.16, p. 473-478.
C. Bourie et al. "Insolubilization Test of Sodium chondroitin Sulphate with a view to Its Use as Colonic Carrier of Drugs" Journal of Biomater. appl., 1998, 12, 201-221.
Jack E. Baldwin "Rules for Ring Closure" Journal of Chem. Soc., Chem. Commun. 1976, 734-736.
Jack E. Baldwin et al. "Rules for Ring closure: Ring Formation by Conjugate Addition of Oxygen Nucleophiles" Journal of Org. Chem., 1977, 42 (24), 3846-3852.
Natalia N. et al. "Switch Peptide via Staudinger Reaction" Org. Lett., 2008, 10 (22), 5243-5246.
Irene Coin et al. "Depsipeptide Methodology for Solid-Phase Peptide Synthesis: Circumvention Side Reactions and Development of an Automated Technique via Depsidipeptide Units" Journal of Org. Chem. 2006, 71, 6171-6177.
Dawson P.E. et al. "Synthesis of Proteins by Native Chemical Ligation" Science, 1994, 266 (5186), 776-779.
International Search Report issued in corresponding International Application No. PCT/JP2015/052725 dated Feb. 24, 2015 (5 pages).
Office Action issued in corresponding European Application No. 15743701.3 dated Aug. 23, 2018 (9 pages).

\* cited by examiner

DIAMINE CROSSLINKING AGENTS, CROSSLINKED ACIDIC POLYSACCHARIDES AND MEDICAL MATERIALS

TECHNICAL FIELD

The present invention relates to diamine crosslinking agents having a biodegradable site, crosslinked acidic polysaccharides obtained by direct condensation of the crosslinking agents and carboxyl groups in acidic polysaccharides, and medical uses of the crosslinked products.

BACKGROUND ART

Crosslinked polysaccharides obtained by covalent bonding of polysaccharide molecules are promising medical materials because of the high biocompatibility of polysaccharides per se and have been subjects of interest in various researches.

As the crosslinking methods, for example, the following four categories can be cited.

(1) Crosslinking with aldehyde crosslinking agents such as formaldehyde or glutaraldehyde.

(2) Self-crosslinking without any crosslinking groups which occurs between carboxyl groups and hydroxyl groups both present in the polysaccharides.

(3) Crosslinking with homo bifunctional crosslinking agents such as diepoxides, divinyl sulfones, diamines and dihydrazides, or hetero bifunctional crosslinking agents such as epihalohydrins.

(4) Crosslinking by the reaction of polysaccharides having functional groups such as photoreactive groups, polymerizable functional groups, amino groups, thiol groups and halogens, with polysaccharides having reactive groups which are complementary to the above functional groups.

Those methods in Category (1) have a safety problem. For example, Japanese Patent Kohyo Publication No. 2013-503688 describes that formalin or glutaraldehyde used as the crosslinking agent undergoes the crosslinking reaction also with proteins in a living body to give rise to tissue toxicity.

Regarding the self-crosslinking of Category (2), for example, take hyaluronic acid (HA) for instance, self-crosslinked ester-bonded hyaluronic acid wherein a portion or all of the carboxyl groups in a molecule are esterified with alcohol groups of the same polysaccharide molecule or of different polysaccharide molecules is disclosed in EP Patent No. 341745. Further, WO 99/10385 discloses self-crosslinked ester-bonded hyaluronic acid prepared by at least once freezing and subsequently thawing an aqueous hyaluronic acid solution under acidic conditions. WO 01/57093 discloses self-crosslinked ester-bonded hyaluronic acid prepared by mixing hyaluronic acid with an acidic solution so that the concentration will be not less than 5% and keeping the mixture as such without freezing the mixture. In methods in which an aqueous hyaluronic acid solution is frozen under acidic conditions, the dissolution half-life is increased as the freezing time is longer but excessively long freezing causes the molecular weight of the hyaluronic acid to be decreased, resulting in a shortening of the dissolution half-life. Further, the fact that the self-crosslinking occurs without any crosslinking agents makes it impossible to control the disintegration time by selecting an appropriate chemical structure of the crosslinking agent.

Regarding Category (3), Japanese Patent Kohyo Publication No. 2011-505362 discloses crosslinked products of hyaluronic acid or chondroitin sulfate (CS) obtained with diepoxide crosslinking agents such as 1,4-butanediol diglycidyl ether (BDDE).

Regarding Category (4), Adv. Mater., 2011, 23 (12), 1141-56 (Jason A. Burdick et al.) discloses the introduction of dihydrazide adipate, tyramide, methacrylate, glycidyl methacrylate, thiopropionyl hydrazide, bromoacetate and the like with respect to carboxyl groups and hydroxyl groups of hyaluronic acid.

As the example which aims at efficient modification of the physical properties of polysaccharides, a method to crosslink carboxyl groups of polysaccharides by diamines (corresponding to Category (3)) can be cited. For example, Japanese Patent Application Kokai Publication No. 2000-70356 discloses crosslinked products obtained by reacting carboxyl groups of polysaccharides such as alginic acid (Alg) and hyaluronic acid with alkyldiamines such as ethylenediamine. Further, Japanese Patent Kohyo Publication No. 2002-529549 discloses carboxymethyl cellulose (CMC) crosslinked with 1,3-diaminopropane. A report describes that chondroitin sulfate derivatives have been produced with use of diamines as the crosslinking agents (Biomaterials, 1995, 16, 473-478 (Amnon Sintov et al.)). However, various analyses of products prepared by reproducing the reported production method did not confirm the crosslinking of chondroitin sulfate (J. Biomater. appl., 1998, 12, 201-221 (C. Bourie et al.)) and concluded that the production of crosslinked chondroitin sulfate was unreal.

Some reports describe that esters are selected as biodegradable sites that allow crosslinked acidic polysaccharides to be disintegrated. For example, Adv. Mater., 2011, 23 (12), H41-56 (Jason A. Burdick et al.) reports that hyaluronic acid is crosslinked by the introduction of tyramide or glycidyl methacrylate followed by radical reaction or polymerization reaction. Further, Japanese Patent Application Kokai Publication No. H6-73102 presents a report in which a photosensitive compound is ester bonded to carboxyl groups in hyaluronic acid or chondroitin sulfate and the polysaccharide is photocrosslinked. These reports are associated with crosslinked products obtained by two-step reaction including the introduction of reactive groups and the crosslinking reaction.

2-Aminoethyl-2-aminoacetate (GlyC2N), illustrated in the right box below, is an example of the simplest structures of diamine crosslinking agents having a biodegradable site. According to Baldwin's rules (empirical rules describing the relative favourability of intramolecular nucleophilic reactions) (J. Chem. Soc., Chem. Commun. 1976, 734-736. (Jack E. Baldwin), J. Org. Chem., 1977, 42 (24), 3846-3852. (Jack E. Baldwin et al.)), the carbonyl group (an electrophilic group) in the ester bond and the amino group (a nucleophilic group) can form a 5-membered ring (5-exo-trig type). It is therefore understood that intramolecular nucleophilic substitution reaction is likely to occur in structures analogous to the above diamine (see below). In general, it is known that relatively simple exo-trig structures form a 3- to 7-membered ring in the transition state.

[Chem. 1]

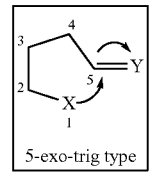

5-exo-trig type

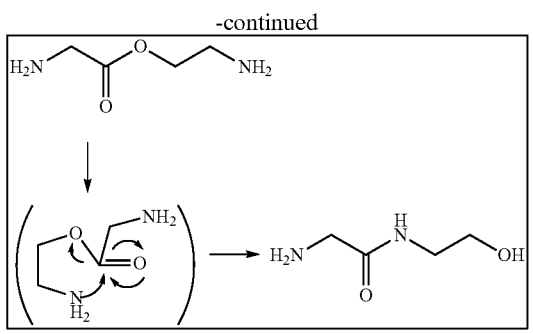

The left box above illustrates an example of Baldwin's rules. The right box illustrates the O→N acyl rearrangement of GlyC2N.

As a specific example of the relative favourability of intramolecular reactions, the similar structure -α-amino acid-(ester bond)-serine or threonine- is readily converted into -α-amino acid-(amide bond)-serine or threonine- by intramolecular nucleophilic reaction of the free amino group in serine to the carbonyl carbon in the ester bond (O→N acyl rearrangement), in water and under physiological conditions (Org. Lett., 2008, 10 (22), 5243-5246 (Natalia N. et al.), J. Org. Chem. 2006, 71, 6171-6177 (Irene Coin et al.)). S→N acyl rearrangement is also used in similar reactions (Science, 1994, 266 (5186), 776-779 (Dawson P. E. et al.)). These structures are generally called switch peptides or native chemical ligations and are frequently used as techniques for the chemical synthesis or structural conversion of peptides.

Based on the facts described above, it is conceivable that diamine crosslinking agents having a biodegradable site will easily undergo intramolecular nucleophilic substitution reactions, and actually there have been no reports describing that they are used as crosslinking agents for acidic polysaccharides.

Reports do exist which describe that compounds having the above diamine structure in part of the molecule are used for crosslinking reactions. For example, WO 96/34618 discloses a method in which 2-aminoethyl-2-aminoacetate and hexamethylene dicyanate are mixed with each other to form a polyfunctional crosslinking agent and proteins having amino groups are crosslinked therewith. Another example is reported in WO 99/11703 in which alginic acid, polyglutamic acid or carboxymethyl cellulose is crosslinked with a dihydrazide or a dicarboxylic acid wherein a 2-aminoglycinate skeleton is present in the dihydrazide skeleton or the dicarboxylic acid skeleton.

Even in these reports, the use of a crosslinker having such a structure as GlyC2N in the molecule involves the conversion of the amino structures at both ends into two carboxyl groups or two hydrazide groups to inhibit intramolecular reaction. That is, the crosslinking agents do not directly have a diamine structure with a biodegradable site in the molecule.

In spite of a variety of studies carried out on the crosslinking agents for acidic polysaccharides, there have been no reports of diamine crosslinking agents which, without combination with other kinds of molecules, allow for easy and simultaneous control of physical stress and disintegration time in accordance with use applications of medical materials while ensuring the high biocompatibility of acidic polysaccharides.

CITATION LIST

Patent Literature

Patent Literature 1: Japanese Patent Kohyo Publication No. 2013-503688
Patent Literature 2: EP Patent No. 341745
Patent Literature 3: WO 99/10385
Patent Literature 4: WO 01/57093
Patent Literature 5: Japanese Patent Kohyo Publication No. 2011-505362
Patent Literature 6: Japanese Patent Application Kokai Publication No. 2000-70356
Patent Literature 7: Japanese Patent Kohyo Publication No. 2002-529549
Patent Literature 8: Japanese Patent Application Kokai Publication No. H6-73102
Patent Literature 9: WO 96/34618
Patent Literature 10: WO 99/11703

Non Patent Literature

Non Patent Literature 1: Adv. Mater., 2011, 23 (12), H41-56 (Jason A. Burdick et al.)
Non Patent Literature 2: Biomaterials, 1995, 16, 473-478 (Amnon Sintov et al.)
Non Patent Literature 3: J. Biomater. appl., 1998, 12, 201-221 (C. Bourie et al.)
Non Patent Literature 4: J. Chem. Soc., Chem. Commun. 1976, 734-736. (Jack E. Baldwin)
Non Patent Literature 5: J. Org. Chem., 1977, 42 (24), 3846-3852. (Jack E. Baldwin et al.)
Non Patent Literature 6: Org. Lett., 2008, 10 (22), 5243-5246 (Natalia N. et al.)
Non Patent Literature 7: J. Org. Chem. 2006, 71, 6171-6177 (Irene Coin et al.)
Non Patent Literature 8: Science, 1994, 266 (5186), 776-779 (Dawson P. E. et al.)

DISCLOSURE OF INVENTION

Technical Problem

Sugar chain crosslinking methods have been studied vigorously as described above. In methods of Category (3), the fact that diepoxide crosslinking agents can dramatically alter properties of various polysaccharides have been reported, but control of disintegration time simultaneously with attaining such properties alteration is still incapable. Alkyldiamine crosslinking agents have no biodegradable sites, and this structural fact makes it impossible to control the disintegration time determined by the decomposition of the crosslinking agents. Those methods in Category (4) are complicated due to the need of two-step reaction including the introduction of reactive groups and the crosslinking reaction. Thus, no ideal crosslinking agents have been realized which satisfy all of safety, easy preparation, efficient physical properties alteration and disintegration properties. In particular, it can be said that great difficulties are involved in developing crosslinking agents which can efficiently modify physical properties and provide satisfactory disintegration properties at the same time.

When medical materials which include crosslinked polysaccharides are used as, for example, tissue bulking materials or adhesion preventing materials, the crosslinked polysaccharides are demanded to have high biocompatibility as a matter of course and are also particularly demanded to exhibit physical stress for separating tissues from each other (barrier performance) after administration in conjunction with quick disintegration performance after the lapse of a prescribed period. Crosslinked polysaccharides used as adhesion preventing materials have a challenge in which increasing the physical stress makes the materials persistent while quick disintegration comes with insufficient physical stress. Because these phenomena are a trade-off, the challenge is at a very high level of difficulty and there has been no realization of adhesion preventing materials which include crosslinked polysaccharides having the above two performances.

No diamine crosslinking agents are known which, without combination with other kinds of molecules, allow for easy and simultaneous control of physical stress and disintegration time in accordance with use applications of medical materials while ensuring the high biocompatibility of acidic polysaccharides.

Objects of the invention are therefore to provide highly practical diamine crosslinking agents which can crosslink acidic polysaccharides by direct condensation reaction with carboxyl groups in the acidic polysaccharides so as to give crosslinked products having appropriate physical stress and quick disintegration properties after the lapse of a prescribed period, and to provide crosslinked acidic polysaccharides as medical materials which are produced with the crosslinking agents.

Solution to Problem

In light of the above objects, the inventors carried out extensive studies in order to develop diamine crosslinking agents capable of affording crosslinked acidic polysaccharides having appropriate physical stress and appropriate disintegration properties after the lapse of a prescribed period in accordance with use applications of medical materials.

As a result, the inventors have found that a diamine crosslinking agent which has specific substituents mainly derived from an amino acid or a derivative thereof and an aminoalcohol or a derivative thereof and which has at least one biodegradable site can crosslink, without combination with other kinds of molecules, an acidic polysaccharide to give a crosslinked acidic polysaccharide while allowing for easy and simultaneous control of the physical stress and the disintegration time of the crosslinked product. The present invention has been completed based on the finding.

Specifically, the present invention pertains to the following aspects.

(1) A diamine crosslinking agent for acidic polysaccharides consisting of diamine compounds having a primary amino group at both terminals and an ester or thioester bond in the molecule, wherein the number of atom in the linear chain between at least one of the amino groups and the carbonyl carbon in the ester or thioester is 1 to 5.

(2) A diamine crosslinking agent for acidic polysaccharides represented by the general formula (I) below:

[Chem. 2]

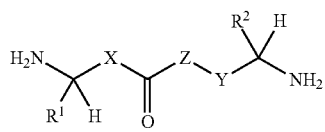

(I)

[wherein the number of atoms in the linear chain between the primary amino groups at both terminals is 5 to 12, X and Y are each independently a single bond, a substituted or unsubstituted alkylene group, a substituted or unsubstituted alkenylene group, or a substituted or unsubstituted alkynylene group, with the proviso that X and Y cannot be single bonds at the same time;

Z represents an oxygen atom or a sulfur atom;

$R^1$ and $R^2$ are each independently a hydrogen atom, a —$CONR^3R^4$ group, a —$COOR^5$ group, a substituted or unsubstituted alkyl group, a substituted or unsubstituted alkenyl group, or a substituted or unsubstituted alkynyl group;

any —$CH_2$— in alkylene group, alkenylene group or alkynylene group represented by X or Y may be substituted with one or more groups selected from the group consisting of amide group (—CONH—), ester group (—C(=O)—O—), ether group (—O—), imino group (—NH—) and phenylene group wherein any ester group, amide group, ether group (—O—) and imino group (—NH—) present in X or Y cannot be directly adjacent to —CO—Z— in the formula (I), any —$CH_2$— in alkyl group, alkenyl group or alkynyl group represented by $R^1$ or $R^2$ may be substituted with one or more groups selected from the group consisting of >C=O, —CONH—, arylene, —O—, —$NR^6$— and —S—;

the substituents in X, Y, $R^1$ and $R^2$ are selected from the group consisting of hydroxyl groups, alkyl groups having 1 to 6 carbon atom, phenyl groups, indolyl groups, diazolyl groups, —$(CH_2)_n$—NHMe groups, —$(CH_2)_n$—$NMe_2$ groups, —$(CH_2)_n$—$CONR^3R^4$ groups, —$(CH_2)_n$—$COOR^5$ groups, —SMe groups and —SH groups, and the substituents in X and Y may be selected from the group consisting of 4-hydroxyphenyl groups, halogen atoms, nitro groups and nitrile groups, wherein n independently at each occurrence represents an integer of 0 to 4; and $R^3$, $R^4$, $R^5$ and $R^6$ are each independently a hydrogen atom or an alkyl group optionally substituted with phenyl group].

(3) The diamine crosslinking agent according to (2), wherein Z is an oxygen atom.

(4) The diamine crosslinking agent according to (3), wherein the number of atoms in the linear chain between the amino groups at both terminals is 5 to 8.

(5) The diamine crosslinking agent according to (3), wherein the number of atoms in the linear chain between the amino groups at both terminals is 5 or 6.

(6) The diamine crosslinking agent according to any one of (2) to (5), wherein $R^1$ is a hydrogen atom, or a substituted or unsubstituted alkyl group;

$R^2$ is a hydrogen atom, a —$CONR^3R^4$ group or a —$COOR^5$ group;

X is a single bond or an alkylene group which may be substituted by halogen;

Y is a substituted or unsubstituted alkylene group;

the substituent(s) in $R^1$ is selected from the group consisting of methyl groups, phenyl groups, indolyl groups, —$COOR^5$ groups and —S—Me groups; and the substituent(s) in Y is selected from the group consisting of methyl groups, phenyl groups and —$COOR^5$ groups.

(7) The diamine crosslinking agent according to any one of (2) to (5), wherein

X is a single bond; Y is a >$CR^7R^8$ group; and $R^7$ and $R^8$ are each independently a hydrogen atom, a hydroxyl group, an alkyl group having 1 to 6 carbon atom, a phenyl group, a 4-hydroxyphenyl group, an indolyl group, a diazolyl group, a —(CH$_2$)$_n$—NHMe group, a —(CH$_2$)$_n$—NMe$_2$ group, a —(CH$_2$)$_n$—CONR$_3$R$_4$ group, a —(CH$_2$)$_n$—COOR$^5$ group, a —SH group, a halogen atom, a nitro group or a nitrile group.

(8) The diamine crosslinking agent according to (7), wherein
R$^2$ is a —CONR$^3$R$^4$ group or a —COOR$^5$ group;
R$^7$ is a hydrogen atom; and
R$^8$ is a hydrogen atom or a methyl group.

(9) The diamine crosslinking agent according to (4) or (5), wherein at least one of X and Y is substituted with a phenyl group, a 4-hydroxyphenyl group, a —CONR$^3$R$^4$ group, a —COOR$^5$ group, a halogen atom, a nitro group or a nitrile group.

(10) The diamine crosslinking agent according to (7), wherein R$^7$ and R$^8$ are each independently a hydrogen atom, a phenyl group, a 4-hydroxyphenyl group, a —CONR$^3$R$^4$ group, a —COOR$^5$ group, a halogen atom, a nitro group or a nitrile group.

(11) The diamine crosslinking agent according to (10), wherein R$^1$ is a hydrogen atom, a —(CH$_2$)$_2$—S—CH$_3$ group, a —(CH$_2$)$_{3\ or\ 4}$—NHMe group, a —(CH$_2$)$_{3\ or\ 4}$—NMe$_2$ group or a —(CH$_2$)$_{1\ or\ 2}$—COOR$^5$ group.

(12) The diamine crosslinking agent according to (11), wherein R$^2$ is a —CONR$^3$R$^4$ group or a —COOR$^5$ group, and R$^7$ and R$^8$ are hydrogen atoms.

(13) The diamine crosslinking agent according to (12), wherein R$^1$ is a hydrogen atom.

(14) A crosslinked acidic polysaccharide obtained by forming crosslinks by amide bonding between the primary amino groups in the diamine crosslinking agent according to any one of (1) to (13) and carboxyl groups in an acidic polysaccharide.

(15) A crosslinked acidic polysaccharide obtained by forming crosslinks by amide bonding between the primary amino groups in the diamine crosslinking agent according to any one of (9) to (13) and carboxyl groups in an acidic polysaccharide.

(16) The crosslinked acidic polysaccharide according to (14) or (15), wherein the acidic polysaccharide is glycosaminoglycan, carboxymethyl cellulose or alginic acid.

(17) The crosslinked acidic polysaccharide according to (16), wherein the acidic polysaccharide is glycosaminoglycan.

(18) The crosslinked acidic polysaccharide according to (17), wherein the glycosaminoglycan is chondroitin or chondroitin sulfate.

(19) The crosslinked acidic polysaccharide according to (15), wherein the acidic polysaccharide is glycosaminoglycan, carboxymethyl cellulose or alginic acid.

(20) The crosslinked acidic polysaccharide according to (19), wherein the acidic polysaccharide is glycosaminoglycan.

(21) The crosslinked acidic polysaccharide according to (20), wherein the glycosaminoglycan is chondroitin or chondroitin sulfate.

(22) A medical material comprising the crosslinked acidic polysaccharide according to any one of (14) to (21).

(23) A tissue bulking material comprising the crosslinked acidic polysaccharide according to any one of (14) to (21).

(24) An adhesion preventing material comprising the crosslinked acidic polysaccharide according to any one of (15) and (19) to (21).

(25) A compound represented by the general formula (II) below:

[Chem. 3]

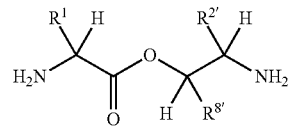

(II)

[wherein
R$^1$ is a hydrogen atom, a —CONR$^3$R$^4$ group, a —COOR$^5$ group, a substituted or unsubstituted alkyl group, a substituted or unsubstituted alkenyl group, or a substituted or unsubstituted alkynyl group;
R$^{2'}$ is a —CONR$^3$R$^4$ group or a —COOR$^5$ group;
any —CH$_2$— in alkyl group, alkenyl group or alkynyl group represented by R$^1$ may be substituted with one or more groups selected from the group consisting of >C=O, —CONH—, an arylene, —O—, —NR$^6$— and —S— (with the proviso that when R$^5$ is a benzyl group, —O— is excluded);
the substituent(s) in R$^1$ is selected from the group consisting of hydroxyl groups, alkyl groups having 1 to 6 carbon atom, indolyl groups, diazolyl groups, —(CH$_2$)$_n$—NHMe groups, —(CH$_2$)$_n$—NMe$_2$ groups, —(CH$_2$)$_n$—CONR$^3$R$^4$ groups, —(CH$_2$)$_n$—COOR$^5$ groups and —SH groups (with the proviso that when R$^{2'}$ is a —CONH$_2$ group, —SH group is excluded) wherein n independently at each occurrence represents an integer of 0 to 4;
R$^3$, R$^4$, R$^5$ and R$^6$ are each independently a hydrogen atom or an alkyl group optionally substituted with phenyl group; and
R$^{8'}$ is a hydrogen atom or a methyl group].

(26) A crosslinked acidic polysaccharide obtained by forming crosslinks by amide bonding between the primary amino groups in the compound according to (25) and carboxyl groups in an acidic polysaccharide.

Advantageous Effects of Invention

The diamine crosslinking agents of the present invention can confer appropriate physical stress and disintegration properties to acidic polysaccharides. Thus, crosslinked acidic polysaccharides obtained by crosslinking an acidic polysaccharide with the crosslinking agent exhibit appropriate physical stress and quick disintegration properties after the lapse of a prescribed period, thereby attaining high practical utility. Further, the crosslinked products have a distinct structure, and are useful as medical materials represented by adhesion preventing materials and tissue bulking materials.

MODE FOR CARRYING OUT THE INVENTION

Figure 1:
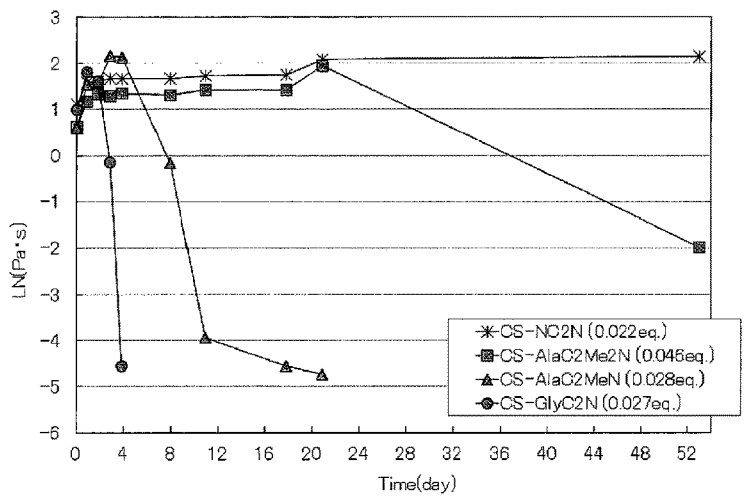
FIG. 1 is a diagram illustrating changes in the viscosity of swollen crosslinked CS materials (CS-GlyC2N/AlaC2MeN/AlaC2Me2N/NC2N) with time.

In the specification, the term alkyl group refers to a monovalent, linear, saturated and aliphatic hydrocarbon group having 1 to 12 carbon atoms, or preferably 1 to 8 carbon atoms, or a monovalent, branched or cyclic, saturated and aliphatic hydrocarbon group having 3 to 12 carbon atoms, or preferably 3 to 8 carbon atoms. The term alkylene group refers to a divalent, linear, saturated and aliphatic hydrocarbon group having 1 to 12 carbon atoms, or preferably 1 to 8 carbon atoms, or a divalent, branched or cyclic, saturated and aliphatic hydrocarbon group having 3 to 12 carbon atoms, or preferably 3 to 8 carbon atoms.

The term alkenyl group refers to a monovalent, linear and aliphatic hydrocarbon group with 2 to 12 carbon atoms, or preferably 2 to 8 carbon atoms having at least one double bond, or a monovalent, branched and aliphatic hydrocarbon group with 3 to 12 carbon atoms, or preferably 3 to 8 carbon atoms having at least one double bond. The term alkenylene group refers to a divalent, linear and aliphatic hydrocarbon group with 2 to 12 carbon atoms, or preferably 2 to 8 carbon atoms having at least one double bond, or a divalent, branched and aliphatic hydrocarbon group having 3 to 12 carbon atoms, or preferably 3 to 8 carbon atoms having at least one double bond.

The term alkynyl group refers to a monovalent, linear and aliphatic hydrocarbon group with 2 to 12 carbon atoms, or preferably 2 to 8 carbon atoms having at least one triple bond, or a monovalent, branched and aliphatic hydrocarbon group with 3 to 12 carbon atoms, or preferably 3 to 8 carbon atoms having at least one triple bond. The term alkynylene group refers to a divalent, linear and aliphatic hydrocarbon group with 2 to 12 carbon atoms, or preferably 2 to 8 carbon atoms having at least one triple bond, or a divalent, branched and aliphatic hydrocarbon group having 3 to 12 carbon atoms, or preferably 3 to 8 carbon atoms having at least one triple bond.

The term arylene group refers to a divalent, monocyclic or polycyclic, and aromatic hydrocarbon group which has 6 to 20 carbon atoms constituting the ring. Specific examples include phenylene (1,2-, 1,3- or 1,4-phenylene) and naphthylene.

In the specification, the numerical ranges indicated with "to" include the values before and after the "to" as the minimum and the maximum. In the case where a plurality of substances belonging to a single kind of a component are present in a composition, the total content of such substances present in the composition is indicated as the content of that component in the composition unless otherwise mentioned.

The style used in the specification to describe crosslinked acidic polysaccharides is (type of acidic polysaccharide)-(type of diamine crosslinking agent). The codes in parenthesis following the names of compounds are used as the abbreviations of the diamine crosslinking agents.

As an example, crosslinked chondroitin sulfate obtained by crosslinking chondroitin sulfate sodium with 2-aminoethyl-2-aminoacetate (GlyC2N).dihydrochloride as the diamine crosslinking agent is represented as CS-GlyC2N.

Hereinafter, the present invention will be described in detail based on embodiments of the invention.

Acidic Polysaccharides

Acidic polysaccharides are polysaccharides having carboxyl groups. Examples include hyaluronic acid, chondroitin, chondroitin sulfate, dermatan sulfate, carboxymethyl cellulose, carboxyethyl cellulose, carboxymethyl dextran, carboxyethyl dextran, carboxymethyl pullulan, carboxyethyl pullulan, carboxymethyl amylose, carboxyethyl amylose, oxidized cellulose and alginic acid etc. Of these, at least one selected from the group consisting of hyaluronic acid, chondroitin sulfate, chondroitin, carboxymethyl cellulose and alginic acid is preferable, and at least one selected from the group consisting of chondroitin sulfate and chondroitin is more preferable. The carboxyl groups and the sulfate groups in the acidic polysaccharides may be in the form of free acid without forming a salt, or may be in the form of pharmaceutically acceptable salt.

Examples of the pharmaceutically acceptable salts include salts with alkali metal ions such as sodium salts and potassium salts; and salts with alkaline earth metal ions such as magnesium salts and calcium salts. From the points of view of biological applicability and affinity, the acidic polysaccharide derivatives are preferably pharmaceutically acceptable salts with alkali metal ions, and more preferably sodium salts.

The acidic polysaccharides may be obtained from natural sources or produced by known methods depending on the types thereof.

The molecular weight of the acidic polysaccharides is not particularly limited and may be selected appropriately in accordance with factors such as the types of monosaccharides forming the acidic polysaccharides, and purposes. The weight average molecular weight of the acidic polysaccharides may be, for example, 10,000 to 5,000,000, preferably 15,000 to 2,000,000, and more preferably 15,000 to 1,000,000. The desired acidic polysaccharide may be selected using a viscosity of a solution thereof as the index instead of the molecular weight.

When hyaluronic acid is selected as the acidic polysaccharide, the weight average molecular weight thereof is not particularly limited and may be selected appropriately in accordance with purposes (such as, for example, use applications as medical materials). The weight average molecular weight may be, for example, 10,000 to 5,000,000, and, from the point of view of production efficiency, is preferably 50,000 to 3,000,000, and more preferably 200,000 to 1,000,000.

When chondroitin sulfate is used as the acidic polysaccharide, the type thereof is not particularly limited and the chondroitin sulfate may be any of chondroitin sulfate A, chondroitin sulfate B, chondroitin sulfate C, chondroitin sulfate D, chondroitin sulfate E and the like. The type of the chondroitin sulfate may be selected appropriately in accordance with purposes (such as, for example, use applications as medical materials). The weight average molecular weight of the chondroitin sulfate is not particularly limited and may be selected appropriately in accordance with factors such as purposes. The weight average molecular weight is preferably 10,000 to 100,000, and more preferably 10,000 to 50,000.

When carboxymethyl cellulose or carboxyethyl cellulose is used as the acidic polysaccharide, the viscosity (the molecular weight) and the etherification degree (the degree of substitution) are not particularly limited and may be selected appropriately in accordance with purposes (such as, for example, use applications as medical materials). When the carboxyl groups are in the form of sodium salt, it is preferable that the etherification degree be 0.5 to 1.3 and the viscosity of a 1 mass % aqueous solution be 10 to 18,000 (mPa·s), and it is more preferable that the etherification degree be 0.5 to 1.0 and the viscosity of a 1 mass % aqueous solution be 50 to 6,000 (mPa·s). The viscosity may be measured with a Brookfield rotary viscometer at 25° C.

When alginic acid is used as the acidic polysaccharide, the viscosity (the molecular weight) is not particularly limited and may be selected appropriately in accordance with purposes (such as, for example, use applications as medical materials). When the carboxyl groups are in the form of sodium salt, it is preferable that the viscosity of a 1 mass % aqueous solution be 10 to 1,000 (mPa·s), and more preferably 80 to 600 (mPa·s). The viscosity may be measured with a Brookfield rotary viscometer at 25° C.

Diamine Crosslinking Agents

The diamine crosslinking agent is a diamine crosslinking agent for acidic polysaccharides consisting of a diamine compound having a primary amino group at both ends and an ester or thioester bond in the molecule. In the diamine compound, at least one of the amino groups and the carbonyl carbon in the ester or thioester are interrupted by a linear chain having 1 to 5 atoms. Here, the "linear chain" which interrupts the two points in the compound indicates a structure which connects the two with the least number of atoms.

In such diamine compounds and, for example, those structures which are terminated with a primary amino group at both ends and have the carbonyl carbon described above on a linear chain connecting the two terminal amino groups, the transition state tends to take a 3- to 7-exo-trig ring according to the aforementioned empirical rules when the number of atoms forming the linear chain between the two terminal amino groups is 5 to 12.

Diamine compounds having a structure which causes the compounds to tend to take such a transition state have been considered as being not usable to effect crosslinking. However, the inventors have found for the first time that even such compounds can be used for the crosslinking of acidic polysaccharides.

An example of the above compounds is a diamine crosslinking agent represented by the general formula (I) below:

[Chem. 4]

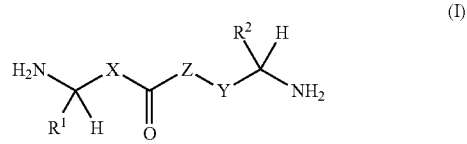

(I)

[wherein the number of atoms in the linear chain between the amino groups at both terminals is 5 to 12, X and Y are each independently a single bond, a substituted or unsubstituted alkylene group, a substituted or unsubstituted alkenylene group, or a substituted or unsubstituted alkynylene group, with the proviso that X and Y cannot be single bonds at the same time;

Z represents an oxygen atom or a sulfur atom;

$R^1$ and $R^2$ are each independently a hydrogen atom, a —$CONR^3R^4$ group, a —$COOR^5$ group, a substituted or unsubstituted alkyl group, a substituted or unsubstituted alkenyl group, or a substituted or unsubstituted alkynyl group;

any —$CH_2$— in alkylene group, alkenylene group or alkynylene group represented by X or Y may be substituted with one or more groups selected from the group consisting of amide group (—CONH—), ester group —C(=O)—O—), ether group (—O—), imino group (—NH—) and phenylene group, wherein any ester group, amide group, ether group (—O—) and imino group (—NH—) present in X or Y cannot be directly adjacent to —CO—Z— in the formula (I), any —$CH_2$— in alkyl group, alkenyl group or alkynyl group represented by $R^1$ or $R^2$ may be substituted with one or more groups selected from the group consisting of >C=O, —CONH—, arylene, —O—, —$NR^6$— and —S—;

the substituents in X, Y, $R^1$ and $R^2$ are selected from the group consisting of hydroxyl groups, alkyl groups having 1 to 6 carbon atom, phenyl groups, indolyl groups, diazolyl groups, —$(CH_2)_n$—NHMe groups, —$(CH_2)_n$—$NMe_2$ groups, —$(CH_2)_n$—$CONR^3R^4$ groups, —$(CH_2)_n$—$COOR^5$ groups, —SMe groups and —SH groups, and the substituents in X and Y may be selected from the group consisting of 4-hydroxyphenyl groups, halogen atoms, nitro groups and nitrile groups, wherein n independently at each occurrence represents an integer of 0 to 4; and $R^3$, $R^4$, $R^5$ and $R^6$ are each independently a hydrogen atom or an alkyl group optionally substituted with phenyl group].

In the diamine crosslinking agents, it is preferable that the structure of the diamine crosslinking agent have at least one bond that can be decomposed in a living body, namely, biodegradable site, on the linear chain between the two terminal amino groups. As the decomposable bonds, among others, ester bonds and thioester bonds are preferable, and ester bonds are more preferable. In the specification, the term biodegradable site means a structure corresponding to —C(=O)—Z— in the formula (I), and indicates an ester bond or a thioester bond unless otherwise mentioned. The number of the biodegradable sites is preferably 1 or 2, and more preferably 1.

The disintegration time of crosslinked acidic polysaccharides may be easily controlled by selecting the types and numbers of substituents on the groups X and Y near the biodegradable site (the ester bond or the thioester bond) in the diamine crosslinking agent, and the types of the groups $R^1$ and $R^2$. That is, the disintegration rate of crosslinked acidic polysaccharides in living bodies can be controlled irrespective of the types of acidic polysaccharides.

The position of the diamine crosslinking agent represented by the general formula (I) may be any positions in the groups X and Y as long as they can affect the stability of the biodegradable site, and specifically, at least one may be preferably selected from the group consisting of α-position, β-position and γ-position relative to the biodegradable site. In the case where X or Y is a single bond, the control of the disintegration time of crosslinked acidic polysaccharides in living bodies is feasible by manipulating the structures of $R^1$ and $R^2$ which can bear substituents. The number of the substituents may be selected in accordance with purposes and is, for example, preferably 0 to 8, and more preferably 1 to 4.

For example, the type of the substituents is preferably at least one selected from the group consisting of electron-withdrawing groups, electron-donating groups and steric hindrance groups.

When, for example, the substituents introduced in the groups X and Y, and $R^1$ and $R^2$ are electron-withdrawing groups, the biodegradable sites are more prone to decomposition and the disintegration time of crosslinked acidic polysaccharides tends to be decreased as compared to when no substituents are present. Thus, the disintegration time of crosslinked acidic polysaccharides may be controlled easily to fall into the desired range by selecting the electron-withdrawing groups while using the strength of electron-withdrawing groups such as, for example, electronegativity and Hammett constants as indicators. In detail, the disintegration time of crosslinked acidic polysaccharides in living bodies tends to be reduced when strong electron-withdrawing groups are selected. Specifically, the introduction of halogen atoms such as fluorine, chlorine and bromine tends to reduce the disintegration time of acidic polysaccharides in living bodies in the order of increasing electronegativity (F>Cl>Br).

The electron-withdrawing groups are not particularly limited as long as they can be introduced into the groups X and Y and also $R^1$ and $R^2$, and may be selected appropriately from those electron-withdrawing groups that are usually used. Specifically, preferred electron-withdrawing groups are halogen atoms such as fluorine, chlorine and bromine; and carboxyl groups.

When the substituents introduced in the groups X and Y, and $R^1$ and $R^2$ are electron-donating groups, the covalent bonds in the biodegradable sites become less prone to decomposition than when no substituents are present and consequently the disintegration time of crosslinked acidic polysaccharides in living bodies tends to be extended. The electron-donating groups may be selected while using, for example, Hammett constants as indicators.

The electron-donating groups are not particularly limited as long as they can be introduced into the groups X and Y and also $R^1$ and $R^2$, and may be selected appropriately from those electron-donating groups that are usually used. Specific examples of the electron-donating groups include alkenyl groups and alkynyl groups.

When the substituents introduced in the groups X and Y and also $R^1$ and $R^2$ are steric hindrance groups, the disintegration time of crosslinked acidic polysaccharides in living bodies tends to be extended. When, for example, X is a single bond, the steric hindrance groups in $R^1$ may be selected while using the hydropathy indexes of amino acids as indicators.

Examples of the steric hindrance groups include linear alkyl groups such as methyl group, ethyl group, propyl group and butyl group; branched alkyl groups such as isopropyl group, isobutyl group and t-butyl group; cycloalkyl groups such as cyclohexyl group; and aryl groups such as phenyl group. Of these, among others, branched alkyl groups and cycloalkyl groups are preferable.

Although the substituents in the groups X and Y and in $R^1$ and $R^2$ are not distinctly categorized as electron-withdrawing groups, electron-donating groups or steric hindrance groups, it is still possible to control the rate of the disintegration of crosslinked acidic polysaccharides in living bodies by selecting the types and positions of the substituents while using indicators such as Hammett constants and hydropathy indexes.

Fine adjustment of the disintegration rate is feasible by introducing both electron-withdrawing groups and electron-donating groups. Alternatively, the rate of the disintegration of crosslinked acidic polysaccharides in living bodies may be finely adjusted by introducing substituents having electron-withdrawing properties or electron-donating properties in conjunction with steric hindrance properties.

Those substituents which may be introduced in the groups X and Y, and those electron-withdrawing groups, electron-donating groups and steric hindrance groups which may be introduced in $R^1$ and $R^2$ are selected from the group consisting of hydroxyl groups, alkyl groups having 1 to 6 carbon atom, indolyl groups, diazolyl groups, —$(CH_2)_n$—NHMe groups, —$(CH_2)_n$—$NMe_2$ groups, —$(CH_2)_n$—$CONR^3R^4$ groups, —$(CH_2)_n$—$COOR^5$ groups and —SH groups, and the substituents in X and Y may be selected from the group consisting of phenyl groups, 4-hydroxyphenyl groups, halogen atoms, nitro groups and nitrile groups, wherein n independently at each occurrence represents an integer of 0 to 4.

The structure of the diamine crosslinking agents preferably has the structure of the general formula (I) described above. In particular, the number of atoms in the linear chain between the two terminal amino groups is preferably 5 to 12, more preferably 5 to 8, and most preferably 5 or 6.

It is preferable that the structure of the diamine crosslinking agents be composed solely of naturally occurring amino acids or derivatives thereof. For example, a more preferred diamine crosslinking agent is one having an ester bond or a thioester bond which is obtained by the condensation reaction of at least one —OH group or —SH group in an amino acid derivative selected from the group consisting of serine derivatives, threonine derivatives, tyrosine derivatives and cysteine derivatives, with a carboxyl group in a naturally occurring amino acid. In this case, it is more preferable that the carboxyl groups in the serine derivatives, the threonine derivatives, the tyrosine derivatives and the cysteine derivatives are ester structures or amide structures.

Specific examples of the naturally occurring amino acids include glycine, alanine, β-alanine, asparagine, serine, aspartic acid, cysteine, glutamine, glutamic acid, tyrosine, tryptophan, methionine, phenylalanine, threonine, valine, isoleucine, leucine, histidine, norvaline, norleucine, isoserine, aminobutyric acid, aminovaleric acid, aminoheptanoic acid, aminooctanoic acid, aminodecanoic acid, aminoundecanoic acid, aminododecanoic acid and structural isomers thereof.

Of these, glycine, alanine, β-alanine, asparagine, serine, aspartic acid, cysteine, glutamine, glutamic acid, tyrosine, tryptophan, methionine, phenylalanine, threonine, valine, isoleucine, leucine, histidine, norvaline, norleucine and isoserine may be preferably used.

When the amino acid is aspartic acid or glutamic acid, it is more preferable that the side-chain carboxyl group have an ester structure or an amide structure.

When a derivative of lysine, ornithine or arginine is used in the present invention, the derivative may be one in which the side-chain amino group is N-alkylated.

The compounds of the formula (I) satisfying the aforementioned requirements in the diamine crosslinking agents of the invention, and preferred embodiments thereof will be described below.

The diamine crosslinking agents for acidic polysaccharides according to the invention are as described hereinabove. In the compound of the formula (I) which constitutes the crosslinking agent, X and Y are each independently a single bond (with the proviso that X and Y cannot be single bonds at the same time), a substituted or unsubstituted alkylene group, a substituted or unsubstituted alkenylene group, or a substituted or unsubstituted alkynylene group.

X is preferably a single bond or an optionally halogenated alkylene group, and is more preferably a single bond.

In another preferred embodiment, X is preferably an alkylene group, an alkenylene group or an alkynylene group substituted with phenyl group, 4-hydroxyphenyl group, —$CONR^3R^4$ group, —$COOR^5$ group, halogen atom, nitro group or nitrile group.

Y is preferably a substituted or unsubstituted alkylene group. Here, the substituents in Y are preferably selected from the group consisting of methyl groups, phenyl groups and —$COOR^5$ groups. In another preferred embodiment, Y is preferably >$CR^7R^8$ wherein $R^7$ and $R^8$ are each independently a hydrogen atom, a hydroxyl group, an alkyl group having 1 to 6 carbon atom, a phenyl group, a 4-hydroxyphenyl group, an indolyl group, a diazolyl group, a —$(CH_2)_n$—NHMe group, a —$(CH_2)_n$—$NMe_2$ group, a —$(CH_2)_n$—$CONR_3R_4$ group, a —$(CH_2)_n$—$COOR^5$ group, a —SH group, a halogen atom, a nitro group or a nitrile group, preferably each independently a hydrogen atom, a phenyl group, a 4-hydroxyphenyl group, —$CONR^3R^4$ group, a —$COOR^5$ group, a halogen atom, a nitro group or a nitrile group, and still more preferably a hydrogen atom. In another preferred embodiment, $R^7$ is a hydrogen atom and $R^8$ is a hydrogen atom or a methyl group.

Z represents an oxygen atom or a sulfur atom, and preferably an oxygen atom.

$R^1$ and $R^2$ are each independently a hydrogen atom, a —$CONR^3R^4$ group, a —$COOR^5$ group, a substituted or unsubstituted alkyl group, a substituted or unsubstituted alkenyl group, or a substituted or unsubstituted alkynyl group.

$R^1$ is preferably a hydrogen atom, or a substituted or unsubstituted alkyl group, and more preferably a hydrogen atom.

Here, the substituents in the alkyl group represented by $R^1$ are preferably selected from the group consisting of methyl groups, phenyl groups, indolyl groups, —$COOR^5$ groups and —S—Me groups. In another preferred embodiment, $R^1$ is preferably a hydrogen atom, a —$(CH_2)_2$—S—$CH_3$ group, a —$(CH_2)_{3\ or\ 4}$—NHMe group, a —$(CH_2)_{3\ or\ 4}$—$NMe_2$ group or a $(CH_2)_{1\ or\ 2}$—$COOR^5$ group.

$R^2$ is preferably a hydrogen atom, a —$CONR^3R^4$ group or a —$COOR^5$ group. In another preferred embodiment, $R^2$ is preferably a —$CONR^3R^4$ group or a —$COOR^5$ group.

$R^3$, $R^4$, $R^5$ and $R^6$ are each independently a hydrogen atom or an alkyl group optionally substituted with phenyl group.

In the compound of the formula (I) constituting the diamine crosslinking agent, the number of atoms in the linear chain between the two terminal amino groups is 5 to 12, preferably 5 to 8, and more preferably 5 or 6.

The diamine crosslinking agent is preferably used in the form of divalent salt. The types of the salts are not particularly limited, but pharmaceutically acceptable salts are preferable. Specifically, at least one selected from hydrochloride salts, sulfate salts, carbonate salts, phosphate salts and nitrate salts are preferable, and hydrochloride salts are more preferable.

Branch Structures in Diamine Crosslinking Agents

The crosslinking agent is a triamine crosslinking agent when a substituent having an own biodegradable site and a terminal primary amino group in its structure is selected as the substituent to be introduced in the group X or Y, or as $R^1$ or $R^2$ in the diamine crosslinking agent represented by the general formula (I). Crosslinked acidic polysaccharides similar to those described hereinabove may be produced even by the use of such a polyamine crosslinking agent which has one or more branched primary amino groups having an own biodegradable site. However, the diamine structure having two primary amino groups is more preferable from the point of view of reaction control.

Specific examples of the diamine crosslinking agents represented by the formula (I) include:

2-aminoethyl-2-aminoacetate (GlyC2N), for example GlyC2N.dihydrochloride (Compound 4) (Example 1);

(S)-ethyl-2-amino-3-(2-aminoacetoxy)propanoate (GlySerEt), for example GlySerEt.dihydrochloride (Compound 7) (Example 2);

(S)-2,3-diamino-3-oxopropyl 2-aminoacetate (GlySerNH2), for example GlySerNH2.dihydrochloride (Compound 10) (Example 3);

(S)-2-amino-3-(methylamino)-3-oxopropyl-2-aminoacetate (GlySerNHMe), for example GlySerNHMe.dihydrochloride (Compound 14) (Example 4);

(S)-2-amino-3-(dimethylamino)-3-oxopropyl-2-aminoacetate (GlySerNMe2), for example GlySerNMe2.dihydrochloride (Compound 17) (Example 5);

(S)-ethyl-2-amino-4-(2-aminoacetoxy)butanoate (GlyHomoSerEt), for example GlyHomoSerEt.dihydrochloride (Compound 20) (Example 6);

(2S)-1-aminopropan-2-yl-2-aminopropanoate (AlaC2MeN), for example AlaC2MeN.dihydrochloride (Compound 24) (Example 7);

(S)-1-amino-2-methylpropan-2-yl-2-aminopropanoate (AlaC2Me2N), for example AlaC2Me2N.dihydrochloride (Compound 27) (Example 8);

1-aminopropan-2-yl-2-aminoacetate (GlyC2MeN), for example GlyC2MeN.dihydrochloride (Compound 29) (Example 9);

1-amino-2-methylpropan-2-yl-2-aminoacetate (GlyC2Me2N), for example GlyC2Me2N.dihydrochloride (Compound 31) (Example 10);

S-(2-aminoethyl)-2-aminoethanethioate (GlySC2N), for example GlySC2N.dihydrochloride (Compound 34) (Example 11);

4-(2-aminoethyl)phenyl-2-aminoacetate (GlyPhC2N), for example GlyPhC2N.dihydrochloride (Compound 37) (Example 12);

(S)-2-aminoethyl-2-(2-aminoacetoxy)propanoate (GlyLacC2N), for example GlyLacC2N.dihydrochloride (Compound 42) (Example 13);

(S)-2-amino-3-benzylamino-3-oxopropyl-2-aminoacetate (GlySerNHBn), for example GlySerNHBn.dihydrochloride (Compound 45) (Example 14);

(S)-2-amino-3-(octylamino)-3-oxopropyl-2-aminoacetate (GlySerNHC8), for example GlySerNHC8.dihydrochloride (Compound 48) (Example 15);

(S)-3-amino-4-ethoxy-4-oxobutyl-8-aminooctanoate (OctHomoSerEt), for example OctHomoSerEt.dihydrochloride (Compound 52) (Example 16);

2-aminoethyl 2-(2-aminoacetamido)acetate (GlyGlyC2N), for example GlyGlyC2N.dihydrochloride (Compound 55) (Example 43);

2-(2-aminoethoxy)ethyl 2-aminoacetate (GlyC2OC2N), for example GlyC2OC2N.dihydrochloride (Compound 58) (Example 44);

2-((2-aminoethyl)amino)ethyl 2-aminoacetate (GlyC2NC2N), for example GlyC2NC2N.trihydrochloride (Compound 61) (Example 45);

(S)-2-aminoethyl 2-amino-4-methylpentanoate (LeuC2N), for example LeuC2N.dihydrochloride (Compound 64) (Example 46);

(S)-2-aminoethyl 2-amino-3-phenylpropanoate (PheC2N), for example PheC2N.dihydrochloride (Compound 67) (Example 47);

(S)-2-aminoethyl 2-amino-3-(1H-indol-3-yl)propanoate (TrpC2N), for example TrpC2N.dihydrochloride (Compound 70) (Example 48);

(S)-(2R,3S)-3-amino-4-(ethylamino)-4-oxobutan-2-yl 2-aminopropanoate (AlaThrNHEt), for example AlaThrN-HEt.dihydrochloride (Compound 74) (Example 49);

(S)-2-aminoethyl 2-amino-4-(methylthio)butanoate (MetC2N), for example MetC2N.dihydrochloride (Compound 77) (Example 50);

2-aminoethyl 3-amino-2-fluoropropanoate (βAla(F)C2N), for example βAla(F)C2N.dihydrochloride (Compound 81) (Example 51);

2-aminoethyl 2-amino-2-methylpropanoate ((Me)AlaC2N), for example (Me)AlaC2N.dihydrochloride (Compound 84) (Example 52).

As shown above, the crosslinking agents in the invention have a relatively simple structure. In consideration of reaction efficiency and biocompatibility, the crosslinking agents in the invention are more desirably those having a low molecular weight and a simple structure.

Compounds of Formula (II)

As aspect of the invention resides in a compound represented by the general formula (II) below:

[Chem. 5]

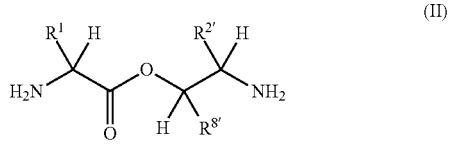

(II)

[wherein
R$^1$ is a hydrogen atom, a —CONR$^3$R$^4$ group, a —COOR$^5$ group, a substituted or unsubstituted alkyl group, a substituted or unsubstituted alkenyl group, or a substituted or unsubstituted alkynyl group;

R$^{2'}$ is a —CONR$^3$R$^4$ group or a —COOR$^5$ group;

any —CH$_2$— in alkyl group, alkenyl group or alkynyl group represented by R$^1$ may be substituted with one or more groups selected from the group consisting of >C=O, —CONH—, an arylene, —O—, —NR$^6$— and —S— (with the proviso that when R$^5$ is a benzyl group, —O— is excluded);

the substituent(s) in R$^1$ is selected from the group consisting of hydroxyl groups, alkyl groups having 1 to 6 carbon atom, indolyl groups, diazolyl groups, —(CH$_2$)$_n$—NHMe groups, —(CH$_2$)$_n$—NMe$_2$ groups, —(CH$_2$)$_n$CONR$^3$R$^4$ groups, —(CH$_2$)$_n$—COOR$^5$ groups and —SH groups (with the proviso that when R$^{2'}$ is a —CONH$_2$ group, —SH groups is excluded) wherein n independently at each occurrence represents an integer of 0 to 4;

R$^3$, R$^4$, R$^5$ and R$^6$ are each independently a hydrogen atom or an alkyl group optionally substituted with phenyl group; and R$^{8'}$ is a hydrogen atom or a methyl group].

As shown above, the compounds of the invention have a relatively simple structure.

Crosslinked Acidic Polysaccharides Prepared with Compounds of General Formula (II)

Another aspect of the invention resides in a crosslinked acidic polysaccharide obtained by forming crosslinks by amide bonding between the primary amino groups in the compound of the general formula (II) and carboxyl groups in an acidic polysaccharide.

Methods for Producing Diamine Crosslinking Agents Represented by Formula (I)

The diamine crosslinking agent represented by the formula (I) may be easily produced by those skilled in the art, starting from naturally occurring compounds or commercially available compounds having desired groups with reference to the following reaction scheme and the methods described in Examples.

[Chem. 6]

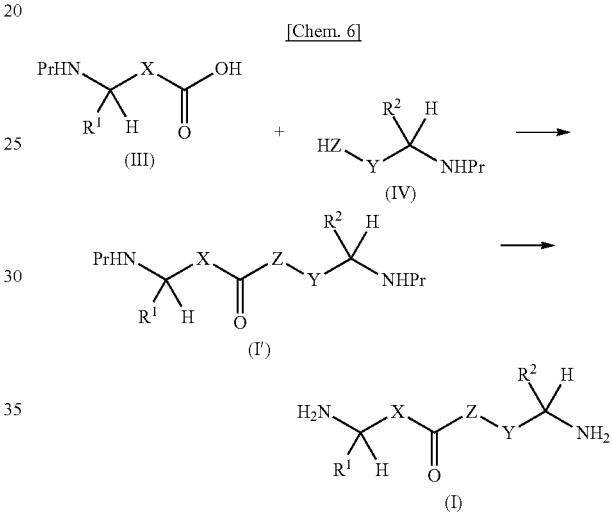

In the above formula, R$^1$, R$^2$, X, Y and Z are as defined in the formula (I), and Pr is an amino-protecting group such as Boc (t-butoxycarbonyl).

Specifically, the diamine crosslinking agent represented by the formula (I) may be prepared by reacting a compound of the formula (III) having a protected amino group with a compound of the formula (IV) having a protected amino group in a solvent in the presence of a condensing agent and optionally in the presence of a base so as to condense the —COOH group possessed by the compound of the formula (III) with the —OH group or the —SH group in the compound of the formula (IV). Preferably, as described earlier, the crosslinking agent may be obtained by condensing at least one —OH group or —SH group in an amino acid derivative selected from the group consisting of naturally occurring amino acid derivatives, for example, serine derivatives, threonine derivatives, tyrosine derivatives and cysteine derivatives, with a carboxyl group in an amino acid derived from a living body.

Although the solvents are not particularly limited as long as the solvents can dissolve the compound of the formula (III) and the compound of the formula (IV), organic solvents are preferable. Examples of the organic solvents include, but not limited to, dichloromethane, dimethylformamide, 1,2-dichloroethane and tetrahydrofuran, with dichloromethane and dimethylformamide being preferable.

Although the condensing agent used may be any of various condensing agents, among others, dicyclohexylcarbodiimide (DCC), diisopropylcarbodiimide (DIC), 1-ethyl-3-(3-dimethylaminopropyl)carbodiimide hydrochloride (EDCI), bis(2-oxo-3-oxazolidinyl)phosphinic chloride (BOP—Cl) and carbonyldiimidazole (CDI) may be suitably used.

The base used may be any of various bases, and, among others, triethylamine and N,N-dimethyl-4-aminopyridine (DMAP) may be suitably used.

Although the temperature in the condensation reaction is not particularly limited and may be selected appropriately in accordance with the type of the solvent used, the temperature is preferably 5 to 60° C., and more preferably 15 to 30° C.

Crosslinked Acidic Polysaccharides and Methods for Production Thereof

Crosslinking is the formation of covalent bonds between polymer molecules. The formation of covalent bonds may occur intramolecularly or between different polymer molecules.

The term crosslinked acidic polysaccharide refers to an acidic polysaccharide that has been crosslinked wherein the crosslinks may be formed by covalent bonding between groups in the same molecule or in different molecules of the acidic polysaccharide.

In the invention, the term crosslinked acidic polysaccharide refers to a product obtained by forming crosslinks by amide bonding between carboxyl groups in acidic polysaccharide molecules through the amino groups in the diamine crosslinking agent. For example, such a product may be obtained by one-step reaction forming the covalent bonds by a usual amidation method. The paired carboxyl groups may be present in the same molecule or in different molecules of the polysaccharide. That is, an aspect of the invention resides in a method for producing crosslinked acidic polysaccharides which includes a step of condensing two carboxyl groups in an acidic polysaccharide with two amino groups in the diamine crosslinking agent by condensation reaction.

In an exemplary amidation method, the reaction is performed a method using a condensing agent such as a water-soluble carbodiimide (for example, 1-ethyl-3-(3-dimethylaminopropyl)carbodiimide) or DMT-MM (4-(4,6-dimethoxy-1,3,5-triazin-2-yl)-4-methylmorpholinium chloride N hydrate) in a solvent, a method to crosslink an acidic polysaccharide and the diamine crosslinking agent using a method such as a symmetric acid anhydride method, a mixed acid anhydride method or an active ester method can be cited. The reaction conditions in the amidation method may be selected appropriately in accordance with the types of the acidic polysaccharide and the diamine crosslinking agent that are used.

The equivalent of the diamine crosslinking agent fed relative to the acidic polysaccharides is preferably 0.001 to 0.500 equivalent (eq), more preferably 0.003 to 0.400 eq, and most preferably 0.005 to 0.300 eq per 1.00 eq of the carboxyl groups in the corresponding acidic polysaccharide. Here, the term "equivalent" indicates the molar equivalent unless otherwise mentioned.

In the reaction of carboxyl groups in the acidic polysaccharide with the diamine crosslinking agent, the concentration of the acidic polysaccharide in the solvent is preferably 0.5 to 50 wt %, and more preferably 1 to 40 wt %.

Although the solvent used in the crosslinking reaction is not particularly limited as long as the solvent can dissolve the acidic polysaccharide and the diamine crosslinking agent, a mixed solvent of water and a water-miscible organic solvent is preferable. The solvent is selected appropriately in consideration of the concentration of the acidic polysaccharide.

The water-miscible organic solvents include lower alcohols such as methanol, ethanol, isopropanol, n-propanol and tertiary butanol, glycol ethers such as ethylene glycol monomethyl ether and ethylene glycol monoethyl ether, acetone, 1,4-dioxane, tetrahydrofuran and acetonitrile, but are not particularly limited. Of these, methanol, ethanol, acetone, tetrahydrofuran and 1,4-dioxane are preferable. A single, or two or more kinds of the water-miscible organic solvents may be mixed with water.

The temperature in the crosslinking reaction is not particularly limited and may be selected appropriately in accordance with the type of the solvent used. The temperature is preferably 5 to 60° C., and more preferably 15 to 30° C.

After the crosslinking reaction, the reaction liquid including the crosslinked product is subjected to 1) a stirring or crushing step, 2) a precipitation step, 3) a washing step and 4) a drying step. In this manner, the final crosslinked acidic polysaccharide may be obtained in the form of dry powder.

The stirring may be performed by a method usually adopted by those skilled in the art, and the stirring method is not particularly limited. The crushing method is not particularly limited and may be performed using a spatula or a device suited for wet crushing. The average particle diameter of the crushed product may be set appropriately in accordance with the type of the medical use of the final crosslinked acidic polysaccharide or depending on the type of the crushing device used.

The precipitation step, the washing step and the drying step may be performed by methods usually adopted by those skilled in the art and are not particularly limited.

In the crosslinking reaction, the amidation method, the reaction solvent, the concentration of the acidic polysaccharide, the structure of the diamine crosslinking agent, and the equivalent of the crosslinking agent fed may be selected appropriately in accordance with the type of the acidic polysaccharide used and the desired characteristics of medical materials.

Crosslinking Ratio

The crosslinking ratio of the crosslinked acidic polysaccharide obtained by the method described above is defined by the general formula (A) below:

[Math. 1]

$$\frac{\text{Number of moles of diamine crosslinking agent whose amino groups at both ends are bonded to acidic polysaccharide (mol)}}{\text{Number of moles of all -COR in crosslinked acidic polysaccharide (mol)}} \times 100(\%) \quad (A)$$

(In the above formula, R indicates —OH, —ONa, or NH crosslinking agent.)

Physical Stress of Swollen Crosslinked Acidic Polysaccharides

The term swollen crosslinked acidic polysaccharide indicates that the crosslinked acidic polysaccharide has absorbed water and been swollen. Further, the term physical stress used in the invention means the resistance force that is produced inside the swollen crosslinked acidic polysaccharide in response to an external force. The magnitude of the stress is defined as the magnitude of the internal force acting on the unit area.

The physical stress of the swollen crosslinked acidic polysaccharides is not particularly limited and is selected appropriately in accordance with the type of the medical use of the materials. The physical stress may be easily controlled by manipulating the type of the diamine crosslinking agent, the equivalent of the diamine crosslinking agent fed, the type of the acidic polysaccharide or the concentration of the crosslinked acidic polysaccharide, or by the addition of a pharmaceutically acceptable salt.

Equilibrium Swelling Concentration of Crosslinked Acidic Polysaccharides

In the invention, the equilibrium swelling concentration means the concentration at which the absorption of water by a powder of the crosslinked acidic polysaccharide reaches a state of equilibrium. Specifically, this concentration may be calculated by allowing a powder of the crosslinked acidic polysaccharide to stand on a filter in contact with saline for 3 days and determining the weight of the crosslinked acidic polysaccharide that has been swollen by absorbing the saline.

Formulation Conditions

The crosslinked acidic polysaccharides of the invention prepared by the method described hereinabove may be processed appropriately in accordance with the type of the medical use, into the desired form or formulation. Specifically, the form or formulation is preferably a swollen material or a suspension using a medically acceptable solvent, or a powder or granules. The formulations may contain pharmaceutically acceptable additives or excipients.

Sterilization Methods

The methods for the sterilization of the inventive crosslinked acidic polysaccharides for medical use are not particularly limited and may be selected appropriately in accordance with the purpose of the medical use, the formulation conditions, and the type of the administration device. Specific examples include EOG sterilization, radiation sterilization and moist-heat (high-pressure steam) sterilization, with radiation sterilization and moist-heat sterilization being preferable.

Medical Materials

The crosslinked acidic polysaccharides of the invention may be used as various medical materials, and examples of such medical materials include tissue bulking materials and adhesion preventing materials. The type of the acidic polysaccharide, the concentration of the acidic polysaccharide during the reaction, and the structure and equivalent of the diamine crosslinking agent may be selected appropriately in accordance with the type of use application.

Tissue Bulking Materials

In the invention, some of the fields to which the tissue bulking materials are applied are the following:

(1) Urological Areas

Stress Urinary Incontinence (SUI) and Vesicoureteral Reflux (VUR)

When used as a tissue bulking material in urological areas, the crosslinked acidic polysaccharide of the invention may be administered into a body in the form of, for example, powder or swollen material with a solvent. The solvent used for swelling is preferably saline, phosphate buffer or the like which contains a pharmaceutically acceptable salt. The concentration of the crosslinked product administered as a tissue bulking material may be determined appropriately in accordance with the desired performance of the tissue bulking material, and the material may be administered by a usual method.

Adhesion Preventing Materials

In the invention, some of the fields to which the adhesion preventing materials are applied are the following:

(1) Obstetric and Gynecologic Areas

The materials may be applied to prevent adhesions associated with, for example, pelvic operation during infertility treatment, uterus operation, tubal operation, ovarian operation, endometiosis treatment operation, cesarean section and pelvic adhesiolysis.

When used as an adhesion preventing material in obstetric and gynecologic areas, the crosslinked acidic polysaccharide of the invention may be applied to a surgical wound in the form of, for example, powder.

(2) Digestive Surgical Areas

The materials may be applied to prevent adhesions associated with, for example, intestinal adhesions after abdominal operation.

When used as an adhesion preventing material in digestive surgical areas, the crosslinked acidic polysaccharide of the invention may be applied to a surgical wound in the form of, for example, powder.

(3) Orthopedic Areas

The materials may be applied to prevent adhesions associated with, for example, Achilles tendon operation, flexor tendon operation, arthroplasty and laminectomy.

When used as an adhesion preventing material in orthopedic areas, the crosslinked acidic polysaccharide of the invention may be applied to a surgical wound in the form of, for example, powder.

Disintegration Time of Crosslinked Acidic Polysaccharides

The disintegration time of the crosslinked acidic polysaccharides in living bodies are not particularly limited and may be selected appropriately in accordance with the type of medical use. The period is preferably 1 week to 2 years, and more preferably 1 week to 1 year. Specifically, when the crosslinked acidic polysaccharide is used as an adhesion preventing material, the disintegration time thereof in living bodies is preferably 3 days to 6 weeks, and more preferably 3 days to 4 weeks. When used as a tissue bulking material, the disintegration time of the crosslinked acidic polysaccharide in living bodies is preferably 2 to 48 weeks, and more preferably 4 to 24 weeks. The disintegration time may be controlled easily by appropriately selecting the structure of the diamine crosslinking agent.

EXAMPLES

Hereinafter, the present invention will be described in detail by presenting Examples and Test Examples without limiting the technical scope of the invention. Unless otherwise mentioned, "%" is on mass basis.

Example 1

Synthesis of 2-aminoethyl-2-aminoacetate (GlyC2N).dihydrochloride (Compound 4)

Compound 4 was synthesized in the following manner.

[Chem. 7]

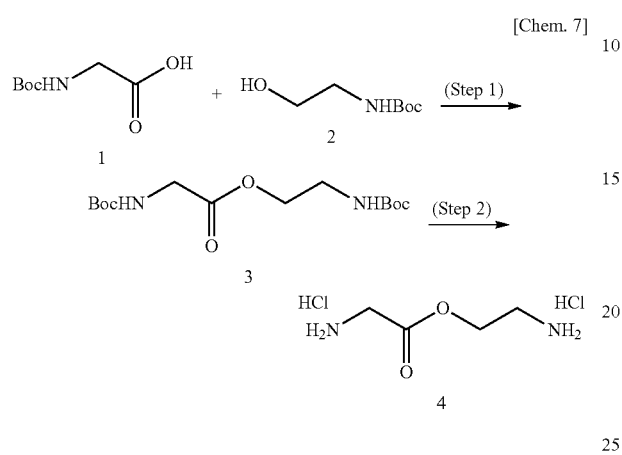

Compound 2 was purchased from Tokyo Chemical Industry Co., Ltd.

(Step 1)

Boc-ethanolamine (Compound 2) (2.65 g, 16.4 mmol) was dissolved into dichloromethane (15 mL), and Boc-glycine (Compound 1) (2.97 g, 16.9 mmol) was added. While performing cooling with ice, N,N-dimethyl-4-aminopyridine (DMAP) (482 mg, 3.95 mmol) and 1-ethyl-3-(3-dimethylaminopropyl)carbodiimide hydrochloride (EDCI) (3.97 g, 20.7 mmol) were added to the solution. The mixture was stirred for 13 hours at room temperature. The reaction liquid was vacuum concentrated, and ethyl acetate (600 mL) was added to the residue. The mixture was washed sequentially with 0.3 N hydrochloric acid (200 mL), a saturated aqueous sodium hydrogen carbonate solution (200 mL) and saturated saline (200 mL). The organic phase was dried with sodium sulfate and was thereafter filtered. The filtrate was vacuum concentrated. The residue was purified by silica gel column chromatography (ethyl acetate/hexane=1/3). Consequently, Compound 3 (5.23 g, 16.4 mmol) was obtained as a colorless transparent viscous liquid (yield 100%).

$^1$H-NMR (500 MHz, CDCl$_3$, δ) 1.45-1.46 (18H, m, Bocx2), 3.40-3.41 (2H, m, CH2), 3.92 (2H, d, J=6 Hz, CH2), 4.22 (2H, t, J=6 Hz), 4.85 (1H, brs, NH), 5.04 (1H, brs, NH)

ESI-MS: Calcd for C14H26N2O6[M+]+, 319.2; found 319.2.

(Step 2)

In an ice bath, 4 N hydrogen chloride/1,4-dioxane (30 mL) was added to Compound 3 (3.00 g, 9.42 mmol). At room temperature, the mixture was stirred for 2 hours. Diethyl ether (150 mL) was added to the reaction liquid, and a white solid was precipitated. The supernatant was removed, and the precipitate was washed with diethyl ether (200 mL) five times. The precipitate was vacuum dried. Thus, title Compound 4 (1.55 g, 8.13 mmol) was obtained as a white solid (yield 86%).

$^1$H-NMR (500 MHz, DMSO-d6, δ) 3.10 (2H, brs, CH2), 3.85 (2H, s, CH2), 4.39 (2H, q, J=2 Hz), 8.45 (3H, brs, NH3), 8.64 (3H, brs, NH3)

Example 2

Synthesis of (S)-ethyl-2-amino-3-(2-aminoacetoxy)propanoate (GlySerEt).dihydrochloride (Compound 7)

Compound 7 was synthesized in the following manner.

[Chem. 8]

Compound 5 was synthesized by the method described in Biochemical Pharmacology, 2006, 71 (3), 268-277.

(Step 1)

In substantially the same manner as in Example 1 (Step 1) except that Boc-ethanolamine used in Example 1 (Step 1) was replaced by Compound 5, Compound 6 (5.12 g, 13.1 mmol) was obtained from Compound 5 (3.38 g, 14.5 mmol) and Compound 1 (2.54 g, 14.5 mmol) as a colorless transparent viscous liquid (yield 90%).

$^1$H-NMR (500 MHz, CDCl$_3$, δ) 1.29 (3H, t, 7 Hz, CH2CH3), 1.45 (18H, m, Bocx2), 3.91 (2H, d, J=6 Hz), 4.23 (2H, dd, J=15 Hz, 7 Hz, CH2CH3), 4.44-4.50 (2H, m, CH2), 4.55-4.58 (1H, m, CH), 4.99 (1H, brs, NH), 5.33 (1H, m, NH)

ESI-MS: Calcd for C17H30N2O8[M+H]+391.2; found 391.2.

(Step 2)

In substantially the same manner as in Example 1 (Step 2) except that Compound 3 used in Example 1 (Step 2) was replaced by Compound 6, title Compound 7 (3.45 g, 13.1 mmol) was obtained from Compound 6 (5.12 g, 13.1 mmol) as a white solid (yield 100%).

$^1$H-NMR (500 MHz, DMSO-d6, δ) 1.25 (3H, t, 7 Hz, CH2CH3), 3.83 (2H, dd, 30 Hz, 18 Hz, CH2), 4.24 (2H, dd, 14 Hz, 7 Hz, CH2CH3), 4.49-4.55 (2H, m, CH2), 4.66 (1H, dd, 12 Hz, 3 Hz, CH), 8.74 (3H, brs, NH3), 9.07 (3H, brs, NH3)

Example 3

Synthesis of (S)-2,3-diamino-3-oxopropyl 2-aminoacetate (GlySerNH2).dihydrochloride (Compound 10)

Compound 10 was synthesized in the following manner.

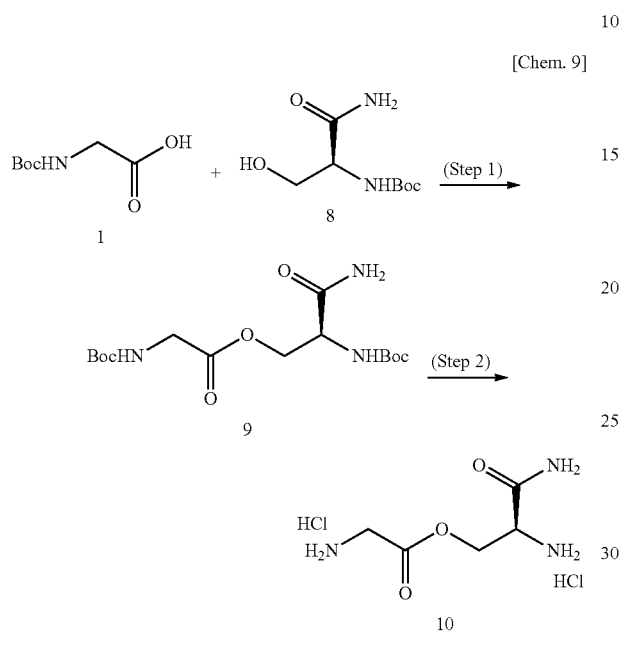

[Chem. 9]

Compound 8 was synthesized by the method described in Synthetic Communications, 1989, 19 (9-10), 1603-9.

(Step 1)

In substantially the same manner as in Example 1 (Step 1) except that Boc-ethanolamine used in Example 1 (Step 1) was replaced by Compound 8, Compound 9 (1.09 g, 3.02 mmol) was obtained from Compound 8 (651 mg, 3.19 mmol) and Compound 1 (615 mg, 3.51 mmol) as a white solid (yield 95%).

$^1$H-NMR (500 MHz, CDCl$_3$, δ) 1.45-1.46 (18H, m, Boc×2), 3.85-3.94 (2H, m, CH2), 4.39-4.48 (3H, m, CH2, CH), 5.09 (1H, brs, NH), 5.45 (1H, brs, NH), 5.57 (1H, brs, NH2), 6.42 (1H, brs, NH2)

ESI-MS: Calcd for C15H27N3O7 [M+H]+362.2; found 362.3.

(Step 2)

In substantially the same manner as in Example 1 (Step 2) except that Compound 3 used in Example 1 (Step 2) was replaced by Compound 9, title Compound 10 (654 mg, 2.80 mmol) was obtained from Compound 9 (1.09 g, 3.02 mmol) as a white solid (yield 92%).

$^1$H-NMR (500 MHz, DMSO-d6, δ) 3.81 (1H, d, J=17 Hz, CH2), 3.85 (1H, d, J=17 Hz, CH2), 4.13 (1H, dd, J=6 Hz, 4 Hz, CH), 4.50 (1H, dd, J=12 Hz, 6 Hz, CH2), 4.57 (1H, dd, J=12 Hz, 4 Hz, CH2), 7.70 (1H, brs, NH2), 8.15 (1H, brs, NH2), 8.55 (6H, brs, NH3×2)

ESI-MS: Calcd for C5H11N3O3 [2M+H]+323.2, found 323.2.

Example 4

Synthesis of (S)-2-amino-3-(methylamino)-3-oxopropyl-2-aminoacetate (GlySerNHMe).dihydrochloride (Compound 14)

Compound 14 was synthesized in the following manner.

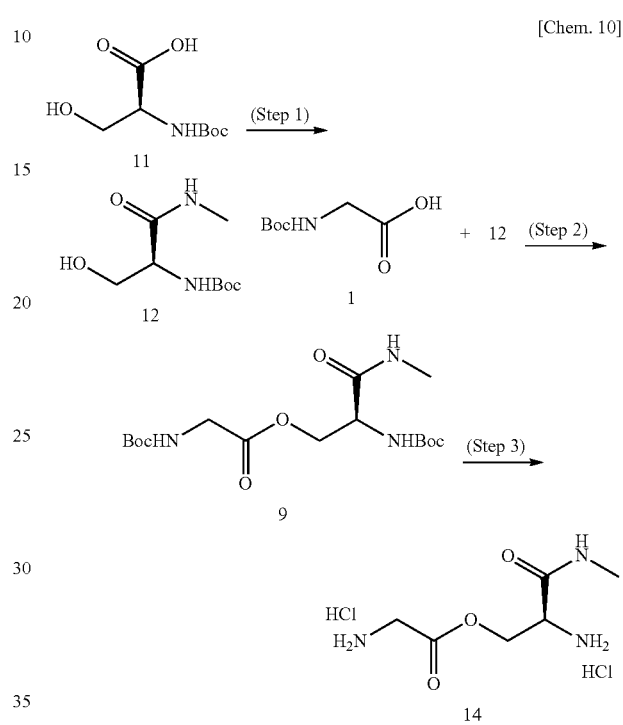

[Chem. 10]

(Step 1)

Boc-serine (Compound 11) (1.00 g, 4.87 mmol) was dissolved into tetrahydrofuran (THF) (30 mL) At room temperature, a 12 M aqueous methylamine solution (0.60 mL, 7.20 mmol) and 4-(4,6-dimethoxy-1,3,5-triazin-2-yl)-4-methylmorpholinium chloride.N hydrate (DMT-MM) (2.70 g, 9.74 mmol) were added. The mixture was stirred at room temperature for 2 hours. Water was added, and extraction was performed with ethyl acetate. The organic phase was washed with saturated saline, dried with sodium sulfate, and filtered. The solvent was distilled off under reduced pressure. The residue was purified by silica gel column chromatography (ethyl acetate:methanol=1:0 to 9:1). Thus, Compound 12 (1.00 g, 4.59 mmol) was obtained as a white solid (yield 94%).

$^1$H-NMR (500 MHz, CDCl$_3$, δ) 1.46 (9H, s, Boc), 2.83 (3H, d, 4.9 Hz, CH3), 3.65 (1H, m, CH), 4.10-4.15 (2H, m, CH2), 5.56 (1H, brs, NH), 6.67 (1H, brs, NH)

ESI-MS: Calcd for C9H18N2O4 [M+H]+, 219.1; found 219.2.

(Step 2)

In substantially the same manner as in Example 1 (Step 1) except that Boc-ethanolamine used in Example 1 (Step 1) was replaced by Compound 12, Compound 13 (1.18 g, 3.15 mmol) was obtained from Compound 12 (810 mg, 3.71 mmol) and Compound 1 (716 mg, 4.09 mmol) as a white solid (yield 85%).

$^1$H-NMR (500 MHz, CDCl$_3$, δ) 1.46 (18H, m, Boc×2), 2.84 (3H, d, 4.9 Hz, CH3), 3.87-3.89 (2H, m, CH2), 4.35-4.46 (3H, m, CH2 and CH), 5.37 (1H, brs, NH), 6.38 (1H, brs, NH), 7.26 (1H, brs, NH)

ESI-MS: Calcd for C16H29N3O7 [M+H]+, 376.2; found 376.3.

(Step 3)

In substantially the same manner as in Example 1 (Step 2) except that Compound 3 used in Example 1 (Step 2) was replaced by Compound 13, title Compound 14 (773 mg, 3.12 mmol) was obtained from Compound 13 (1.18 g, 3.15 mmol) as a white solid (yield 99%).

$^1$H-NMR (500 MHz, DMSO-d6, δ) 2.49 (3H, d, J=5 Hz, CH3), 3.81 (1H, d, J=17 Hz, CH2), 3.86 (1H, d, J=17 Hz, CH2), 4.13 (1H, dd, J=4 Hz, 6 Hz, CH), 4.47 (1H, dd, J=6 Hz 12 Hz, CH2), 4.52 (1H, dd, J=4 Hz, 12 Hz, CH2), 8.55 (6H, brs, NH3), 8.75 (1H, brs, NH)

ESI-MS: Calcd for C6H13N3O3 [M+H]+176.1; found 176.1.

Example 5

Synthesis of (S)-2-amino-3-(dimethylamino)-3-oxy-propyl-2-aminoacetate (GlySerNMe2).dihydrochloride (Compound 17)

Compound 17 was synthesized in the following manner.

[Chem. 11]

Compound 15 was synthesized by the method described in Tetrahedron, 2004, 60 (10), 2247-2257.

(Step 1)

In substantially the same manner as in Example 1 (Step 1) except that Boc-ethanolamine used in Example 1 (Step 1) was replaced by Compound 15, Compound 16 (858 mg, 2.20 mmol) was obtained from Compound 15 (608 mg, 2.62 mmol) and Compound 1 (505 mg, 2.88 mmol) as a white solid (yield 84%).

$^1$H-NMR (500 MHz, CDCl$_3$, δ) 1.44-1.45 (18H, m, Bocx2), 2.97 (3H, s, CH3), 3.16 (3H, s, CH3), 3.88 (1H, dd, J=5 Hz, 18 Hz, CH2), 3.97 (1H, dd, 6 Hz, 18 Hz, CH2), 4.03 (1H, dd, 8 Hz, 11 Hz, CH2), 4.41 (1H, dd, 4 Hz, 11 Hz, CH2), 4.92-4.96 (1H, m, CH), 5.05 (1H, brs, NH), 5.56 (1H, d, J=8 Hz, NH), 7.26 (1H, brs, NH)

ESI-MS: Calcd for C17H31N3O7 [M+H]+390.2; found 390.2.

(Step 2)

In substantially the same manner as in Example 1 (Step 2) except that Compound 3 used in Example 1 (Step 2) was replaced by Compound 16, title Compound 17 (509 mg, 1.94 mmol) was obtained from Compound 16 (853 mg, 2.19 mmol), as a white solid (yield 89%).

$^1$H-NMR (500 MHz, DMSO-d6, δ) 2.93 (3H, s, CH3), 3.12 (3H, s, CH3), 3.81 (1H, d, J=17 Hz, CH2), 3.88 (1H, d, J=17 Hz, CH2), 4.33 (1H, dd, J=7 Hz, 12 Hz, CH2), 4.56 (1H, dd, 3 Hz 12 Hz, CH2), 4.65 (1H, dd, J=3 Hz, 7 Hz, CH2), 8.54 (6H, brs, NH3×2)

ESI-MS: Calcd for C7H15N3O3 [M+H]+190.1; found 190.1.

Example 6

Synthesis of (S)-ethyl-2-amino-4-(2-aminoacetoxy)butanoate (GlyHomoSerEt).dihydrochloride (Compound 20)

Compound 20 was synthesized in the following manner

[Chem. 12]

Compound 18 was synthesized by the method described in Journal of Organic Chemistry, 2008, 73 (8), 3212-3217.

(Step 1)

In substantially the same manner as in Example 1 (Step 1) except that Boc-ethanolamine used in Example 1 (Step 1) was replaced by Compound 18, Compound 19 (3.59 g, 8.87 mmol) was obtained from Compound 18 (2.19 g, 8.87 mmol) and Compound 1 (1.61 g, 9.19 mmol) as a colorless transparent viscous liquid (yield 100%).

$^1$H-NMR (500 MHz, CDCl$_3$, δ) 1.29 (3H, t, J=7 Hz, CH2C$\underline{H}$3), 1.44-1.45 (18H, m, Bocx2), 2.00-2.08 (1H, m, CH), 2.00-2.25 (1H, m, CH), 3.85-3.95 (2H, m, CH2), 4.10-4.29 (4H, m, C$\underline{H2}$CH3, CH2), 4.35-4.43 (1H, m, CH), 4.77-5.16 (2H, m, NH)

ESI-MS: Calcd for C18H32N2O8 [M+H]+, 405.2; found 405.3.

(Step 2)

In substantially the same manner as in Example 1 (Step 2) except that Compound 3 used in Example 1 (Step 2) was replaced by Compound 19 and 4 N hydrogen chloride/1,4-dioxane was replaced by 4 N hydrogen chloride/ethyl acetate, title Compound 20 (1.32 g, 4.75 mmol) was obtained from Compound 19 (1.92 g, 4.75 mmol) as a white solid (yield 100%).

$^1$H-NMR (500 MHz, DMSO-d6, δ) 1.25 (3H, t, J=7 Hz, CH2CH3), 2.18-2.27 (2H, m, C112), 3.78 (2H, s, CH2), 4.17-4.26 (3H, m, CH2CH3, CH), 4.27-4.31 (2H, m, CH2), 8.72 (6H, brs, NH3×2)

Example 7

Synthesis of (2S)-1-aminopropan-2-yl-2-aminopropanoate (AlaC2MeN).dihydrochloride (Compound 24)

Compound 24 was synthesized in the following manner.

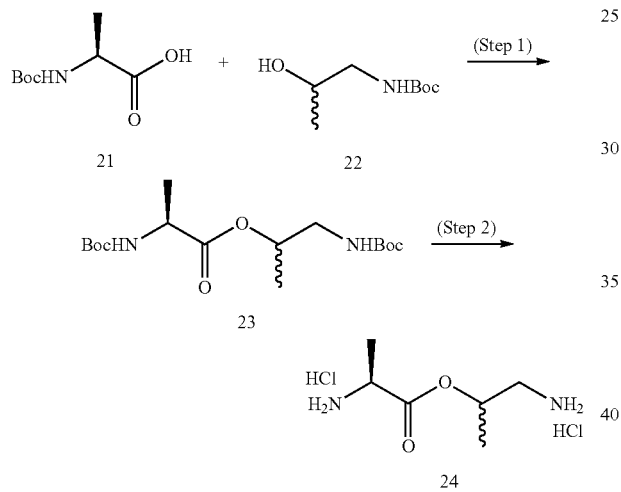

[Chem. 13]

Compound 22 was synthesized by the method described in Journal of Medicinal Chemistry, 2004, 47 (5), 1259-1271.

(Step 1)

In substantially the same manner as in Example 1 (Step 1) except that Boc-ethanolamine used in Example 1 (Step 1) was replaced by Compound 22, Boc-glycine (Compound 1) was replaced by Boc-L-alanine (Compound 21) and triethylamine was further added in 1.09 eq relative to Compound 22, Compound 23 (6.02 g, 17.4 mmol) was obtained from Compound 22 (4.62 g, 26.4 mmol) and Compound 21 (5.03 g, 26.4 mmol) as a colorless transparent viscous liquid (yield 66%).

$^1$H-NMR (500 MHz, CDCl$_3$, 55° C., δ) 1.23 (3H, t, J=7 Hz, CH3), 1.37 (3H, t, J=8 Hz, CH3), 1.43 (9H, s, Boc), 1.45 (9H, s, Boc), 3.17-3.23 (1H, m), 3.36 (1H, brs), 4.20-4.22 (1H, m), 4.78 (1H, brs), 4.99 (1H, brs), 5.00-5.02 (1H, m)

(Step 2)

In substantially the same manner as in Example 1 (Step 2) except that Compound 3 used in Example 1 (Step 2) was replaced by Compound 23, title Compound 24 (1.33 g, 6.09 mmol) was obtained from Compound 23 (2.11 g, 6.09 mmol) as a white solid (yield 100%).

$^1$H-NMR (500 MHz, DMSO-d6, δ) 1.28 (3H, dd, J=1 Hz, 7 Hz, CH3), 1.46 (3H, d, J=8 Hz, CH3), 2.98-3.03 (1H, dd, J=9 Hz, 14 Hz), 3.12 (1H, dd, J=2 Hz, 14 Hz), 3.33 (1H, brs), 4.05 (0.5H, q, J=8 Hz), 4.16 (0.5H, q, J=8 Hz), 5.09 (1H, q, J=7 Hz), 8.54 (6H, brs, NH3×2)

Example 8

Synthesis of (S)-1-amino-2-methylpropan-2-yl-2-aminopropanoate (AlaC2Me2N).dihydrochloride (Compound 27)

Compound 27 was synthesized in the following manner

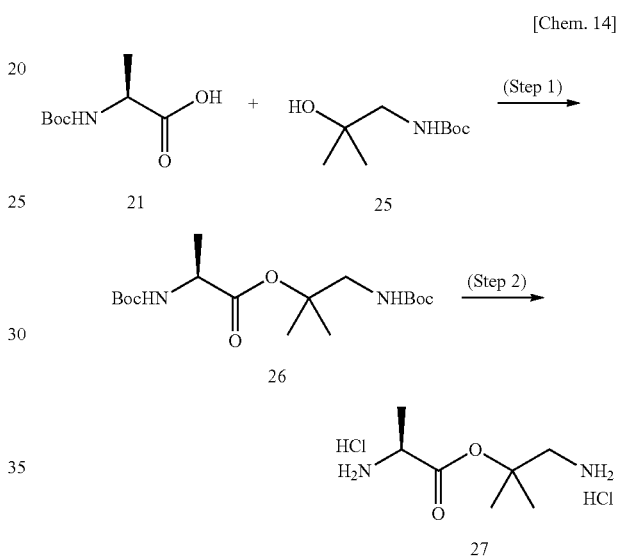

[Chem. 14]

Compound 25 was synthesized by the method described in Journal of Molecular Catalysis A: Chemical, 2006, 253 (1-2), 198-202.

(Step 1)

In substantially the same manner as in Example 7 (Step 1) except that Compound 22 used in Example 7 (Step 1) was replaced by Compound 25, Compound 26 (4.72 g, 13.1 mmol) was obtained from Compound 25 (4.70 g, 24.8 mmol) and Compound 21 (4.71 g, 24.9 mmol) as a colorless transparent viscous liquid (yield 47%).

$^1$H-NMR (500 MHz, CDCl$_3$, 55° C., δ) 1.34 (3H, d, J=8 Hz, CH3), 1.43 (6H, s, CH3×2), 1.44 (18H, s, Boc×2), 3.41 (2H, d, J=5 Hz, CH2), 4.12 (1H, q, J=8 Hz, CH), 4.88 (1H, brs, NH), 5.11 (1H, brs, NH)

(Step 2)

In substantially the same manner as in Example 1 (Step 2) except that Compound 3 used in Example 1 (Step 2) was replaced by Compound 26, title Compound 27 (651 mg, 2.79 mmol) was obtained from Compound 26 (1.01 g, 2.80 mmol) as a white solid (yield 100%).

$^1$H-NMR (500 MHz, DMSO-d6, δ) 1.43 (3H, d, J=7 Hz, CH3), 1.54 (3H, s, CH3), 1.56 (3H, s, CH3), 3.08-3.16 (2H, m, CH2), 4.01 (1H, brs, CH), 8.51 (3H, brs, NH3), 8.75 (3H, brs, NH3)

Example 9

Synthesis of 1-aminopropan-2-yl-2-aminoacetate (GlyC2MeN).dihydrochloride (Compound 29)

Compound 29 was synthesized in the following manner.

[Chem. 15]

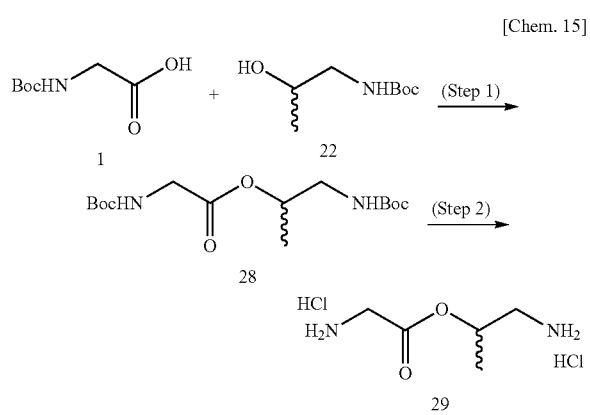

Compound 22 was synthesized by the method described in Journal of Medicinal Chemistry, 2004, 47 (5), 1259-1271.

(Step 1)

In substantially the same manner as in Example 1 (Step 1) except that Boc-ethanolamine used in Example 1 (Step 1) was replaced by Compound 22 and triethylamine was further added in 1.11 eq relative to Compound 22, Compound 28 (4.45 g, 13.4 mmol) was obtained from Compound 22 (5.41 g, 28.5 mmol) and Compound 1 (5.02 g, 28.5 mmol) as a colorless transparent viscous liquid (yield 47%).

$^1$H-NMR (500 MHz, CDCl$_3$, 55° C., δ) 1.24 (3H, d, J=7 Hz, CH3), 1.44 (9H, s, Boc), 1.46 (9H, s, Boc), 3.16-3.21 (1H, m, CH), 3.35 (1H, brs, CH), 3.86 (2H, d, J=6 Hz, CH2), 4.75 (1H, brs, NH), 4.94 (1H, brs, NH), 5.02 (1H, q, J=7 Hz, CH)

(Step 2)

In substantially the same manner as in Example 1 (Step 2) except that Compound 3 used in Example 1 (Step 2) was replaced by Compound 28, title Compound 29 (2.41 g, 11.8 mmol) was obtained from Compound 28 (4.11 g, 12.4 mmol) as a white solid (yield 95%).

$^1$H-NMR (500 MHz, DMSO-d6, δ) 1.29 (3H, d, J=7 Hz, CH3), 3.00 (1H, dd, J=9 Hz, 13 Hz, CH), 3.10 (1H, d, J=13 Hz, CH), 3.78 (1H, d, J=17 Hz, CH), 3.92 (1J, d, J=17 Hz, CH), 5.09-5.13 (1H, m, CH), 8.39 (3H, brs, NH3), 8.53 (3H, brs, NH3)

Example 10

Synthesis of 1-amino-2-methylpropan-2-yl-2-aminoacetate (GlyC2Me2N).dihydrochloride (Compound 31)

Compound 31 was synthesized in the following manner.

[Chem. 16]

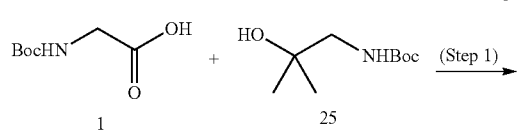

-continued

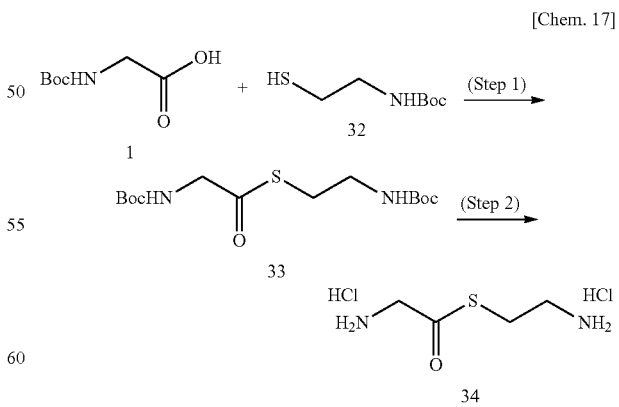

Compound 25 was synthesized by the method described in Journal of Molecular Catalysis A: Chemical, 2006, 253 (1-2), 198-202.

(Step 1)

In substantially the same manner as in Example 1 (Step 1) except that Boc-ethanolamine used in Example 1 (Step 1) was replaced by Compound 25 and triethylamine was further added in 1.10 eq relative to Compound 25, Compound 30 (655 mg, 1.89 mmol) was obtained from Compound 25 (2.71 g, 14.3 mmol) and Compound 1 (2.52 g, 14.4 mmol) as a colorless transparent viscous liquid (yield 13%).

$^1$H-NMR (500 MHz, CDCl$_3$, 55° C., δ) 1.45 (18H, s, Boc×2), 1.53 (6H, s, CH3×2), 3.38 (2H, t, J=8 Hz, CH2), 3.78 (1H, d, J=6 Hz, CH), 4.46 (1H, d, J=6 Hz, CH), 4.95 (1H, brs, NH), 5.17 (1H, brs, NH)

(Step 2)

In substantially the same manner as in Example 1 (Step 2) except that Compound 3 used in Example 1 (Step 2) was replaced by Compound 30, title Compound 31 (400 mg, 1.83 mmol) was obtained from Compound 30 (655 mg, 1.89 mmol) as a white solid (yield 97%).

$^1$H-NMR (500 MHz, DMSO-d6, δ) 1.53 (3H, s, CH3), 1.57 (3H, s, CH3), 3.10 (1H, s, CH), 3.13 (1H, s, CH), 3.74 (1H, s, CH), 3.96 (1H, d, J=6 Hz, CH), 8.43 (3H, brs, NH3), 8.50 (3H, brs, NH3)

Example 11

Synthesis of S-(2-aminoethyl)-2-aminoethanethioate (GlySC2N).dihydrochloride (Compound 34)

Compound 34 was synthesized in the following manner

[Chem. 17]

Compound 32 was purchased from Aldrich.

(Step 1)

In substantially the same manner as in Example 1 (Step 1) except that Boc-ethanolamine used in Example 1 (Step 1)

was replaced by Compound 32, EDCI was replaced by 1.20 eq of bis(2-oxo-3-oxazolydinyl)phosphinic chloride (BOP—Cl) relative to Compound 32 and triethylamine was further added in 2.40 eq relative to Compound 32, Compound 33 (3.78 g, 11.3 mmol) was obtained from Compound 32 (2.00 g, 11.3 mmol) and Compound 1 (2.17 g, 12.4 mmol) as a colorless transparent viscous liquid (yield 100%).

$^1$H-NMR (500 MHz, CDCl$_3$, δ) 1.44-1.47 (18H, m, Bocx2), 3.03-3.07 (2H, m, CH2), 3.30-3.31 (2H, m, CH2), 4.05 (2H, d, J=6 Hz, CH2), 4.82 (1H, brs, NH), 5.12-5.22 (1H, m, NH)

ESI-MS: Calcd for C14H26N2O5S [M+H]+, 335.2; found 335.2.

(Step 2)

In substantially the same manner as in Example 6 (Step 2) except that Compound 19 used in Example 6 (Step 2) was replaced by Compound 33, title Compound 34 (821 mg, 3.96 mmol) was obtained from Compound 33 (1.36 g, 4.07 mmol) as a white solid (yield 97%).

$^1$H-NMR (500 MHz, DMSO-d6, δ) 2.97-3.00 (2H, m, CH2), 3.25 (2H, t, J=7 Hz, CH2), 4.09 (2H, brs, CH2), 8.37 (3H, brs, NH3), 8.60 (3H, brs, H3N)

ESI-MS: Calcd for C4H10N2OS [M+H]+, 135.1; found 135.1.

Example 12

Synthesis of 4-(2-aminoethyl)phenyl-2-aminoacetate (GlyPhC2N).dihydrochloride (Compound 37)

Compound 37 was synthesized in the following manner.

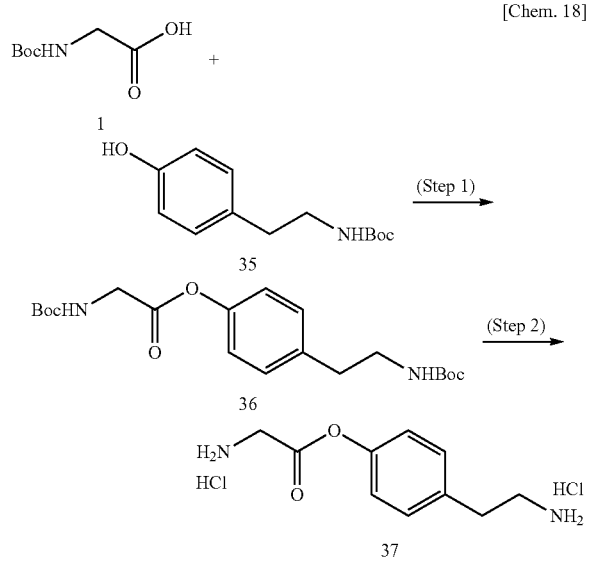

[Chem. 18]

Compound 35 was purchased from Tokyo Chemical Industry Co., Ltd.

(Step 1)

In substantially the same manner as in Example 1 (Step 1) except that Boc-ethanolamine used in Example 1 (Step 1) was replaced by N-Boc-tyramine Compound 35) and dichloromethane was replaced by N,N-dimethylformamide, Compound 36 (3.30 g, 8.37 mmol) was obtained from Compound 35 (2.00 g, 8.43 mmol) and Compound 1 (1.62 g, 9.26 mmol) as a white solid (yield 99%).

$^1$H-NMR (500 MHz, CDCl$_3$, δ) 1.44 (9H, s, Boc), 1.47 (9H, s, Boc), 2.70-2.81 (2H, m, CH2), 3.36-3.73 (2H, m, CH2), 4.16-4.17 (2H, m, CH2), 4.55 (1H, brs, NH), 5.08 (1H, brs, NH), 7.04 (2H, d, J=9 Hz, Ph), 7.20 (2H, d, J=9 Hz, Ph)

ESI-MS: Calcd for C20H30N2O6 [M+NH4]+, 412.2; found 412.3.

(Step 2)

In substantially the same manner as in Example 6 (Step 2) except that Compound 19 used in Example 6 (Step 2) was replaced by Compound 36, title Compound 37 (674 mg, 2.52 mmol) was obtained from Compound 36 (996 mg, 2.52 mmol) as a white solid (yield 100%).

$^1$H-NMR (500 MHz, DMSO-d6, δ) 2.92-2.95 (2H, m, CH2), 3.02-3.05 (2H, m, CH2), 4.07 (2H, s, CH2), 7.14-7.17 (2H, m, Ph), 7.35-7.38 (2H, m, Ph), 8.25-8.61 (6H, m, NH3×2)

ESI-MS: Calcd for C10H14N2O2 [M+H]+, 195.1; found 195.2.

Example 13

Synthesis of (S)-2-aminoethyl-2-(2-aminoacetoxy) propanoate (GlyLacC2N).dihydrochloride (Compound 42)

Compound 42 was synthesized in the following manner.

[Chem. 19]

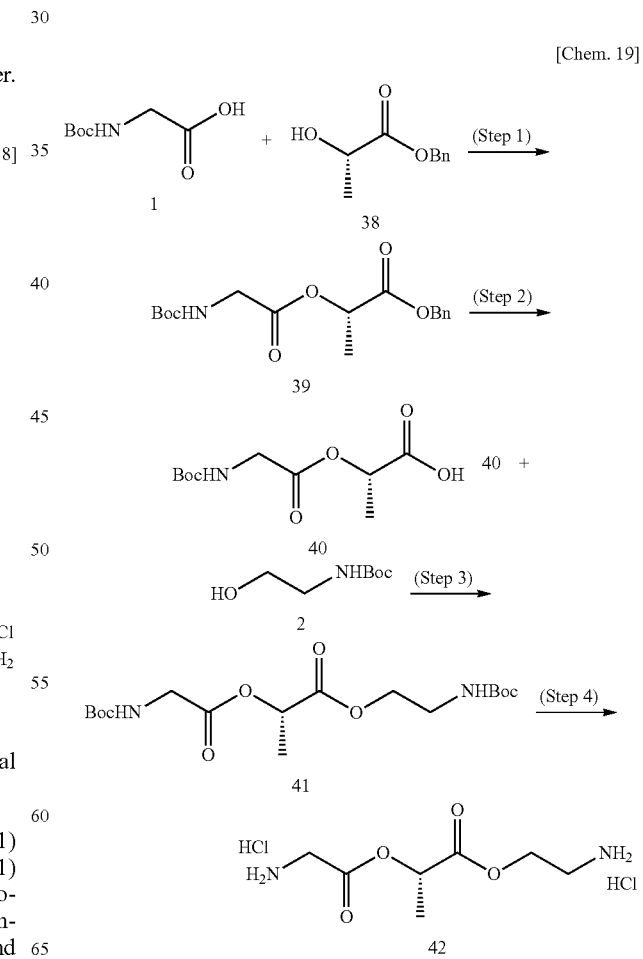

Compound 38 was purchased from Tokyo Chemical Industry Co., Ltd.

(Step 1)

In substantially the same manner as in Example 1 (Step 1) except that Boc-ethanolamine (Compound 2) used in Example 1 (Step 1) was replaced by Compound 38, Compound 39 (8.60 g, 25.5 mmol) was obtained from Compound 38 (5.00 g, 27.8 mmol) and Compound 1 (5.10 g, 29.1 mmol) as a white solid (yield 92%).

$^1$H-NMR (500 MHz, CDCl$_3$, δ) 1.45 (9H, s, Boc), 1.51-1.52 (3H, m, CH3), 3.92-4.08 (2H, m, CH2), 4.98 (1H, brs, NH), 5.15-5.23 (3H, m, CH2, CH), 7.32-7.39 (5H, m, Ph)

ESI-MS: Calcd for C17H23NO6 [M+NH4]+, 355.2; found 355.2.

(Steps 2 and 3)

Compound 39 (4.60 g, 13.6 mmol) was dissolved into ethyl acetate (EtOAc) (50 mL), and 10% palladium carbon (Pd/C) (232 mg, 5.05 wt %) was added. Under hydrogen atmosphere, the mixture was stirred at room temperature overnight. The reaction liquid was filtered, and the filtrate was vacuum concentrated. Thus, crude Compound 40 (3.82 g) was obtained as a colorless transparent viscous liquid.

Subsequently, in substantially the same manner as in Example 1 (Step 1) except that Boc-glycine (Compound 1) used in Example 1 (Step 1) was replaced by Compound 40, Compound 41 (3.82 g, 9.78 mmol) was obtained from the whole of crude Compound 40 and Compound 2 (2.20 g, 13.7 mmol) as a white solid (yield in 2 steps: 72%).

$^1$H-NMR (500 MHz, CDCl$_3$, δ) 1.45 (18H, s, Boc×2), 1.52-1.53 (3H, m, CH3), 3.37-3.41 (2H, m, CH2), 3.92-4.06 (2H, m, CH2), 4.15-4.27 (2H, m, CH2), 5.04 (2H, brs, NH×2), 5.12 (1H, dd, J=14 Hz, 7 Hz, CH)

ESI-MS: Calcd for C17H30N2O8 [M+H]+, 391.2; found 391.3.

(Step 4)

In substantially the same manner as in Example 6 (Step 2) except that Compound 19 used in Example 6 (Step 2) was replaced by Compound 41, title Compound 42 (645 mg, 2.45 mmol) was obtained from Compound 41 (1.01 g, 2.58 mmol) as a white solid (yield 95%).

$^1$H-NMR (500 MHz, DMSO-d6, δ) 1.51 (3H, d, J=7 Hz, CH3), 3.11 (2H, t, J=5 Hz, CH2), 3.86-3.97 (2H, s, CH2), 4.29-4.32 (2H, m, CH2), 5.24 (1H, dd, J=14 Hz, 7 Hz, CH), 8.50 (6H, brs, NH3×2)

ESI-MS: Calcd for C7H14N2O4 [M+H]+, 191.1; found 191.1.

Example 14

Synthesis of (S)-2-amino-3-benzylamino-3-oxopropyl-2-aminoacetate (GlySerNHBn).dihydrochloride (Compound 45)

Compound 45 was synthesized in the following manner.

[Chem. 20]

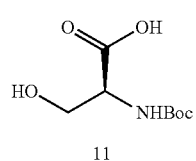

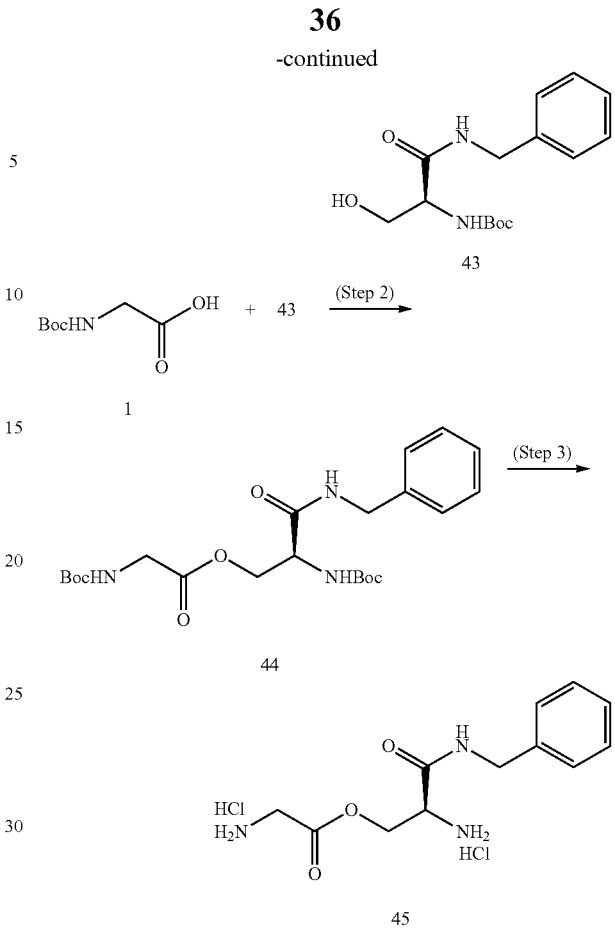

(Step 1)

Boc-L-serine (Compound 11) (2.00 g, 9.77 mmol) was dissolved into methanol (MeOH) (30 mL), and benzylamine (1.63 mL, 14.6 mmol) and DMT-MM (3.97 g, 14.4 mmol) were added sequentially. The mixture was stirred at room temperature for 4 hours. The reaction liquid was vacuum concentrated, diluted with ethyl acetate (EtOAc) (50 mL), and washed with water (50 mL×3), 0.5 N aqueous HCl solution (50 mL) and saturated saline (50 mL). The organic phase was dried with sodium sulfate and was filtered, and the filtrate was vacuum concentrated. The residue was vacuum dried. Thus, Compound 43 (2.82 g, 9.59 mmol) was obtained as a white solid (yield 98%).

$^1$H-NMR (500 MHz, CDCl$_3$, δ) 1.41 (9H, s, Boc), 3.54 (1H, brs, OH), 3.67-3.70 (1H, m, CH), 4.06 (1H, d, J=9 Hz, CH), 4.19 (1H, m, CH), 4.38-4.45 (2H, m, CH2), 5.69 (1H, d, J=8 Hz, NH), 7.16 (1H, brs, HN), 7.23-7.32 (5H, m, Ph)

ESI-MS: Calcd for C15H22N2O4 [M+H]+, 295.2; found 295.4.

(Step 2)

In substantially the same manner as in Example 1 (Step 1) except that Boc-ethanolamine (Compound 2) used in Example 1 (Step 1) was replaced by Compound 43, Compound 44 (2.25 g, 4.98 mmol) was obtained from Compound 43 (1.64 g, 5.56 mmol) and Compound 1 (1.04 g, 5.91 mmol) as a white solid (yield 90%).

$^1$H-NMR (500 MHz, CDCl$_3$, δ) 1.41-1.42 (18H, s, Boc× 2), 3.79 (2H, d, J=6 Hz, CH2), 4.35-4.48 (5H, m, CH2×2, CH), 5.31 (1H, m, NH), 5.68 (1H, d, J=7 Hz, NH), 7.15 (1H, m, NH), 7.22-7.31 (5H, m, Ph)

ESI-MS: Calcd for C22H33N3O7 [M+H]+, 452.2; found 452.4.

(Step 3)

In substantially the same manner as in Example 6 (Step 2) except that Compound 19 used in Example 6 (Step 2) was replaced by Compound 44, title Compound 45 (785 mg, 2.42 mmol) was obtained from Compound 44 (1.16 g, 2.58 mmol) as a white solid (yield 94%).

1H-NMR (500 MHz, DMSO-d6, δ) 3.81 (2H, dd, J=32 Hz, 17 Hz, CH2), 4.25 (1H, t, J=5 Hz, CH), 4.36 (2H, ddd, J=26 Hz, 15 Hz, 6 Hz, CH2), 4.54-4.69 (2H, m, CH2), 7.25-7.36 (5H, m, Ph), 8.63-8.68 (6H, brs, NH3×2), 9.37 (1H, t, J=6 Hz, NH)

ESI-MS: Calcd for C12H17N3O3 [M+H]+, 252.1; found 252.2.

Example 15

Synthesis of (S)-2-amino-3-(octylamino)-3-oxopropyl-2-aminoacetate (GlySerNHC8).dihydrochloride (Compound 48)

Compound 48 was synthesized in the following manner.

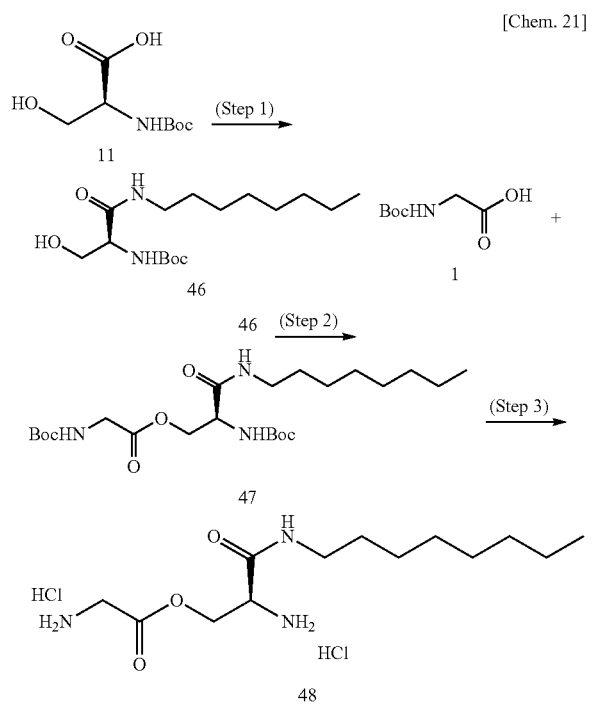

(Steps 1 and 2)

In substantially the same manner as in Example 14 (Step 1) except that benzylamine used in Example 14 (Step 1) was replaced by n-octylamine, crude Compound 46 (3.31 g) was obtained from Compound 11 (2.00 g, 9.74 mmol) and n-octylamine (2.47 mL, 14.6 mmol) as a white solid.

Subsequently, in substantially the same manner as in Example 1 (Step 1) except that Boc-ethanolamine (Compound 2) used in Example 1 (Step 1) was replaced by Compound 46, Compound 47 (2.61 g, 5.53 mmol) was obtained from crude Compound 46 (2.05 g, 6.04 mmol (calculated regarding the purity as 93.0 wt %)) and Compound 1 (1.17 g, 6.67 mmol) as a colorless transparent viscous liquid (yield in 2 steps: 92%).

1H-NMR (500 MHz, CDCl3, δ) 0.88 (3H, t, J=7 Hz, CH3), 1.26-1.29 (10H, m, CH2×5), 1.45-1.52 (20H, m, CH2, Boc×2), 3.25 (2H, dd, J=14 Hz, 7 Hz, CH2), 3.87-3.92 (2H, m, CH2), 4.36-4.44 (3H, m, CH, CH2), 5.16 (1H, brs, NH), 5.46 (1H, brs, NH), 6.49 (1H, brs, NH)

ESI-MS: Calcd for C23H43N3O7 [M+H]+, 474.3; found 474.5.

(Step 3)

In substantially the same manner as in Example 6 (Step 2) except that Compound 19 used in Example 6 (Step 2) was replaced by Compound 47, title Compound 48 (803 mg, 2.32 mmol) was obtained from Compound 47 (1.23 g, 2.61 mmol) as a white solid (yield 89%).

1H-NMR (500 MHz, DMSO-d6, δ) 0.86 (3H, t, J=7 Hz, CH3), 1.26-1.30 (10H, m, CH2×5), 1.41-1.45 (2H, m, CH2), 3.09-3.13 (2H, m, CH2), 3.82 (2H, dd, J=26 Hz, 18 Hz, CH2), 4.13 (1H, dd, J=6 Hz, 5 Hz, CH), 4.49 (2H, ddd, J=22 Hz, 12 Hz, 5 Hz, CH2), 8.58 (6H, brs, NH3×2), 8.78 (1H, t, J=6 Hz, NH)

ESI-MS: Calcd for C13H27N3O3 [M+H]+, 274.2; found 274.3.

Example 16

Synthesis of (S)-3-amino-4-ethoxy-4-oxobutyl-8-aminooctanoate (OctHomoSerEt).dihydrochloride (Compound 52)

Compound 52 was synthesized in the following manner.

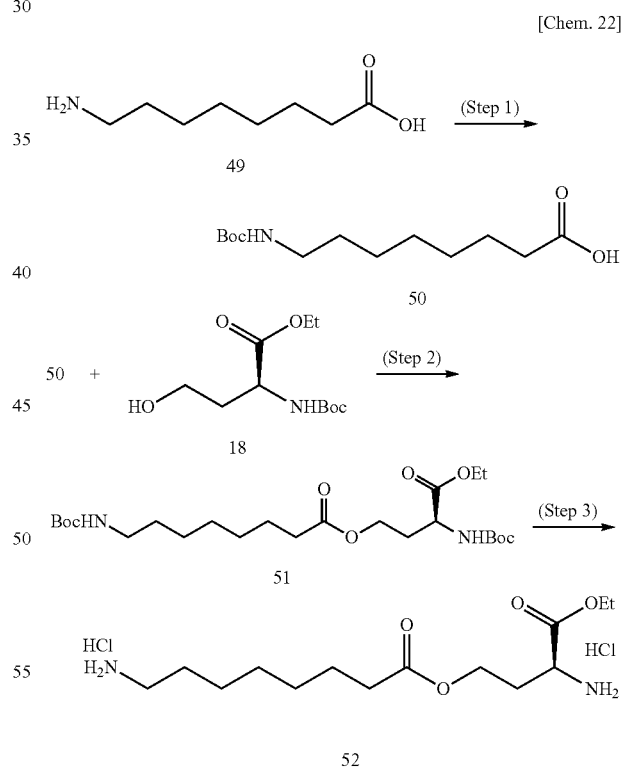

Compound 18 was synthesized by the method described in Journal of Organic Chemistry, 2008, 73 (8), 3212-3217.

(Steps 1 and 2)

8-Aminooctanoic acid (Compound 49) (1.49 g, 9.39 mmol) was dissolved into 1,4-dioxane:1 N aqueous sodium hydroxide solution=2:1 (30 mL). While performing cooling with ice, a solution of di-tert-butyl dicarbonate (2.47 g, 11.3 mmol) in dioxane:water=2:1 (30 mL) was added dropwise. The mixture was stirred at room temperature for 15 hours. The reaction liquid was vacuum concentrated, diluted with ethyl acetate (45 mL), and washed with water (75 mL×2) and 0.2 N hydrochloric acid (50 mL). The organic phase was dried with sodium sulfate and was filtered, and the filtrate was vacuum concentrated. The residue was vacuum dried. Thus, crude Compound 50 (2.73 g) was obtained as a white solid.

Subsequently, in substantially the same manner as in Example 1 (Step 1) except that Boc-glycine (Compound 1) used in Example 1 (Step 1) was replaced by Compound 50 and Boc-ethanolamine (Compound 2) was replaced by Compound 18, Compound 51 (1.17 g, 2.47 mmol) was obtained from crude Compound 50 (1.02 g, 3.52 mmol (calculated regarding the purity as 89.2 wt %)) and Compound 18 (1.10 g, 4.45 mmol) as a white solid (yield in 2 steps: 70%).

$^1$H-NMR (500 MHz, CDCl$_3$, δ) 1.27-1.31 (11H, m, CH3, CH2×4), 1.44 (18H, brs, Boc×2), 1.60-1.62 (2H, m, CH2), 1.99-2.04 (1H, m, CH), 2.16-2.20 (1H, m, CH), 2.28 (2H, t, J=8 Hz, CH2), 3.09-3.10 (2H, m, CH2), 4.12 (1H, dt, J=12 Hz, 6 Hz, CH), 4.16-4.23 (3H, m, CH2, CH), 4.38-4.39 (1H, m, CH), 4.58 (1H, brs, NH), 5.18 (1H, d, J=7 Hz, NH)

ESI-MS: Calcd for C24H44N2O8 [M+H]+, 489.3; found 489.4.

(Step 3)

In substantially the same manner as in Example 6 (Step 2) except that Compound 19 used in Example 6 (Step 2) was replaced by Compound 51, title Compound 52 (775 mg, 2.15 mmol) was obtained from Compound 51 (1.17 g, 2.40 mmol) as a white viscous liquid (yield 89%).

1H-NMR (500 MHz, DMSO-d6, δ) 1.23-1.31 (9H, m, CH3, CH2×3), 1.49-1.60 (4H, m, CH2×2), 2.16-2.21 (2H, m, CH2), 2.29 (2H, t, J=8 Hz, CH2), 2.72 (2H, m, CH2), 4.02-4.05 (1H, m, CH), 4.12-4.23 (4H, m, CH2×2), 8.15 (3H, brs, NH3), 8.82 (3H, brs, NH3)

ESI-MS: Calcd for C14H28N2O4 [M+H]+, 289.2; found 289.2.

Example 17

Preparation of Chondroitin Sulfate Crosslinked with Compound 7 (CS-GlySerEt)

(Method A)

1.70 g (3.33 mmol in terms of carboxyl groups, 1.00 eq) of CS (sodium salt, The Japanese Pharmaceutical Codex, manufactured by SEIKAGAKU CORPORATION) was dissolved into water for injection (WFI) so that its concentration would be 10%, and ethanol (EtOH) 17.0 ml was mixed therewith. A 50% (v/v) aqueous ethanol solution (1.70 mL) of Compound 7 (36.8 mg, 0.042 eq) (a diamine crosslinking agent) synthesized in Example 2, and a 50% (v/v) ethanol solution (1.70 mL) of 4-(4,6-dimethoxy-1,3,5-triazin-2-yl)-4-methylmorpholinium chloride.N hydrate (DMT-MM) (232 mg, 0.252 eq: 6-fold relative to the diamine crosslinking agent) were sequentially added. The mixture was stirred at room temperature for 10 minutes and was allowed to stand overnight.

WFI (225 mL) was added to the crosslinking reaction product resulting from the overnight standing, and the mixture was stirred vigorously for 4 hours to crush the solidified reaction product. A sodium chloride (NaCl) solution (1.50 g/6.00 mL) was added, and EtOH was added dropwise to cause precipitation. The precipitate was collected by filtration, and was washed with 90% (v/v) EtOH 150 mL three times and with EtOH 150 mL two times. The resultant precipitate was vacuum dried at 42° C. overnight. In this manner, chondroitin sulfate crosslinked with Compound 7 (CS-GlySerEt) (1.45 g) was obtained as a white powder.

(Method B: Preparation of Analogues)

By a method similar to that of Example 17 (Method A) except that the equivalent of Compound 7 was changed (0.030, 0.031, 0.034, 0.050 or 0.060 eq), several types of crosslinked CSs (CS-GlySerEt) were obtained each as a white powder (in each case approximately 1.40 g).

Example 18

Preparation of Chondroitin Sulfate Crosslinked with Compound 10 (CS-GlySerNH2)

In substantially the same manner as in Example 17 (Method A) except that Compound 7 used in Example 17 (Method A) was replaced by Compound 10 (synthesized in Example 3), the equivalent of Compound 10 was changed (0.030, 0.040, 0.050 or 0.060 eq), the amount of CS was changed to 1.64 g and the initial CS concentration was changed to 20.5%, several types of crosslinked CSs (CS-GlySerNH2) were obtained each as a white powder (in each case approximately 1.00 g).

(Calculation of Crosslinking Ratio)

The crosslinking ratio of each of the obtained crosslinked CSs (CS-GlySerNH2) was calculated as defined in formula (A) below:

[Math. 2]

$$\frac{\text{Molar equivalent of the diamine crosslinking agent whose amino groups at both ends are bonded to the acidic polysaccharide (mol)}}{\text{Total molar equivalend of -COR groups in the crosslinked acidic polysaccharide (mol)}} \times 100(\%) \quad (A)$$

(wherein R indicates —OH, —ONa, or NH crosslinking agent.)

From the results given in the table below, it was shown that the crosslinking ratio was correlated with (i.e., increased depending on) the equivalent of the diamine crosslinking agent fed.

TABLE 1

|  | Equivalent (eq) of diamine crosslinking agent (per 1.00 eq. of carboxyl groups) | | | |
| --- | --- | --- | --- | --- |
|  | 0.03 | 0.04 | 0.05 | 0.06 |
| Crosslinking ratio (%) | 0.84 | 1.80 | 2.37 | 2.64 |

Example 19

Preparation of Chondroitin Sulfate Crosslinked with Compound 4 (CS-GlyC2N)

In substantially the same manner as in Example 17 (Method A) except that Compound 7 used in Example 17 (Method A) was replaced by Compound 4 (synthesized in Example 1), the equivalent of Compound 4 was changed (0.015, 0.019, 0.023, 0.027 or 0.035 eq) and the amount of CS was changed to 1.00 g, several types of crosslinked CSs (CS-GlyC2N) were obtained each as a white powder (in each case approximately 0.6 g).

Example 20

Preparation of Chondroitin Sulfate Crosslinked with Compound 10 (CS-GlySerNH2)

In substantially the same manner as in Example 17 (Method A) except that Compound 7 used in Example 17 (Method A) was replaced by Compound 10 (synthesized in Example 3), the equivalent of Compound 10 was changed (0.030, 0.033, 0.036, 0.040, 0.042, 0.045 or 0.048 eq) and the amount of CS was changed to 1.70 g, several types of crosslinked CSs (CS-GlySerNH2) were obtained each as a white powder (in each case approximately 1.50 g).

Example 21

Preparation of Chondroitin Sulfate Crosslinked with Compound 14 (CS-GlySerNHMe)

In substantially the same manner as in Example 17 (Method A) except that Compound 7 used in Example 17 (Method A) was replaced by Compound 14 (synthesized in Example 4) and the equivalent of Compound 14 was changed (0.030, 0.035, 0.040, 0.045 or 0.050 eq), several types of crosslinked CSs (CS-GlySerNHMe) were obtained each as a white powder (in each case approximately 1.50 g).

Example 22

Preparation of Chondroitin Sulfate Crosslinked with Compound 17 (CS-GlySerNMe2)

In substantially the same manner as in Example 17 (Method A) except that Compound 7 used in Example 17 (Method A) was replaced by Compound 17 (synthesized in Example 5) and the equivalent of Compound 17 was changed (0.030, 0.035, 0.040, 0.045 or 0.050 eq), several types of crosslinked CSs (CS-GlySerNMe2) were obtained as a white powder (in each case approximately 1.50 g).

Example 23

Preparation of Chondroitin Sulfate Crosslinked with Compound 20 (CS-GlyHomoSerEt)

In substantially the same manner as in Example 17 (Method A) except that Compound 7 used in Example 17 (Method A) was replaced by Compound 20 (synthesized in Example 6) and the equivalent of Compound 20 was changed (0.016, 0.019, 0.028 or 0.038 eq), several types of crosslinked CSs (CS-GlyHomoSerEt) were obtained as a white powder (in each case approximately 1.50 g).

Example 24

Preparation of Chondroitin Sulfate Crosslinked with Compound 24 (CS-AlaC2MeN)

In substantially the same manner as in Example 17 (Method A) except that Compound 7 used in Example 17 (Method A) was replaced by Compound 24 (synthesized in Example 7) and the equivalent of Compound 24 was changed (0.028, 0.033, 0.036, 0.042 or 0.054 eq), several types of crosslinked CSs (CS-AlaC2MeN) were obtained as a white powder (in each case approximately 1.50 g).

Example 25

Preparation of Chondroitin Sulfate Crosslinked with Compound 27 (CS-AlaC2Me2N)

In substantially the same manner as in Example 17 (Method A) except that Compound 7 used in Example 17 (Method A) was replaced by Compound 27 (synthesized in Example 8) and the equivalent of Compound 27 was changed (0.046, 0.054, 0.058 or 0.062 eq), several types of crosslinked CSs (CS-AlaC2Me2N) were obtained as a white powder (in each case approximately 1.50 g).

Example 26

Preparation of Hyaluronic Acid Crosslinked with Compound 10 (HA-GlySerNH2)

(Method C)
1.00 g (2.49 mmol in terms of carboxyl groups, 1.00 eq) of sodium hyaluronate (hereinafter, HA) (manufactured by SEIKAGAKU CORPORATION) was dissolved into WFI so that its concentration would be 2.34 wt %, and ethanol 42.7 mL was mixed therewith. Compound 10 (synthesized in Example 3) (55.5 mg, 0.095 eq) and DMT-MM (394 mg, 0.571 eq: 6-fold relative to the diamine crosslinking agent) were each dissolved into a 50% (v/v) aqueous EtOH solution (total 7.10 mL), and the respective solutions were added sequentially. The mixture was stirred at room temperature for 10 minutes, and was allowed to stand overnight.

WFI (50 mL) and NaCl/WFI solution (1.00 g/4.00 mL) were added to the crosslinking reaction product resulting from the overnight standing, and the mixture was stirred vigorously for 4 hours to crush the solidified reaction product. The subsequent operations were substantially the same as those in the method described in Example 17 (Method A). In this manner, a crosslinked hyaluronic acid (HA-GlySerNH2) (1.02 g) was obtained as a white powder.

(Method D: Preparation of Analogues)
By substantially the same method as in Example 26 (Method C) except that the equivalent of Compound 10 was changed to (0.151 or 0.190 eq), crosslinked HAs (HA-GlySerNH2) were obtained each as a white powder (in each case approximately 1.00 g).

Example 27

Preparation of Hyaluronic Acid Crosslinked with Compound 24 (HA-AlaC2MeN)

In substantially the same manner as in Example 26 (Method C) except that Compound 10 used in Example 26 (Method C) was replaced by Compound 24 (synthesized in Example 7) and the equivalent of Compound 24 was changed (0.095, 0.151 or 0.190 eq), several types of crosslinked HAs (HA-AlaC2MeN) were obtained each as a white powder (in each case approximately 1.00 g).

Example 28

Preparation of Carboxymethyl Cellulose Crosslinked with Compound 10 (CMC-GlySerNH2)

(Method E)
In substantially the same manner as in Example 26 (Method C) except that HA used in Example 26 (Method C)

was replaced by carboxymethyl cellulose sodium [number of Glc recurring units≈500] (hereinafter, CMC) (manufactured by Tokyo Chemical Industry Co., Ltd.), the initial amount of CMC was 1.11 g (2.52 mmol in terms of carboxyl groups, 1.00 eq), the CMC concentration was 2.32 wt % and the amount of EtOH added was 32 mL, using Compound 10 (synthesized in Example 3) (0.168, 0.224 or 0.280 eq), crosslinked CMCs (CMC-GlySerNH2) were obtained each as a white powder (in each case approximately 0.95 g).

Example 29

Preparation of Carboxymethyl Cellulose Crosslinked with Compound 24 (CMC-AlaC2MeN)

In substantially the same manner as in Example 28 (Method E) except that Compound 10 used in Example 28 (Method E) was replaced by Compound 24 (synthesized in Example 7), the amount of CMC was changed to 0.56 g and the equivalent of Compound 24 was changed (0.180, 0.240 or 0.300 eq), several types of crosslinked CMCs (CMC-AlaC2MeN) were obtained each as a white powder (in each case approximately 0.47 g).

Example 30

Preparation of Alginic Acid Crosslinked with Compound 10 (Alg-GlySerNH2)

(Method F)
In substantially the same manner as in Example 26 (Method C) except that HA used in Example 26 (Method C) was replaced by sodium alginate [viscosity: 500 to 600 mPa·s] (hereinafter, Alg) (manufactured by Wako Pure Chemical Industries, Ltd.), the initial amount of Alg was 1.08 g (5.46 mmol in terms of carboxyl groups, 1.00 eq), the Alg concentration was 1.23 wt % and the amount of EtOH added was 29.3 mL, using Compound 10 (synthesized in Example 3) (0.123, 0.146 or 0.168 eq), crosslinked Algs (Alg-GlySerNH2) were obtained each as a white powder (in each case approximately 0.95 g).

Example 31

Preparation of Alginic Acid Crosslinked with Compound 24 (Alg-AlaC2MeN)

In substantially the same manner as in Example 30 (Method F) except that Compound 10 used in Example 30 (Method F) was replaced by Compound 24 (synthesized in Example 7), the amount of CMC was changed to 0.54 g and the equivalent of Compound 24 was changed (0.123, 0.146 or 0.168 eq) several types of crosslinked Algs (Alg-AlaC2MeN) were obtained each as a white powder (in each case approximately 0.46 g).

Comparative Example 1

Preparation of Chondroitin Sulfate Crosslinked with Ethane-1,2-diamine.dihydrochloride (CS-NC2N)

The procedures in Example 17 (Method A) were repeated, except that Compound 7 used in Example 17 (Method A) was replaced by ethane-1,2-diamine (NC2N).dihydrochloride, the equivalent of ethane-1,2-diamine.dihydrochloride was 0.022 or 0.030 eq, the equivalent of DMT-MM was 0.132 or 0.120 eq and the amount of CS was changed to 1.70 or 5.00 g. In this manner, crosslinked CSs (CS-NC2N) were obtained each as a white powder (1.50 g and 4.85 g, respectively).

Comparative Example 2

Preparation of Hyaluronic Acid Crosslinked with Ethane-1,2-diamine.dihydrochloride (HA-NC2N)

In substantially the same manner as in Example 26 (Method C) except that Compound 10 used in Example 26 (Method C) was replaced by ethane-1,2-diamine.dihydrochloride and the equivalent of ethane-1,2-diamine.dihydrochloride was changed (0.085, 0.135 or 0.170 eq), several types of crosslinked HAs (HA-NC2N) were obtained each as a white powder (in each case approximately 1.00 g).

Comparative Example 3

Preparation of Carboxymethyl Cellulose Crosslinked with Ethane-1,2-diamine.dihydrochloride (CMC-NC2N)

In substantially the same manner as in Example 28 (Method E) except that Compound 10 used in Example 28 (Method E) was replaced by ethane-1,2-diamine.dihydrochloride, the amount of CMC was changed to 0.56 g and the equivalent of ethane-1,2-diamine.dihydrochloride was changed (0.150, 0.200 or 0.250 eq), several types of crosslinked CMCs (CMC-NC2N) were obtained each as a white powder (in each case approximately 0.45 g).

Comparative Example 4

Preparation of Alginic Acid Crosslinked with Ethane-1,2-diamine.dihydrochloride (Alg-NC2N)

In substantially the same manner as in Example 30 (Method F) except that Compound 10 used in Example 30 (Method F) was replaced by ethane-1,2-diamine.dihydrochloride, the amount of Alg was changed to 0.54 g and the equivalent of ethane-1,2-diamine.dihydrochloride was changed (0.110, 0.130 or 0.150 eq), several types of crosslinked Algs (Alg-NC2N) were obtained as a white powder (in each case approximately 0.42 g).

Example 32

Changes with Time in Viscosity of Swollen Crosslinked CSs (CS-GlyC2N/AlaC2MeN/AlaC2Me2N/NC2N) (In Vitro Test)

20 mM phosphate buffered physiological saline was added to each of the white powders of CS-GlyC2N, CS-AlaC2MeN and CS-AlaC2Me2N prepared in Examples 19, 24 and 25, and of CS-NC2N (control) prepared in Comparative Example 1, to thereby obtain swollen crosslinked CSs as jelly-like materials. Using these materials, evaluations were made to determine whether or not the disintegration time of the swollen crosslinked CS was controllable (i.e., capability of disintegration after the period of time required as a tissue bulking material). The concentration of the swollen material was 1.75%, and the pH was near the biological conditions at 7.5. To accelerate the rate of change, the swollen materials were allowed to stand at a temperature of 60° C., and the changes with time in viscosity of the swollen materials were measured. Viscosity of such a material is associated with the persistence of the material in living tissues, and it is known that the decrease in viscosity of the material to a certain value or less allows the material to disappear quickly from the site of administration. For example, it is confirmed that non-crosslinked original CS, having a viscosity of about −5 (LN(Pa·s)), is quickly disintegrated from a living body within several hours. Thus, the viscosity of non-crosslinked CS can serve as an index of persistence. Further, as described below in detail, the results of this in vitro test have been confirmed to be correlated with the results of the in vivo test described in Example 37.

The viscosity was measured with a cone-plate rotatory viscometer TV-L (cone: CORD-1, 1°34'×R24, or CORD-6, 3°×R9.7) (manufactured by TOKI SANGYO CO., LTD.). The value of viscosity (Pa·s) measured at 25° C. and 5 rpm was adopted.

The results are illustrated in FIG. 1. The values in parenthesis described in the legends in FIG. 1 represent the equivalent of the diamine crosslinking agent that was fed. In the case of the crosslinked CS with ethane-1,2-diamine.dihydrochloride having no biodegradable sites (CS-NC2N), any decrease in viscosity meaning disappearance from living tissues (degradation of crosslinks) was not observed. In contrast, crosslinked CSs each prepared with the diamine crosslinking agent having an ester bond as a biodegradable site, namely, CS-GlyC2N, CS-AlaC2MeN and CS-AlaC2Me2N, have been shown to be suitable as medical materials each having a controllable disintegration time of from several days to several months.

Example 33

Changes with Time in Viscosity of Swollen Crosslinked HAs
(HA-GlySerNH2/AlaC2MeN/NC2N) (In Vitro Test)

Figure 2:
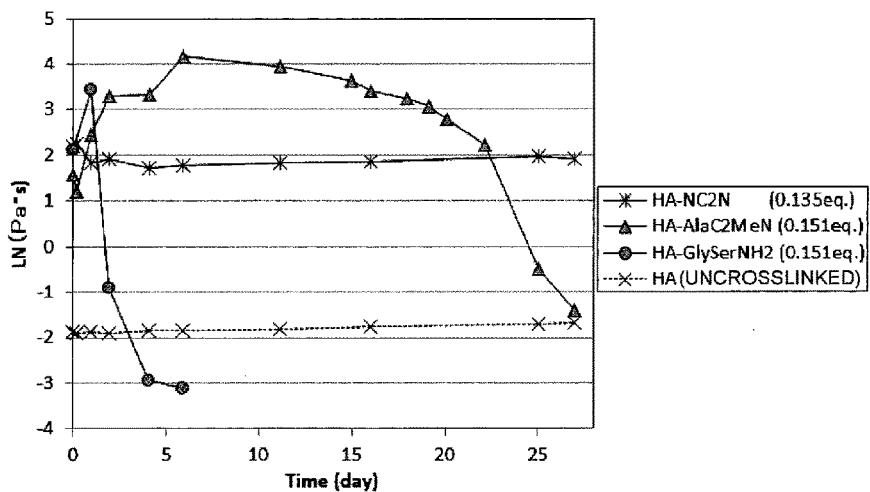
FIG. 2 is a diagram illustrating changes in the viscosity of swollen crosslinked HA materials (HA-GlySerNH2/A1aC2MeN/NC2N) with time.

To evaluate the capability of disintegration after the period of time required as a tissue bulking material, HA-GlySerNH2 and HA-AlaC2MeN prepared in Examples 26 and 27 were tested, in a swollen form, to measure changes with time in viscosity. The conditions were similar to those in the method described in Example 32 except that the pH of the liquid for swelling was 9.0 and the temperature was 50° C. to accelerate the test. As controls, HA-NC2N prepared in Comparative Example 2, and the original HA (non-crosslinked) were used. The results are illustrated in FIG. 2. The values in parenthesis described in the legends in FIG. 2 represent the equivalent of the diamine crosslinking agent that was fed.

Similarly to the results of Example 32, the HA crosslinked with ethane-1,2-diamine.dihydrochloride having no biodegradable sites (HA-NC2N) did not show any decrease in viscosity meaning disintegration from living tissues (degradation of crosslinks). In contrast, the crosslinked HAs prepared with the diamine crosslinking agent having a biodegradable site, namely, HA-GlySerNH2 and HA-AlaC2MeN, have been demonstrated to have a marked difference in disintegration time ascribed to the stability of their ester structures. Because the original HA (non-crosslinked) did not substantially change its viscosity, it has been confirmed that the change in viscosity observed in the crosslinked HAs was dependent on the degradation of the diamine crosslinking agent. Thus, it has been demonstrated that by the use of the diamine having a biodegradable site, it becomes possible to prepare, also from HA, a crosslinked product suitable as a medical material having a controllable disintegration time of from several days to several months in a living body.

Further, the results of this example have shown that the tendency of disintegration of the crosslinked acidic polysaccharides can be confirmed even when the pH of the swollen materials is increased to above the biological pH conditions.

Example 34

Changes in Viscosity of Swollen Crosslinked CMC Materials (CMC-GlySerNH2/AlaC2MeN/NC2N) with Time (In Vitro Test)

Figure 3:
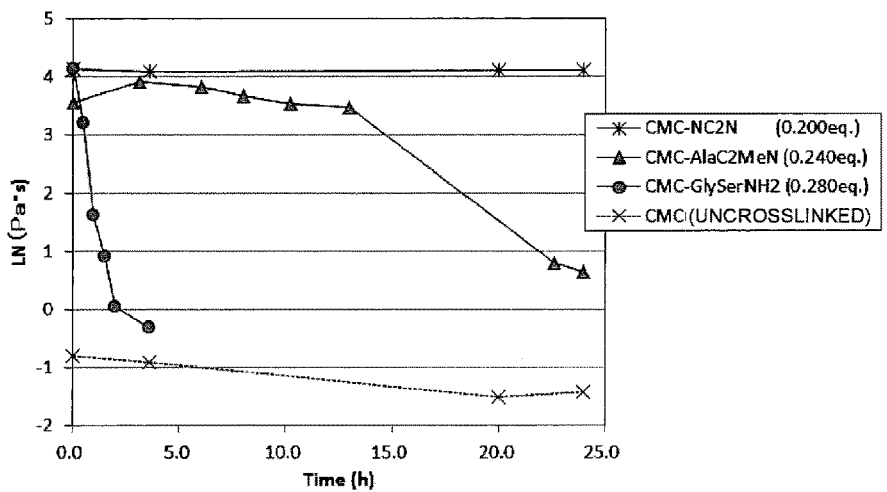
FIG. 3 is a diagram illustrating changes in the viscosity of swollen crosslinked CMC materials (CMC-GlySerNH2/A1aC2MeN/NC2N) with time.

To evaluate the capability of disintegration after the period of time required as a tissue bulking material, CMC-GlySerNH2 and CMC-AlaC2MeN prepared in Example 28 and 29 were tested, in a swollen form, to measure changes with time in viscosity. The conditions were similar to those in the method described in Example 33 except that the pH of the liquid for swelling was 11.0 to accelerate the test. As controls, CMC-NC2N prepared in Comparative Example 3 and the original CMC (non-crosslinked) were used. The results are illustrated in FIG. 3. The values in parenthesis described in the legends in FIG. 3 represent the equivalent of the diamine crosslinking agent that was fed.

During the test period, no significant decrease in viscosity was observed in CMC crosslinked with ethane-1,2-diamine.dihydrochloride having no biodegradable sites (CMC-NC2N) and in the original CMC (non-crosslinked). In contrast, similarly to the results in Examples 32 and 33, CMC-GlySerNH2 and CMC-AlaC2MeN prepared with the diamine crosslinking agent having a biodegradable site showed a decrease in viscosity meaning disappearance from living tissues (degradation of crosslinks), and they had a marked difference in disintegration time ascribed to their ester structures. Thus, it has been demonstrated that by the use of the diamine crosslinking agent having a biodegradable site, it becomes possible to prepare, also from CMC, a crosslinked product suitable as a medical material having a controllable disintegration time of from several days to several months in a living body.

Example 35

Changes with Time in Viscosity of Swollen Crosslinked Algs
(Alg-GlySerNH2/AlaC2MeN/NC2N) (In Vitro Test)

Figure 4:
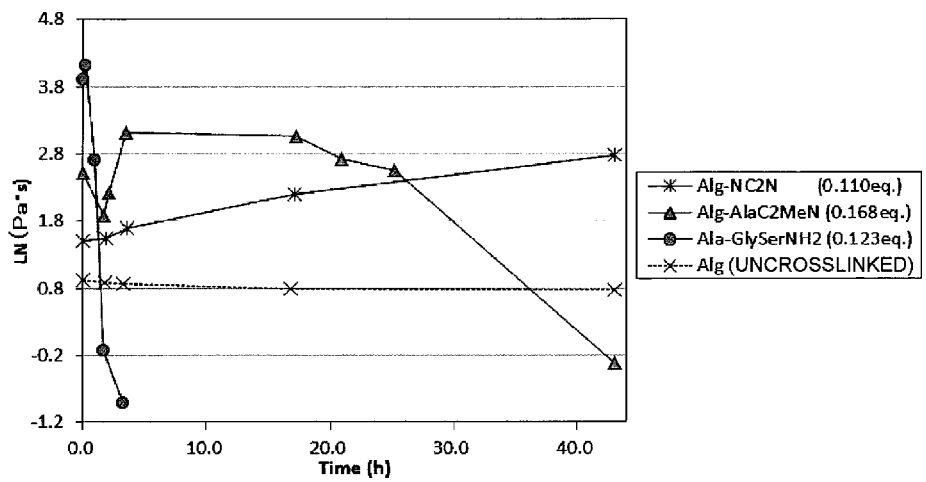
FIG. 4 is a diagram illustrating changes in the viscosity of swollen crosslinked Alg materials (Alg-GlySerNH2/AlaC2MeN/NC2N) with time.

To evaluate the capability of disintegration after the period of time required as a tissue bulking material, Alg-GlySerNH2 and Alg-AlaC2MeN prepared in Examples 30 and 31 were tested, in a swollen form, by the same method as in Example 34 to measure changes with time in viscosity. As controls, Alg-NC2N prepared in Comparative Example 4 and the original Alg (non-crosslinked) were used. The results are illustrated in FIG. 4. The values in parenthesis described in the legends in FIG. 4 represent the equivalent of the diamine crosslinking agent that was fed.

During the test period, no significant decrease in viscosity was observed in Alg crosslinked with ethane-1,2-diamine.dihydrochloride having no biodegradable sites (Alg-NC2N) and in the original Alg (non-crosslinked). In contrast, similarly to the results in Examples 32, 33 and 34, the crosslinked Algs prepared with the diamine crosslinking agent having a biodegradable site, namely, Alg-GlySerNH2 and Alg-AlaC2MeN, showed a decrease in viscosity meaning disappearance from living tissues (degradation of crosslinks), and they had a marked difference in disintegration time ascribed to their ester structures. Thus, it has been demonstrated that by the use of the diamine crosslinking agent having a biodegradable site, it becomes possible to prepare, also from alginic acid, a crosslinked product suitable as a medical material having a controllable disintegration time of from several days to several months in a living body.

Example 36

Measurement of Physical Stress of Crosslinked CS Products

In this test, swollen crosslinked CS materials were tested to measure the physical stress for separating tissues from each other that is required in use as tissue bulking materials.

Prior to the testing, the products were subjected to a swelling/disintegration test with saline as described later in Example 38, and the equilibrium swelling concentration of each crosslinked CS product is calculated from the weight of the swollen materials after 3 days.

Figure 5:
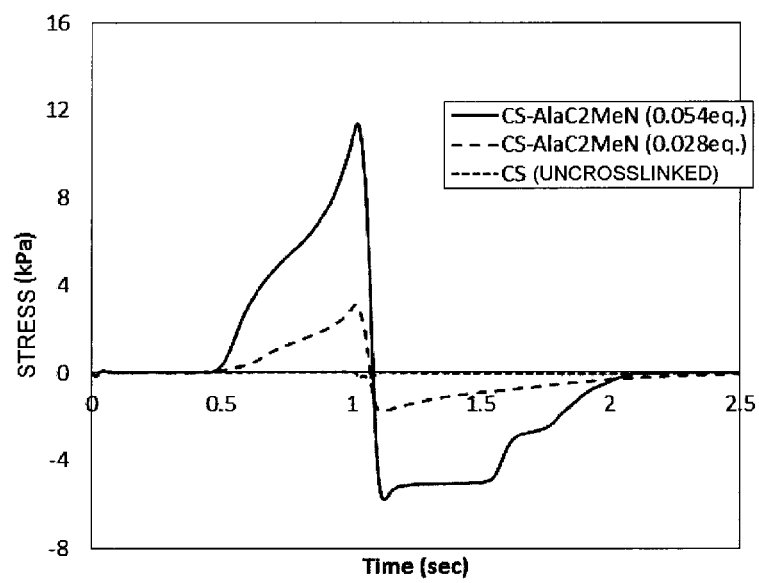
FIG. 5 is a diagram illustrating the physical stress of swollen crosslinked CS materials.

The crosslinked CS products (CS-AlaC2MeN) prepared in Example 24 were swollen with saline so that the concentration would be 1.5 times the equilibrium swelling concentration, and 1 g of the swollen material was packed into a cylindrical container having a bottom area of 3.8 cm$^2$ so that the surface would be flat. A relationship between strain and stress was studied in accordance with the method described in JIS K6503, Animal glues and gelatins (5.4 Jelly strength) except that the insertion rate was 4 mm/sec, the diameter of the cylindrical probe was 10 mm, and the probe was inserted to 5 mm above the bottom and was returned to the start point. The results are described in Table 2 and FIG. 5. The values in parenthesis described in the legends in FIG. 5 represent the equivalent of the diamine crosslinking agent that was fed.

CS-AlaC2MeN crosslinked with the diamine crosslinking agent exhibited a markedly higher stress than the uncrosslinked raw material CS. Further, it has been shown that the optimum physical stress for use as tissue bulking materials in medical applications can be controlled by controlling the equivalent of the crosslinking agent.

TABLE 2

| Test sample | Preparation | Concentration (wt %)/saline | Equivalent of diamine crosslinking agent (eq) | Maximum stress (kPa) |
|---|---|---|---|---|
| CS | Uncrosslinked | 3.00 | — | 0.09 |
| CS-AlaC2MeN | Example 24 | 2.24 | 0.028 | 3.11 |
| CS-AlaC2MeN | Example 24 | 3.00 | 0.054 | 11.39 |

Example 37

Evaluation of Persisting Performance of Crosslinked CS Products (CS-GlySerEt/GlyC2N/AlaC2MeN/AlaC2Me2N) Under Abdominal Skin of Rats (In Vivo Test)

The persisting performance of swollen crosslinked CS materials under the abdominal skin of rats was evaluated by the following method.

(1) Under isoflurane anesthesia, male Wistar rats (7 week old) were subcutaneously injected at the abdominal with 400 μL/site of the test substance having the equilibrium swelling concentration.

(2) After a prescribed period after the injection, tissues around the residue were collected and the residue was separated. The weight thereof was measured as the indicator of persisting performance. (The residual weight percentage (%) under the abdominal skin of rats relative to the injected weight as 100%)

(3) The crosslinked CS products prepared in Examples 17, 19, 24 and 25 were used in the test. As a control, crosslinked CS (CS-NC2N) prepared in Comparative Example 1 was used.

(4) Prior to the testing, each of the crosslinked CS products was subjected to a swelling/disintegration test with saline as described later in Example 38. After 3 days, the weight of the swollen material was measured to calculate the equilibrium swelling concentration. The crosslinked CS products were each swollen with a pH 5.2 buffer solution to the equilibrium swelling concentration, thereby preparing samples used in the test.

Figure 6:
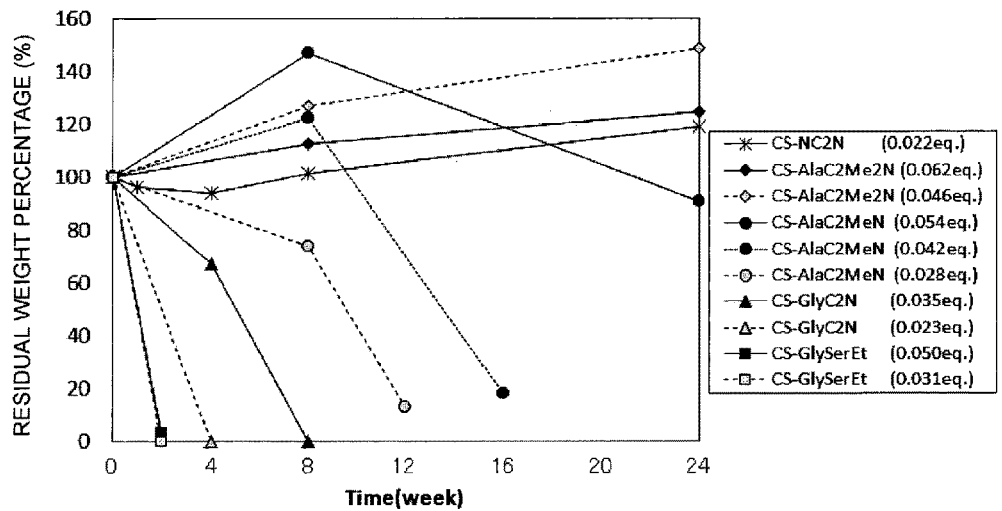
FIG. 6 is a diagram illustrating evaluations of the persisting performance of crosslinked CS products (CS-GlySerEt/GlyC2N/AlaC2MeN/A1aC2Me2N) under the abdominal skin of rats.

As illustrated in FIG. 6, the results have shown that the swollen materials of the crosslinked CS products produced with the various diamine crosslinking agents having a biodegradable site persisted in the living bodies for various durations of time ranging from 2 weeks to 24 weeks or up to about one year. The values in parenthesis described in the legends in FIG. 6 represent the equivalent of the diamine crosslinking agent that was fed. The results were highly correlated with the results of the in vitro test (changes in viscosity with time) described in Example 32. As discussed above, the crosslinked acidic polysaccharides prepared with the diamine crosslinking agent having a biodegradable site are highly useful as tissue bulking materials which exhibit high biocompatibility and have a persisting time precisely controllable in accordance with the administration site or the purpose of use.

Example 38

Swelling/Disintegration Test (In Vitro) of Crosslinked CS Products (CS-GlySerNH2)

Ideal adhesion preventing materials are demanded not only to have high antiadhesive performance but also to be disintegrated quickly after a prescribed period has passed. In this series of testing, the property of swelling by absorbing water through a filter represents the antiadhesive performance that isolates a wound, and the reduction in weight by flowing out of the material through a filter represents the disintegration performance in living bodies.

Figure 7:
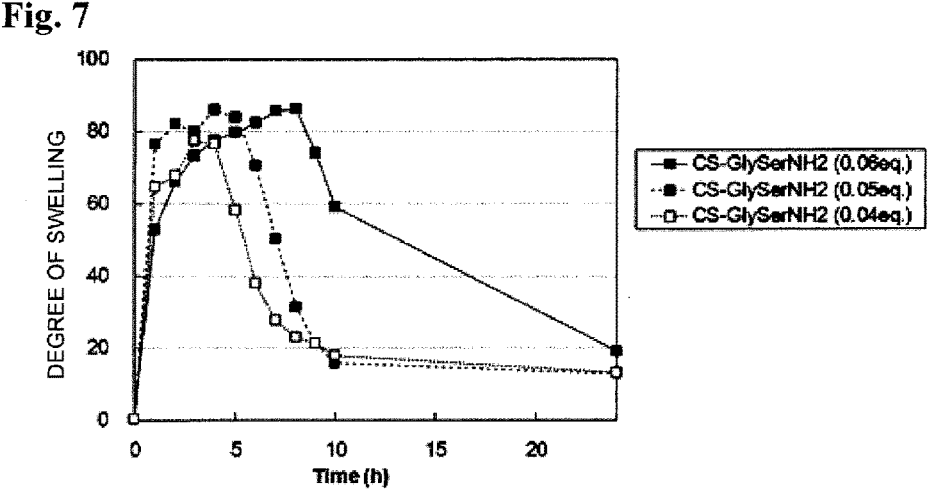
FIG. 7 is a diagram illustrating the results of a swelling/disintegration test with respect to crosslinked CS products (CS-GlySerNH2).

Specifically, the test involved a 0.22 μm filter, and a buffer solution (pH 10.9) to perform the test under accelerated biological conditions. The total weight (mg) of the swollen material per 1 mg of the test sample powder was defined as the degree of swelling, and changes in the degree of swelling with time were plotted on the ordinate.
(Test Samples)
The crosslinked CS products (CS-GlySerNH2) prepared in Example 18 were used.
(Results)
The results of the test are illustrated in FIG. 7. The values in parenthesis described in the legends in FIG. 7 represent the equivalent of the diamine crosslinking agent that was fed. As illustrated in FIG. 7, CS-GlySerNH2 crosslinked with GlySerNH2 showed rapid swelling and quick disintegration at any equivalent. The results were very highly correlated with the antiadhesive performance/disintegration performance in vivo described in Example 42. Thus, it has been shown that crosslinked products having a pattern of weight change similar to the weight change pattern in FIG. 7 obtained in this series of testing will exhibit antiadhesive performance/disintegration performance also in vivo.

Example 39

Swelling/Disintegration Test (In Vitro) of Crosslinked HA Products (HA-GlySerNH2)

Figure 8:
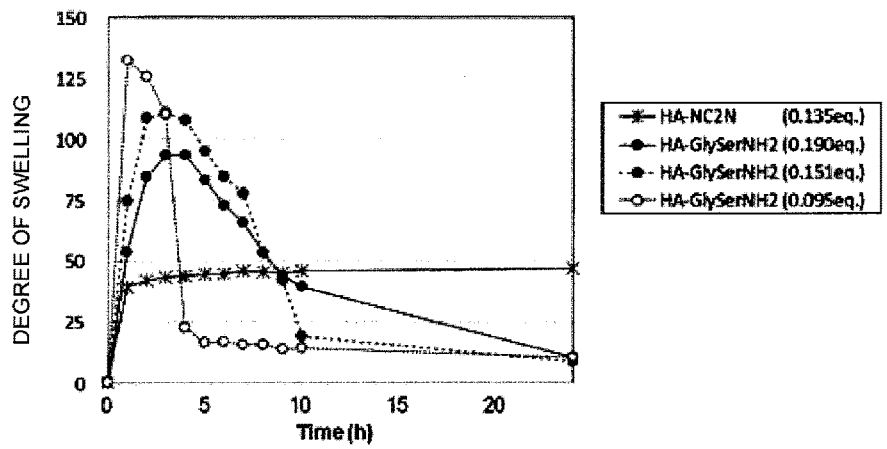
FIG. 8 is a diagram illustrating the results of a swelling/disintegration test with respect to crosslinked HA products (HA-GlySerNH2).

(Test Method)
The test was performed by a method similar to that described in Example 38.
(Test Samples)
The crosslinked HA products (HA-GlySerNH2 and HA-NC2N) prepared in Example 26 and Comparative Example 2 were used.
(Results)
The results of the test are illustrated in FIG. 8. The values in parenthesis described in the legends in FIG. 8 represent the equivalent of the diamine crosslinking agent that was fed. As illustrated in FIG. 8, HA-GlySerNH2 exhibited swelling/disintegration characteristics similar to those in Example 38, and were thus shown to be useful as adhesion preventing materials. The crosslinked HA product (HA-NC2N) prepared with ethane-1,2-diamine.dihydrochloride having no biodegradable sites was swollen but did not show any disintegration by the decomposition of the diamine crosslinking agent. The results of this test were very highly correlated with the antiadhesive performance/disintegration performance in vivo described in Example 42. Thus, it has been shown that the biodegradable site in the structure of the diamine crosslinking agent plays a very important role in controlling the disintegration performance appropriately.

Example 40

Swelling/Disintegration Test (In Vitro) of Crosslinked CMC Products (CMC-GlySerNH2)

Figure 9:
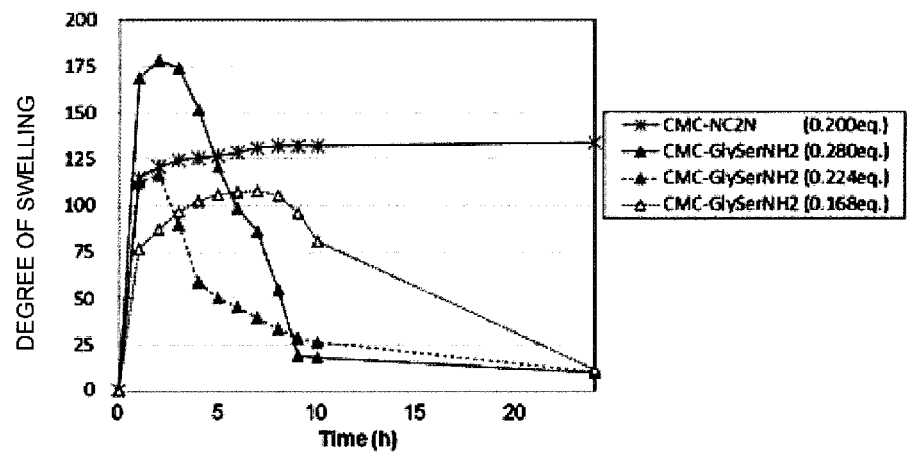
FIG. 9 is a diagram illustrating the results of a swelling/disintegration test with respect to crosslinked CMC products (CMC-GlySerNH2).

(Test Method)
The test was performed by a method similar to that described in Example 38.
(Test Samples)
CMC-GlySerNH2 and CMC-NC2N prepared in Example 28 and Comparative Example 3 were used.
(Results)
The results of the test are illustrated in FIG. 9. The values in parenthesis described in the legends in FIG. 9 represent the equivalent of the diamine crosslinking agent that was fed. As illustrated in FIG. 9, CMC-GlySerNH2 exhibited swelling/disintegration characteristics similar to those in Example 38, and were thus shown to be useful as adhesion preventing materials. The crosslinked CMC product (CMC-NC2N) prepared with ethane-1,2-diamine.dihydrochloride having no biodegradable sites showed results similar to those obtained in Example 39.

Example 41

Swelling/Disintegration Test (In Vitro) of Crosslinked Alg Products (Alg-GlySerNH2)

(Test Method)
The test was performed by a method similar to that described in Example 38.
(Test Samples)
Alg-GlySerNH2 and Alg-NC2N prepared in Example 30 and Comparative Example 4 were used.

Figure 10:
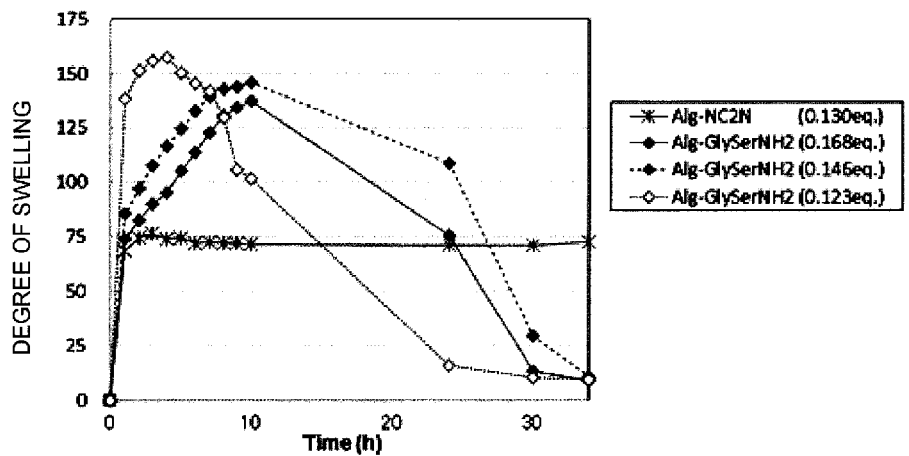
FIG. 10 is a diagram illustrating the results of a swelling/disintegration test with respect to crosslinked Alg products (Alg-GlySerNH2).

(Results)
The results of the test are illustrated in FIG. 10. The values in parenthesis described in the legends in FIG. 10 represent the equivalent of the diamine crosslinking agent that was fed. As illustrated in FIG. 10, Alg-GlySerNH2 exhibited swelling/disintegration characteristics similar to those in Example 38, and were thus shown to be useful as adhesion preventing materials. The crosslinked Alg product (Alg-NC2N) prepared with ethane-1,2-diamine.dihydrochloride having no biodegradable sites showed results similar to those obtained in Example 39.

Example 42

Test of Antiadhesive Performance/Disintegration Performance (In Vivo) of Crosslinked CS Products in Rat Uterine Horn Adhesion Models (1. Test Animals)
Crl:CD (SD) (SPF) female rats purchased at the age of 7 weeks were used in the test after being preliminarily fed for 1 week before the test. Five individuals were used per test substance.
(2. Test Method)
(2-1. Preparation of Rat Uterine Horn Adhesion Models)
Under isoflurane inhalation anesthesia (concentration 3%, flow rate 2 to 3 L/min), the abdominal of the rats was shaved and was disinfected with alcohol. Thereafter, an approximately 4 cm midline incision was made. The right abdominal wall musculature of the rat was exposed. With an 8 mm diameter trepan for corneal transplant, a circular incision was made at approximately 1.5 cm from the midline incision toward the back. The musculature inside the circular incision was removed with tweezers, and a circular defective layer was thus prepared. Subsequently, the right uterine horn was exposed. With ophthalmic scissors, four incisional wounds were created at intervals of 2 to 3 mm from approximately 1 cm aside the ovary toward the uterine cervix. Bleeding from the wounds was arrested as needed with an electrocautery. In order to promote the formation of strong adhesions, both of the two ends of the uterine horn were stitched to the abdominal wall by one stitch of 8/0 suture thread so that the defective wound on the abdominal wall would adjoin to the incisional wounds on the uterine horn.
[Test Samples]:
Test samples were prepared by interposing the powder of the crosslinked acidic polysaccharide or the powder of the uncrosslinked acidic polysaccharide, each 25 mg/site, and commercial Seprafilm (1×3 cm) between the defect in the abdominal wall and the incisional wounds in the uterine horn.
[Controls]:
Controls were prepared by surgically operating the left abdominal wall and the left uterine horn of the animals used in the preparation of the test samples in the same manner but without interposing any materials.
(3. Evaluation Method)
Seven days after the implant, the rats were slaughtered by exsanguination from the carotid artery under ether anesthesia, and were dissected. The antiadhesive effects of the candidate substances were evaluated based on the rate of the occurrence of adhesions. Here, the antiadhesive effects were determined as the ratio of the individuals with adhesions to the individuals administered with the test substance (the five individuals). After the completion of the test, the concentration of the test substance in the abdominal cavity was measured by a carbazole sulfate method and was compared to that in the control. The disintegratability of the test substances was evaluated as "Disappeared" when the test substance administered was not substantially detected, and as "Remained" when a distinct amount of the test substance was detected.

(4. Results)

The results of the test are described in Table 3.

TABLE 3

| Ex. | Test substance | Equivalent weight (eq) | Antiadhesive effects | | Disintegratability |
|---|---|---|---|---|---|
| | | | Test samples | Controls | |
| 17 | CS-GlySerEt | 0.034 | 0/5 | 5/5 | Disappeared |
| 17 | CS-GlySerEt | 0.042 | 1/5 | 5/5 | Disappeared |
| 17 | CS-GlySerEt | 0.050 | 0/5 | 5/5 | Disappeared |
| 17 | CS-GlySerEt | 0.060 | 0/5 | 5/5 | Disappeared |
| 19 | CS-GlyC2N | 0.023 | 0/5 | 5/5 | Disappeared |
| 20 | CS-GlySerNH2 | 0.033 | 0/5 | 5/5 | Disappeared |
| 20 | CS-GlySerNH2 | 0.036 | 0/5 | 5/5 | Disappeared |
| 18 | CS-GlySerNH2 | 0.040 | 0/5 | 5/5 | Disappeared |
| 20 | CS-GlySerNH2 | 0.045 | 0/5 | 5/5 | Disappeared |
| 20 | CS-GlySerNH2 | 0.048 | 0/5 | 5/5 | Disappeared |
| 18 | CS-GlySerNH2 | 0.050 | 0/5 | 5/5 | Disappeared |
| 21 | CS-GlySerNHMe | 0.030 | 1/5 | 5/5 | Disappeared |
| 21 | CS-GlySerNHMe | 0.035 | 0/5 | 5/5 | Disappeared |
| 21 | CS-GlySerNHMe | 0.045 | 0/5 | 5/5 | Disappeared |
| 21 | CS-GlySerNHMe | 0.050 | 0/5 | 5/5 | Disappeared |
| 22 | CS-GlySerNMe2 | 0.030 | 1/5 | 5/5 | Disappeared |
| 22 | CS-GlySerNMe2 | 0.035 | 0/5 | 5/5 | Disappeared |
| 22 | CS-GlySerNMe2 | 0.045 | 1/5 | 5/5 | Disappeared |
| 23 | CS-GlyHomoSerEt | 0.019 | 0/5 | 5/5 | Disappeared |
| Comp. Ex. A | Seprafilm | — | 5/5 | 5/5 | Disappeared |
| Comp. Ex. B | CS | — | 5/5 | 5/5 | Disappeared |
| Comp. Ex. C | CS-NC2N | 0.030 | 0/5 | 5/5 | Remained |

As clear from the results in Table 3, commercial Seprafilm (Comparative Example A) and chondroitin sulfate sodium (CS) that was the uncrosslinked raw material (Comparative Example B) were disintegrated in the adhesion models but did not exhibit any antiadhesive effects.

On the other hand, the crosslinked CS products prepared with the inventive diamine linker having a biodegradable site showed significant antiadhesive effects and were disintegrated quickly after a prescribed period, and were thus demonstrated to be highly useful as adhesion preventing materials.

While CS-NC2N crosslinked with ethane-1,2-diamine.dihydrochloride having no biodegradable sites (Comparative Example C) exhibited significant antiadhesive effects, the test substance remained even after the laps of the prescribed period.

Based on the above results, it has been confirmed that the inventive diamine crosslinking agents for acidic polysaccharides are disintegrated in an appropriate time and the crosslinked acidic polysaccharides of the invention obtained using such crosslinking agents attain high antiadhesive performance and quick disintegration performance at the same time.

Example 43

Synthesis of 2-aminoethyl 2-(2-aminoacetamido)acetate (GlyGlyC2N).dihydrochloride (Compound 55)

Compound 55 was synthesized in the following manner

[Chem. 23]

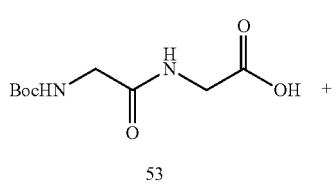

53

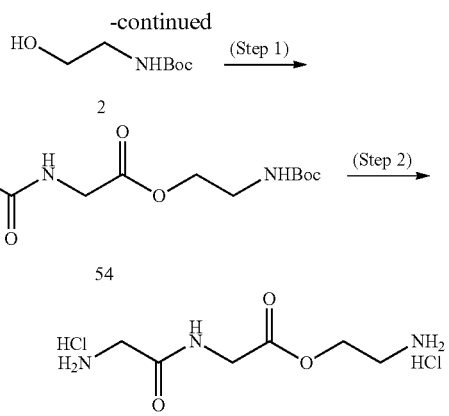

Compound 53 was purchased from Chem-Impex International, Inc.

(Step 1)

In substantially the same manner as in Example 1 (Step 1) except that Boc-glycine (Compound 1) used in Example 1 (Step 1) was replaced by Compound 53, Compound 54 (2.50 g, 6.65 mmol) was obtained from Compound 53 (2.01 g, 8.63 mmol) and Compound 2 (1.39 g, 8.61 mmol), as a white solid (yield 77%).

$^1$H-NMR (500 MHz, CDCl$_3$, δ) 1.44-1.46 (18H, s, Bocx 2), 3.40-3.41 (2H, m, CH2NHBoc), 3.85 (2H, d, J=6 Hz, BocNHCH2), 4.07 (2H, d, J=5 Hz, NHCH2COO), 4.12 (2H, t, J=5 Hz, COOCH2), 4.92 (1H, brs, NHBoc), 5.21 (1H, brs, BocNH), 6.70 (1H, brs, CONH)

ESI-MS: Calcd for C16H29N3O7 [M+NH4]+, 393.2; found 393.2.

(Step 2)

In substantially the same manner as in Example 6 (Step 2) except that Compound 19 used in Example 6 (Step 2) was replaced by Compound 54, the title Compound 55 (692 mg, 2.79 mmol) was obtained from Compound 54 (1.05 g, 2.79 mmol), as a white solid (yield 100%).

¹H-NMR (500 MHz, DMSO-d6, δ) 3.08 (2H, d, J=5 Hz, COOC<u>H2</u>), 3.64 (2H, s, NH3<u>CH2</u>), 4.05 (2H, d, J=7 Hz, CONH<u>CH2</u>), 4.30 (2H, t, J=5 Hz, <u>CH2</u>NH3), 8.37 (6H, brs, NH3×2), 9.07 (1H, t, J=7 Hz, CO<u>NH</u>)

ESI-MS: Calcd for C6H13N3O3 [M+H]+, 176.1; found 176.2.

Example 44

Synthesis of 2-(2-aminoethoxy)ethyl 2-aminoacetate (GlyC2OC2N).dihydrochloride (Compound 58)

Compound 58 was synthesized in the following manner.

[Chem. 24]

Compound 56 was synthesized by the method described in Biochemical and Biophysical Research Communications 374 (2008) 419-423.

(Step 1)

In substantially the same manner as in Example 1 (Step 1) except that Boc-ethanolamine (Compound 2) used in Example 1 (Step 1) was replaced by Compound 56, Compound 57 (4.14 g, 11.4 mmol) was obtained from Compound 1 (2.01 g, 11.4 mmol) and Compound 56 (2.36 g, 11.5 mmol), as a colorless transparent viscous liquid (yield 100%).

¹H-NMR (500 MHz, CDCl₃, δ) 1.45 (18H, m, <u>Boc</u>×2), 3.31-3.32 (2H, m, <u>CH2</u>NHBoc), 3.54 (2H, t, J=5 Hz, <u>CH2</u>CH2NHBoc), 3.66-3.69 (2H, m, <u>CH2</u>), 3.94 (2H, d, J=6 Hz, BocNH<u>CH2</u>), 4.28-4.32 (2H, m, <u>CH2</u>), 4.97-5.01 (2H, m, <u>NH</u>×2)

ESI-MS: Calcd for C16H30N2O7 [M+H]+, 363.2; found 363.2.

(Step 2)

In substantially the same manner as in Example 6 (Step 2) except that Compound 19 used in Example 6 (Step 2) was replaced by Compound 57, the title Compound 58 (654 mg, 2.78 mmol) was obtained from Compound 57 (1.01 g, 2.78 mmol), as a white viscous semisolid (yield 100%).

¹H-NMR (500 MHz, DMSO-d6, δ) 2.94-2.95 (2H, m, <u>CH2</u>NH3), 3.61-3.70 (4H, m, <u>CH2,CH2</u>CH2NH3), 3.81 (2H, brs, NH3<u>CH2</u>), 4.30-4.31 (2H, m, <u>CH2</u>), 8.27 (3H, brs, CH2<u>NH3</u>), 8.65 (3H, brs, <u>NH3</u>CH2)

ESI-MS: Calcd for C6H14N2O3 [M+H]+, 163.1; found 163.1.

Example 45

Synthesis of 2-((2-aminoethyl)amino)ethyl 2-aminoacetate (GlyC2NC2N).trihydrochloride (Compound 61)

Compound 61 was synthesized in the following manner

[Chem. 25]

Compound 59 was synthesized by the method described in Journal of Applied Polymer Science, 121 (2), (2011) 666-674.

(Step 1)

In substantially the same manner as in Example 1 (Step 1) except that Boc-ethanolamine (Compound 2) used in Example 1 (Step 1) was replaced by Compound 59, Compound 60 (3.95 g, 8.56 mmol) was obtained from Compound 1 (1.50 g, 8.56 mmol) and Compound 59 (2.61 g, 8.57 mmol), as a colorless transparent viscous liquid (yield 100%).

¹H-NMR (500 MHz, CDCl₃, δ) 1.43-1.45 (27H, m, <u>Boc</u>×3), 3.27-3.35 (4H, m, <u>CH2</u>NHBoc, <u>CH2</u>CH2NHBoc), 3.47 (2H, brs, <u>CH2</u>), 3.92 (2H, brs, BocNH<u>CH2</u>), 4.24-4.28 (2H, m, <u>CH2</u>), 4.66-4.99 (1H, m, <u>NH</u>Boc), 5.22-5.30 (1H, m, Boc<u>NH</u>)

ESI-MS: Calcd for C21H39N3O8 [M+H]+, 462.3; found 462.3.

(Step 2)

In substantially the same manner as in Example 6 (Step 2) except that Compound 19 used in Example 6 (Step 2) was replaced by Compound 60, title Compound 61 (1.07 g, 3.97 mmol) was obtained from Compound 60 (1.83 g, 3.97 mmol), as a white solid (yield 100%).

¹H-NMR (500 MHz, DMSO-d6, δ) 3.26-3.33 (6H, m, <u>CH2</u>×3), 3.91 (2H, s, H3N<u>CH2</u>), 4.49 (2H, t, J=5 Hz, <u>CH2</u>), 8.64-10.05 (8H, m, <u>NH3</u>×2, <u>NH2</u>)

ESI-MS: Calcd for C6H15N3O2 [M+H]+, 162.1; found 162.2.

Example 46

Synthesis of (S)-2-aminoethyl 2-amino-4-methyl-pentanoate (LeuC2N).dihydrochloride (Compound 64)

Compound 64 was synthesized in the following manner

[Chem. 26]

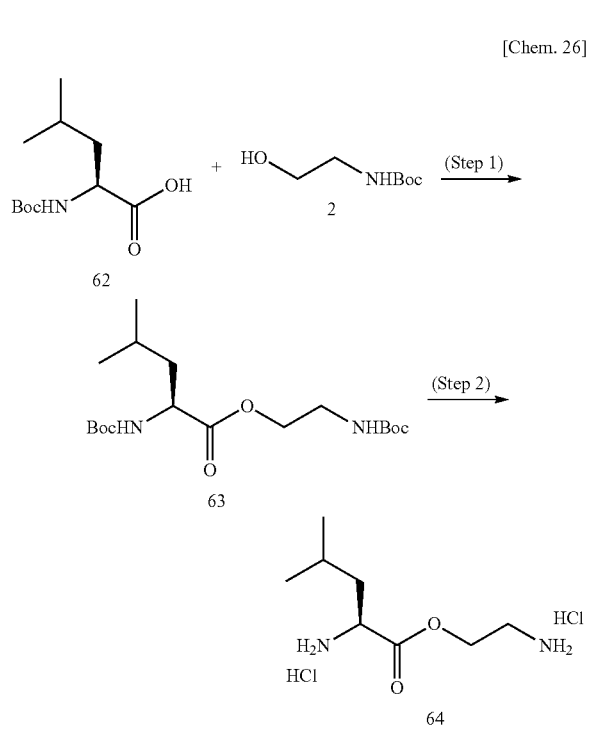

Compound 62 was purchased from Tokyo Chemical Industry Co., Ltd.

(Step 1)

In substantially the same manner as in Example 1 (Step 1) except that Boc-glycine (Compound 1) used in Example 1 (Step 1) was replaced by Compound 62, Compound 63 (4.32 g, 11.5 mmol) was obtained from monohydrate of Compound 62 (3.10 g, 12.4 mmol) and Compound 2 (2.00 g, 12.4 mmol), as a white solid (yield 93%).

$^1$H-NMR (500 MHz, CDCl$_3$, 55° C., δ) 0.95 (3H, s), 0.96 (3H, s), 1.45 (18H, s), 1.50 (1H, m), 1.59 (1H, m), 1.70 (1H, m), 3.41 (2H, m), 4.16-4.27 (3H, m), 4.86-4.93 (2H, m)

ESI-MS: Calcd for C18H34N2O6 [M+H]+, 375.2; found 375.4.

(Step 2)

In substantially the same manner as in Example 6 (Step 2) except that Compound 19 used in Example 6 (Step 2) was replaced by Compound 63, the title Compound 64 (668 mg, 2.70 mmol) was obtained from Compound 63 (1.01 g, 2.70 mmol), as a white solid (yield 100%).

$^1$H-NMR (500 MHz, DMSO-d6, δ) 0.90 (6H, dd, J=3 Hz, 7 Hz, CH3×2), 1.66-1.83 (3H, m, CH(CH3)2, CHCH2CH), 3.13 (2H, t, J=5 Hz, OCH2), 3.98 (1H, t, J=7 Hz, NH2CH), 4.31-4.43 (2H, m, CH2NH3), 8.63 (6H, brs, NH3×2)

ESI-MS: Calcd for C8H18N2O2 [M+H]+, 175.1; found 175.3.

Example 47

Synthesis of (S)-2-aminoethyl 2-amino-3-phenyl-propanoate (PheC2N).dihydrochloride (Compound 67)

Compound 67 was synthesized in the following manner.

[Chem. 27]

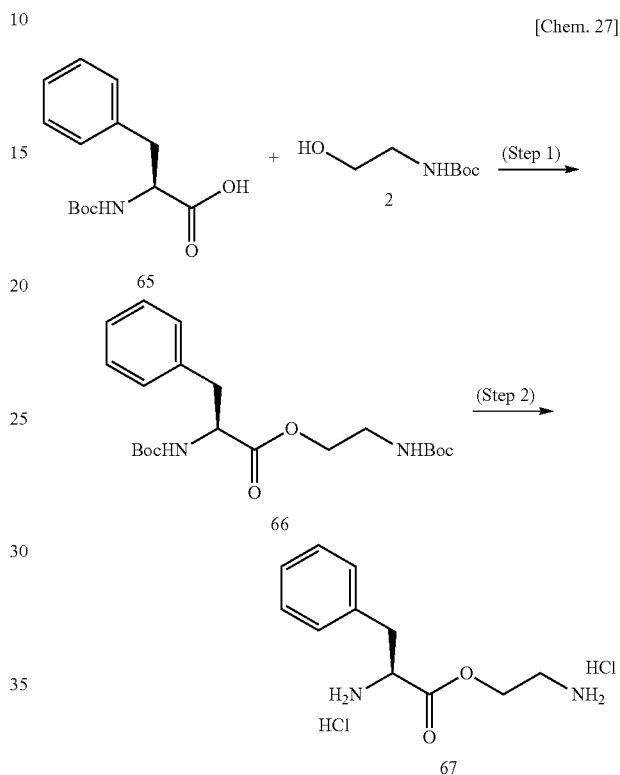

Compound 65 was purchased from Tokyo Chemical Industry Co., Ltd.

(Step 1)

In substantially the same manner as in Example 1 (Step 1) except that Boc-glycine (Compound 1) used in Example 1 (Step 1) was replaced by Compound 65, Compound 66 (4.65 g, 11.4 mmol) was obtained from Compound 65 (3.29 g, 12.4 mmol) and Compound 2 (2.01 g, 12.5 mmol), as a white solid (yield 92%).

$^1$H-NMR (500 MHz, CDCl$_3$, 55° C., δ) 1.43 (9H, s), 1.45 (9H, s), 3.06 (2H, m), 3.29 (2H, m), 4.14 (2H, m), 4.54 (1H, m), 4.64 (1H, s), 4.99 (1H, d, J=7 Hz), 7.17 (2H, m), 7.24-7.33 (3H, m)

ESI-MS: Calcd for C21H32N2O6 [M+H]+, 409.2; found 409.4.

(Step 2)

In substantially the same manner as in Example 6 (Step 2) except that Compound 19 used in Example 6 (Step 2) was replaced by Compound 66, the title Compound 67 (695 mg, 2.47 mmol) was obtained from Compound 66 (1.03 g, 2.53 mmol), as a white solid (yield 98%).

$^1$H-NMR (500 MHz, DMSO-d6, δ) 3.05-3.13 (2H, m, OCH2), 3.18-3.26 (2H, m, CH2Ph), 4.25-4.39 (3H, m, NH3CH, CH2NH3), 7.26-7.36 (5H, Ph), 8.66 (6H, brs, NH3×2)

ESI-MS: Calcd for C11H16N2O2 [M+H]+, 209.1; found 209.3.

Example 48

Synthesis of (S)-2-aminoethyl 2-amino-3-(1H-indol-3-yl)propanoate (TrpC2N).dihydrochloride (Compound 70)

Compound 70 was synthesized in the following manner.

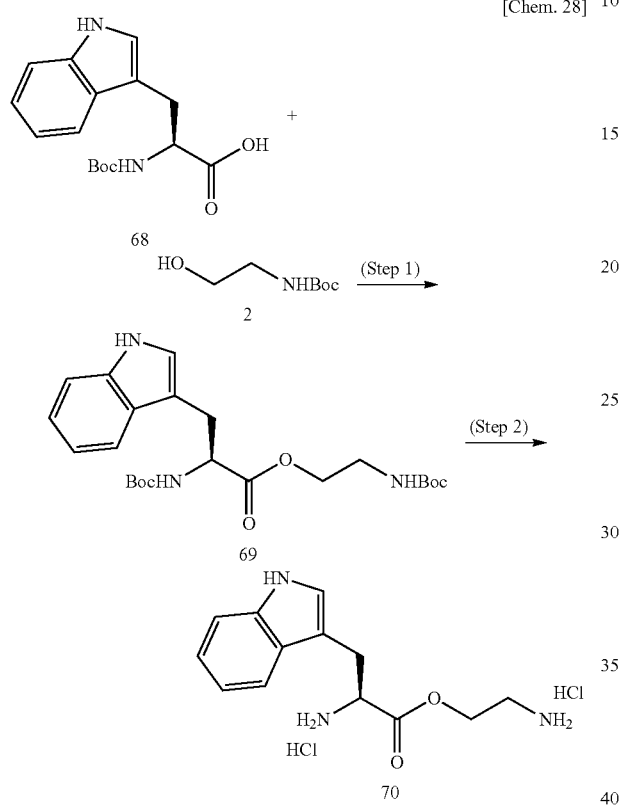

[Chem. 28]

Compound 68 was purchased from Tokyo Chemical Industry Co., Ltd.

(Step 1)

In substantially the same manner as in Example 1 (Step 1) except that Boc-glycine (Compound 1) used in Example 1 (Step 1) was replaced by Compound 68, Compound 69 (4.61 g, 10.3 mmol) was obtained from Compound 68 (3.77 g, 12.4 mmol) and Compound 2 (2.00 g, 12.4 mmol), as a white solid (yield 83%).

$^1$H-NMR (500 MHz, CDCl$_3$, 55° C., δ) 1.43 (9H, s), 1.44 (9H, s), 3.26 (4H, m) 4.10 (2H, m), 4.61 (2H, m), 5.07 (1H, d, J=7 Hz), 7.04 (1H, d, J=2 Hz), 7.14 (1H, m), 7.21 (1H, m), 7.37 (1H, d, J=8 Hz), 7.59 (1H, d, J=8 Hz), 8.09 (1H, s)

ESI-MS: Calcd for C23H33N3O6 [M+H]+, 448.2; found 448.4.

(Step 2)

In substantially the same manner as in Example 6 (Step 2) except that Compound 19 used in Example 6 (Step 2) was replaced by Compound 69, the title Compound 70 (725 mg, 2.26 mmol) was obtained from Compound 69 (1.01 g, 2.26 mmol), as a white solid (yield 100%).

$^1$H-NMR (500 MHz, DMSO-d6, δ) 3.05-3.12 (2H, m, OCH2), 3.33-3.40 (2H, m, CH2CH), 4.21-4.37 (3H, m, CH, CH2NH3), 7.02 (1H, dt, J=8 Hz, 1 Hz, Ph-H), 7.10 (1H, dt, J=8 Hz, 1 Hz, Ph-H), 7.29 (1H, d, J=3 Hz, HC=C), 7.38 (1H, d, J=8 Hz, Ph-H), 7.58 (1H, d, J=8 Hz, Ph-H), 8.58 (6H, brs, NH3×2), 11.09 (1H, d, J=2 Hz, NH)

ESI-MS: Calcd for C13H17N3O2 [M+H]+, 248.1; found 248.3.

Example 49

Synthesis of (S)-(2R,3S)-3-amino-4-(ethylamino)-4-oxobutan-2-yl 2-aminopropanoate (AlaThrNHEt).dihydrochloride (Compound 74)

Compound 74 was synthesized in the following manner.

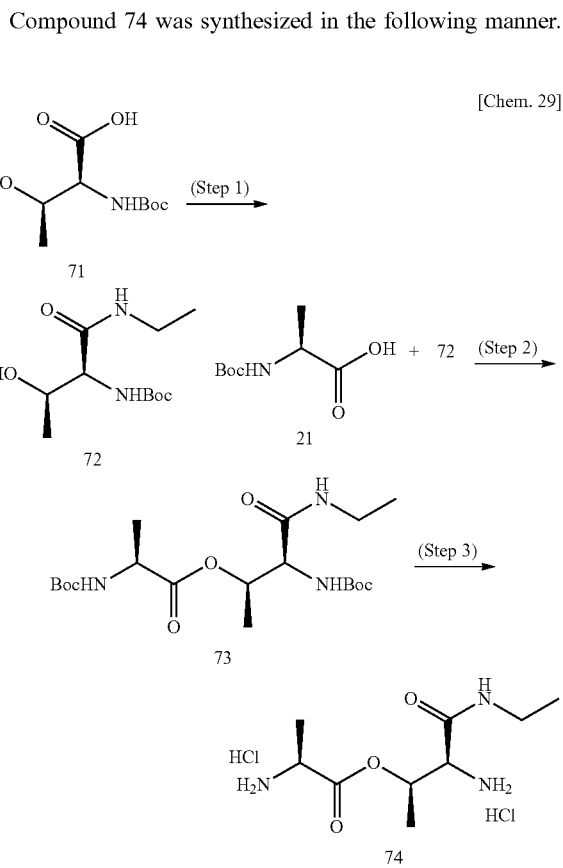

[Chem. 29]

Compound 71 was purchased from Sigma-Aldrich.

(Steps 1 and 2)

Boc-threonine (Compound 71) (3.00 g, 13.7 mmol) was dissolved into tetrahydrofuran (THF)/1.83 N aqueous sodium hydroxide solution=3/1 (30 mL). At room temperature, ethylamine hydrochloride (1.12 g, 13.7 mmol) and 4-(4,6-dimethoxy-1,3,5-triazin-2-yl)-4-methylmorpholinium chloride.N hydrate (DMT-MM) (6.44 g, 23.3 mmol) were added. Further, methanol/water=1/4 (37.5 mL) was added. The mixture was stirred at room temperature overnight. The reaction liquid was concentrated, and 0.5 N hydrochloric acid was added. Extraction was performed with ethyl acetate. The organic phase was washed sequentially with saturated sodium bicarbonate water and saturated saline, dried with sodium sulfate, and filtered. The solvent was distilled off under reduced pressure, and the residue was dried. Thus, Compound 72 (3.39 g, crude) was obtained as a white viscous semisolid.

Subsequently, Compound 21 (2.59 g, 13.7 mmol), Compound 72 (3.39 g, crude) and triethylamine (2.10 mL, 15.1 mmol) were reacted in substantially the same manner as in Example 1 (Step 1) except that Boc-glycine (Compound 1)

used in Example 1 (Step 1) was replaced by Boc-alanine (Compound 21), and Boc-ethanolamine (Compound 2) was replaced by Compound 72. In this manner, Compound 73 (3.72 g, 8.92 mmol) was obtained as a white amorphous solid (yield in 2 steps: 65%).

$^1$H-NMR (500 MHz, CDCl$_3$, δ) 1.16 (3H, t, J=8 Hz, CH2C$\underline{H}$3), 1.24 (3H, d, J=7 Hz, OCHC$\underline{H}$3), 1.35 (3H, d, J=7 Hz, BocNHCHC$\underline{H}$3), 1.42-1.47 (18H, m, Boc×2), 3.26-3.38 (2H, m, C$\underline{H}$2CH3), 4.17-4.25 (2H, m, BocNHC$\underline{H}$, C$\underline{H}$NHBoc), 4.99-5.00 (1H, m, BocN$\underline{H}$), 5.29 (1H, brs, OC$\underline{H}$), 5.50 (1H, brs, N$\underline{H}$Boc), 6.17-7.00 (1H, m, CON$\underline{H}$)

ESI-MS Calcd for C19H35N3O7 [M+H]+, 418.3; found 418.3.

(Step 3)

In substantially the same manner as in Example 6 (Step 2) except that Compound 19 used in Example 6 (Step 2) was replaced by Compound 73, the title Compound 74 (723 mg, 2.49 mmol) was obtained from Compound 73 (1.04 g, 2.49 mmol), as a white solid (yield 100%).

$^1$H-NMR (500 MHz, DMSO-d6, δ) 1.06 (3H, t, J=7 Hz, CH2C$\underline{H}$3), 1.29 (3H, d, J=7 Hz, OCHC$\underline{H}$3), 1.45 (3H, d, J=7 Hz, H3NCHC$\underline{H}$3), 3.08-3.22 (2H, m, C$\underline{H}$2CH3), 3.98 (1H, d, J=6 Hz, C$\underline{H}$NH3), 4.08-4.09 (1H, m, H3NC$\underline{H}$), 5.16 (1H, dq, J=7 Hz, 7 Hz, OC$\underline{H}$), 8.74-8.79 (6H, m, N$\underline{H}$3×2), 9.04 (1H, t, J=6 Hz, CON$\underline{H}$).

ESI-MS: Calcd for C9H19N3O3 [M+H]+, 218.2; found 218.2.

Example 50

Synthesis of (S)-2-aminoethyl 2-amino-4-(methylthio)butanoate (MetC2N).dihydrochloride (Compound 77)

Compound 77 was synthesized in the following manner.

[Chem. 30]

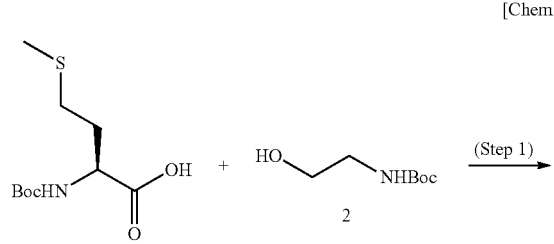

75

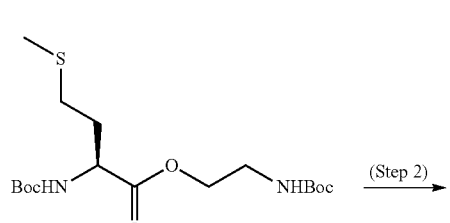

76

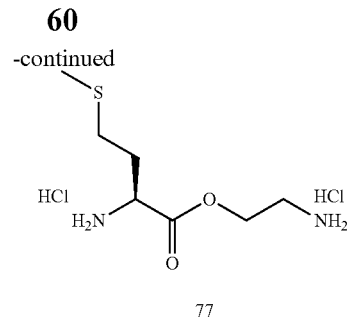

77

Compound 75 was purchased from Tokyo Chemical Industry Co., Ltd.

(Step 1)

In substantially the same manner as in Example 1 (Step 1) except that Boc-glycine (Compound 1) used in Example 1 (Step 1) was replaced by Compound 75, Compound 76 (3.06 g, 7.81 mmol) was obtained from Compound 75 (2.01 g, 8.06 mmol) and Compound 2 (1.30 g, 8.06 mmol), as a white solid (yield 97%).

$^1$H-NMR (500 MHz, CDCl$_3$, δ) 1.45 (18H, s, $\underline{Boc}$×2), 1.92-1.99 (1H, m, SCH2C$\underline{H}$), 2.11-2.16 (4H, m, SC$\underline{H}$3, SCH2C$\underline{H}$), 2.55 (2H, t, J=8 Hz, SC$\underline{H}$2), 3.41-3.42 (2H, m, C$\underline{H}$2NH), 4.19-4.25 (2H, m, OC$\underline{H}$2), 4.38-4.39 (1H, m, NHC$\underline{H}$), 4.99 (1H, brs, N$\underline{H}$Boc), 5.21-5.23 (1H, m, BocN$\underline{H}$).

ESI-MS: Calcd for C17H32N2O6S [M+H]+, 393.2; found 393.5.

(Step 2)

In substantially the same manner as in Example 6 (Step 2) except that Compound 19 used in Example 6 (Step 2) was replaced by Compound 76, the title Compound 77 (601 mg, 2.26 mmol) was obtained from Compound 76 (1.00 g, 2.56 mmol) as a white viscous semisolid (yield 89%).

$^1$H-NMR (500 MHz, DMSO-d6, δ) 2.07 (3H, s, $\underline{Me}$), 2.12-2.20 (2H, m, SCH2C$\underline{H}$2), 2.58-2.71 (2H, m, SC$\underline{H}$2), 3.14 (2H, d, J=5 Hz, C$\underline{H}$2NH3), 4.13 (1H, brs, NH3C$\underline{H}$), 4.33-4.44 (2H, m, C$\underline{H}$2CH2NH3), 8.51 (3H, brs, N$\underline{H}$3), 8.93 (3H, brs, N$\underline{H}$3)

ESI-MS: Calcd for C7H16N2O2S [M+H]+, 193.1; found 193.2.

Example 51

Synthesis of 2-aminoethyl 3-amino-2-fluoropropanoate (βAla(F)C2N).dihydrochloride (Compound 81)

Compound 81 was synthesized in the following manner.

[Chem. 31]

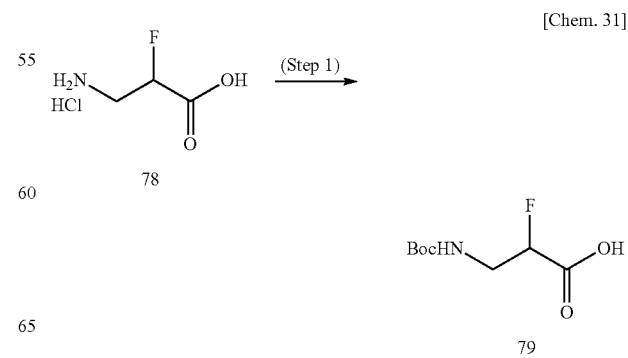

78

79

-continued

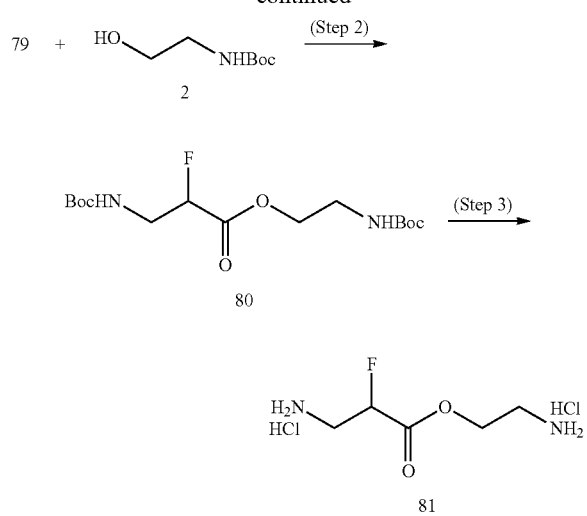

Example 52

Synthesis of 2-aminoethyl 2-amino-2-methylpropanoate ((Me)AlaC2N).dihydrochloride (Compound 84)

Compound 84 was synthesized in the following manner

[Chem. 32]

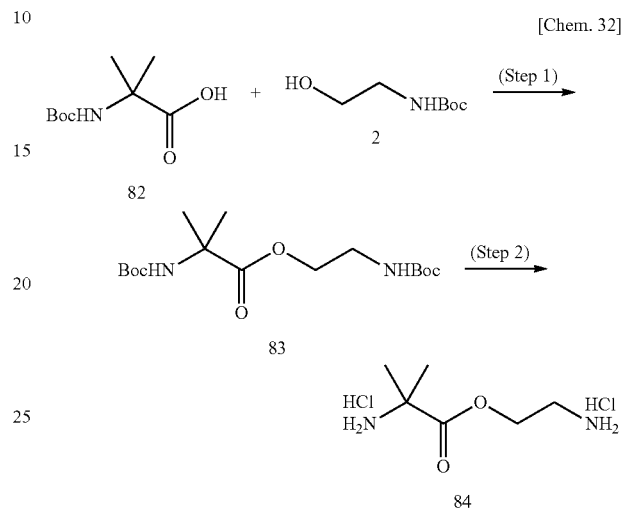

Compound 78 was purchased from Tokyo Chemical Industry Co., Ltd.

(Steps 1 and 2)

Compound 78 (1.30 g, 9.07 mmol) was dissolved into tetrahydrofuran (THF) (26 mL) and 1 N aqueous sodium hydroxide solution (18.1 mL) While performing cooling with ice, Boc₂O (2.08 g, 9.52 mmol) and water (7 mL) were added. The mixture was stirred at room temperature overnight. The reaction liquid was vacuum concentrated. The residue was brought to pH 1 by the addition of 1 N hydrochloric acid, and extraction was performed with chloroform (150 mL×4). The organic phase was dried with sodium sulfate, and was filtered. The filtrate was vacuum concentrated. The residue was vacuum dried at room temperature. Thus, Compound 79 (2.04 g, crude) was obtained as a colorless transparent viscous liquid.

Subsequently, in substantially the same manner as in Example 1 (Step 1) except that Boc-glycine (Compound 1) used in Example 1 (Step 1) was replaced by Compound 79, Compound 80 (2.21 g, 6.30 mmol) was obtained from Compound 79 (2.04 g, crude) and Compound 2 (1.46 g, 9.06 mmol), as a white solid (yield in 2 steps: 70%).

¹H-NMR (500 MHz, CDCl₃, δ) 1.44-1.45 (18H, m, Boc×2), 3.43 (2H, brs, C$\underline{H}$2NHBoc), 3.54-3.63 (1H, m, BocNHC$\underline{H}$), 3.81-3.85 (1H, m, BocNHC$\underline{H}$), 4.13-4.17 (1H, m, OC$\underline{H}$), 4.36-4.37 (1H, m, OC$\underline{H}$), 4.92-5.03 (2H, m, C$\underline{H}$F, BocN$\underline{H}$), 5.44 (1H, brs, N$\underline{H}$Boc)

ESI-MS: Calcd for C15H27FN2O6 [M+H]+, 351.2; found 351.2.

(Step 3)

In substantially the same manner as in Example 6 (Step 2) except that Compound 19 used in Example 6 (Step 2) was replaced by Compound 80, the title Compound 81 (660 mg, 2.94 mmol) was obtained from Compound 80 (1.03 g, 2.94 mmol), as a white solid (yield 100%).

¹H-NMR (500 MHz, DMSO-d6, δ) 3.10-3.18 (2H, m, C$\underline{H}$2NH3), 3.37-3.51 (2H, m, NH3C$\underline{H}$2), 4.35-4.44 (2H, m, OC$\underline{H}$2), 5.50-5.62 (1H, m, C$\underline{H}$F), 8.46-8.64 (6H, m, N$\underline{H}$3×2)

ESI-MS: Calcd for C5H11FN2O2 [M+H]+, 151.1; found 151.1.

Compound 82 was purchased from Tokyo Chemical Industry Co., Ltd.

(Step 1)

In substantially the same manner as in Example 1 (Step 1) except that Boc-glycine (Compound 1) used in Example 1 (Step 1) was replaced by Compound 82, and triethylamine (2.50 mL, 17.9 mmol) was further added. Compound 83 (2.50 g, 7.22 mmol) was obtained from Compound 82 (3.00 g, 14.8 mmol) and Compound 2 (2.87 g, 17.8 mmol), as a colorless transparent viscous liquid (yield 49%).

¹H-NMR (500 MHz, CDCl₃, δ) 1.43-1.45 (18H, m, Boc×2), 1.48 (6H, s, C$\underline{H}$3×2), 3.42 (2H, d, J=5 Jz, C$\underline{H}$2NHBoc), 4.23 (2H, t, J=5 Hz, OC$\underline{H}$2), 4.94 (1H, brs, BocN$\underline{H}$), 5.16 (1H, brs, N$\underline{H}$Boc)

ESI-MS: Calcd for C16H30N2O6 [M+NH4]+, 347.2; found 347.3.

(Step 2)

In substantially the same manner as in Example 6 (Step 2) except that Compound 19 used in Example 6 (Step 2) was replaced by Compound 83, the title Compound 84 (587 mg, 2.68 mmol) was obtained from Compound 83 (939 mg, 2.71 mmol), as a white solid (yield 99%).

¹H-NMR (500 MHz, DMSO-d6, δ) 1.53 (6H, s, C$\underline{H}$3×2), 3.15 (2H, t, J=5 Hz, C$\underline{H}$2), 4.34-4.36 (2H, m, C$\underline{H}$2), 8.29-8.77 (6H, brs, N$\underline{H}$3×2)

ESI-MS: Calcd for C6H14N2O2 [M+H]+, 147.1; found 147.1.

Example 53

Preparation of Chondroitin Sulfate Crosslinked with Compound 37 (CS-GlyPhC2N)

In substantially the same manner as in Example 17 (Method A) except that Compound 7 used in Example 17 (Method A) was replaced by Compound 37 (synthesized in Example 12), the equivalent of Compound 37 was (0.030, 0.040 or 0.050 eq), and the amount of CS was changed to 0.80 g, Crosslinked CS products (CS-GlyPhC2N) were obtained as a white powder (in each case approximately 0.65 g).

Example 54

Preparation of Chondroitin Sulfate Crosslinked with Compound 42 (CS-GlyLacC2N)

In substantially the same manner as in Example 17 (Method A) except that Compound 7 used in Example 17 (Method A) was replaced by Compound 42 (synthesized in Example 13), the equivalent of Compound 42 was (0.040, 0.050 or 0.060 eq), and the amount of CS was changed to 0.80 g, Crosslinked CS products (CS-GlyLacC2N) were obtained as a white powder (in each case approximately 0.78 g).

Example 55

Preparation of Chondroitin Sulfate Crosslinked with Compound 52 (CS-OctHomoSerEt)

In substantially the same manner as in Example 17 (Method A) except that Compound 7 used in Example 17 (Method A) was replaced by Compound 52 (synthesized in Example 16), the equivalent of Compound 52 was (0.060, 0.080 or 0.100 eq), and the amount of CS was changed to 0.80 g, Crosslinked CS products (CS-OctHomoSerEt) were obtained as a white powder (in each case approximately 0.62 g).

Example 56

Preparation of Chondroitin Sulfate Crosslinked with Compound 81 (CS-βAla(F)C2N)

In substantially the same manner as in Example 17 (Method A) except that Compound 7 used in Example 17 (Method A) was replaced by Compound 81 (synthesized in Example 51), the equivalent of Compound 81 was (0.030, 0.040 or 0.050 eq), and the amount of CS was changed to 0.80 g, Crosslinked CS products (CS-βAla(F)C2N) were obtained as a white powder (in each case approximately 0.69 g).

Example 57

Preparation of Chondroitin Sulfate Crosslinked with Compound 84 (CS-(Me)AlaC2N)

In substantially the same manner as in Example 17 (Method A) except that Compound 7 used in Example 17 (Method A) was replaced by Compound 84 (synthesized in Example 52), the equivalent of Compound 84 was (0.100 or 0.300 eq), and the amount of CS was changed to 0.80 g, Crosslinked CS products (CS-(Me)AlaC2N) were obtained as a white powder (in each case approximately 0.61 g).

All publications, patent applications and technical standards mentioned in the present specification are herein incorporated by reference to the same extent as if each individual publication, patent application or technical standard was specifically and individually indicated to be incorporated by reference.

The invention claimed is:

1. A method for preventing tissue adhesion, the method comprising a step of administering a crosslinked acidic polysaccharide to a surgical area of an individual,
   wherein the crosslinked acidic polysaccharide is obtained by forming crosslinks by amide bonding between primary amino groups in a diamine crosslinking agent and carboxyl groups in an acidic polysaccharide;
   wherein the acidic polysaccharide is chondroitin sulfate;
   wherein the diamine crosslinking agent consists of diamine compounds having a primary amino group at both terminals and an ester or thioester bond; and
   wherein the ester or thioester bond is component of a linear chain connecting the two terminal amino groups.

2. The method for preventing adhesion according to claim 1, wherein the diamine crosslinking agent has the general formula (I) below:

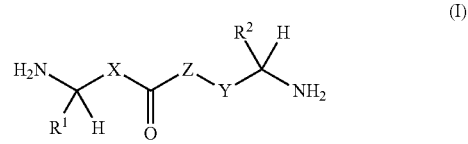

(I)

wherein the number of atoms in the linear chain between the primary amino groups at both terminals is 5 to 12, X and Y are each independently a single bond, a substituted or unsubstituted alkanediyl group, a substituted or unsubstituted alkenylene group, or a substituted or unsubstituted alkynylene group, with the proviso that X and Y are not single bonds at the same time;

Z is an oxygen atom or a sulfur atom;

$R^1$ and $R^2$ are each independently a hydrogen atom, a —$CONR^3R^4$ group, a —$COOR^5$ group, a substituted or unsubstituted alkyl group, a substituted or unsubstituted alkenyl group, or a substituted or unsubstituted alkynyl group, any —$CH_2$— in X or Y, if present, contains optionally substitution of one or more groups selected from the group consisting of an amide group (—CONH—), an ester group (—C(=O)—O—), an ether group (—O—), an imino group (—NH—) and a phenylene group, wherein the ester group, the amide group, the ether group or the imino group present in X or Y is not directly adjacent to —CO—Z— in the formula (I), any —$CH_2$— in $R^1$ or $R^2$, if present, contains optionally substitution of one or more groups selected from the group consisting of >C=O, —CONH—, arylene, —O—, —$NR^6$— and —S—;

the substituent in each of X and Y is selected from the group consisting of an hydroxyl group, an alkyl group having 1 to 6 carbon atoms, a phenyl group, an indolyl group, a diazolyl group, a —$(CH_2)_n$—NHMe group, a —$(CH_2)_n$—$NMe_2$ group, a —$(CH_2)_n$—$CONR^3R^4$ group, a —$(CH_2)_n$—$COOR^5$ group, a —S-Me group, —SH group, 4-hydroxyphenyl group, a halogen atom, a nitro group, and a nitrile group, wherein n independently at each occurrence is an integer of 0 to 4;

the substituent in $R^1$ and $R^2$ is selected from the group consisting of an hydroxyl group, an alkyl group having 1 to 6 carbon atoms, a phenyl group, an indolyl group, a diazolyl group, a —$(CH_2)_n$—NHMe group, a —$(CH_2)_n$—$NM_2$ group, a —$(CH_2)_n$—$CONR^3R^4$ group, a —$(CH_2)_n$—$COOR^5$ group, a —S-Me group and a —SH group, wherein n is, independently, an integer of 0 to 4; and $R^3$, $R^4$, $R^5$ and $R^6$ are each, independently, a hydrogen atom or an alkyl group that contains optionally substitution of.

3. The method according to claim 2, wherein Z is an oxygen atom.

4. The method according to claim 3, wherein the number of atoms in the linear chain between the primary amino groups at both terminals is 5 to 8.

5. The method according to claim 3, wherein the number of atoms in the linear chain between the primary amino groups at both terminals is 5 or 6.

6. The method according to claim 2, wherein
$R^1$ is a hydrogen atom, or a substituted or unsubstituted alkyl group;
$R^2$ is a hydrogen atom, a —CONR$^3$R$^4$ group or a —COOR$^5$ group;
X is a single bond or an alkanediyl group which a contains optionally substitution of a halogen;
Y is a substituted or unsubstituted alkanediyl group;
the substituent(s) in $R^1$ is selected from the group consisting of a methyl group, a phenyl group, an indolyl group, a —COOR$^5$ group and a —S-Me group; and
the substituent(s) in Y is selected from the group consisting of a methyl group, a phenyl group and a —COOR$^5$ group.

7. The method according to claim 2, wherein
X is a single bond; Y is a >CR$^7$R$^8$ group; and
$R^7$ and $R^8$ are each independently a hydrogen atom, a hydroxyl group, an alkyl group having 1 to 6 carbon atom, a phenyl group, a 4-hydroxyphenyl group, an indolyl group, a diazolyl group, a —(CH$_2$)$_n$—NHMe group, a —(CH$_2$)$_n$—NMe$_2$ group, a —(CH$_2$)$_n$—CONR$^3$R$^4$ group, a —(CH$_2$)$_n$—COOR$^5$ group, a —SH group, a halogen atom, a nitro group or a nitrile group.

8. The method according to claim 7, wherein
$R^2$ is a —CONR$^3$R$^4$ group or a —COOR$^5$ group;
$R^7$ is a hydrogen atom; and
$R^8$ is a hydrogen atom or a methyl group.

9. The method according to claim 4, wherein at least one of X and Y contains substitution of a phenyl group, a 4-hydroxyphenyl group, a —CONR$^3$R$^4$ group, a —COOR$^5$ group, a halogen atom, a nitro group or a nitrile group.

10. The method according to claim 7, wherein $R^7$ and $R^8$ are each independently a hydrogen atom, a phenyl group, a 4-hydroxyphenyl group, a —CONR$^3$R$^4$ group, a —COOR$^5$ group, a halogen atom, a nitro group or a nitrile group.

11. The method according to claim 10, wherein $R^1$ is a hydrogen atom, a —(CH$_2$)$_2$—S—CH$_3$ group, a —(CH$_2$)$_{3\text{ or }4}$—NHMe group, a —(CH$_2$)$_{3\text{ or }4}$—NMe$_2$ group or a —(CH$_2$)$_{1\text{ or }2}$—COOR$^5$ group.

12. The method according to claim 11, wherein $R^2$ is a —CONR$^3$R$^4$ group or a —COOR$^5$ group, and $R^7$ and $R^8$ are hydrogen atoms.

13. The method according to claim 12, wherein $R^1$ is a hydrogen atom.

14. The method according to claim 10, wherein the diamine crosslinked agent has the general formula (II) below:

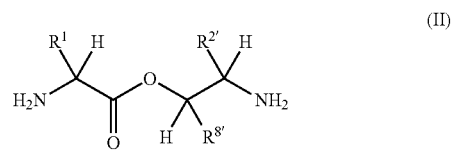

wherein $R^1$ is a hydrogen atom, a —CONR$^3$R$^4$ group, a —COOR$^5$ group, a substituted or unsubstituted alkyl group, a substituted or unsubstituted alkenyl group, or a substituted or unsubstituted alkynyl group;
$R^{2'}$ is a —CONR$^3$R$^4$ group or a —COOR$^5$ group;
any —CH$_2$— in $R^1$, if present, contains optionally substitution of one or more groups selected from the group consisting of a >C=O, an —CONH—, an arylene, an —O—, an —NR$^6$— and a —S—(with the proviso that when $R^5$ is a benzyl group, the —O— is excluded);
the substituent(s) in $R^1$ is selected from the group consisting of a hydroxyl group, an alkyl group having 1 to 6 carbon atom, an indolyl group, a diazolyl group, a —(CH$_2$)$_n$—NHMe group, a —(CH$_2$)$_n$—NMe$_2$ group, a —(CH$_2$)$_n$—CONR$^3$R$^4$ group, a —(CH$_2$)$_n$—COOR$^5$ group and a —SH group (with the proviso that when $R^{2'}$ is a —CONH$_2$ group, the —SH group is excluded) wherein n independently at each occurrence is an integer of 0 to 4;
$R^3$, $R^4$, $R^5$ and $R^6$ are each independently a hydrogen atom or an alkyl group that contains optionally substitution of a phenyl group; and
$R^{8'}$ is a hydrogen atom or a methyl group.

\* \* \* \* \*

UNITED STATES PATENT AND TRADEMARK OFFICE
CERTIFICATE OF CORRECTION

PATENT NO. : 10,294,195 B2
APPLICATION NO. : 15/115331
DATED : May 21, 2019
INVENTOR(S) : Sho Funayama et al.

Page 1 of 3

It is certified that error appears in the above-identified patent and that said Letters Patent is hereby corrected as shown below:

On the Title Page

Column 2, In item (56) References Cited, U.S. Patent Documents, Line 1, "Junin et al." should read -- Junino et al --.

Column 2, In item (56) References Cited, U.S. Patent Documents, Line 5, "5,642,363 A 6/1997 Smith" should read -- 6,642,363 B1 4/2003 Mooney et al. --.

In the Specification

At Column 2, Line number 5, "1141-56" should read -- H41-56 --.

At Column 2, Line numbers 60-67, in the diagram, "X" should read -- $X^-$ --, thereby appearing as:

5-exo-trig type .

At Column 6, Line number 2, "12," should read -- 12; --.

At Column 6, Line number 21, "(I)," should read -- (I); --.

At Column 7, Line number 2, "$CONR_3R_4$" should read -- $CONR^3R^4$ --.

At Column 8, Line number 61, "A1aC2MeN/NC2N" should read -- AlaC2MeN/NC2N --.

At Column 8, Line number 64, "A1aC2MeN/NC2N" should read -- AlaC2MeN/NC2N --.

At Column 9, Line number 5, "A1aC2Me2N" should read -- AlaC2Me2N --.

Signed and Sealed this
Third Day of September, 2019

Andrei Iancu
*Director of the United States Patent and Trademark Office*

CERTIFICATE OF CORRECTION (continued)
U.S. Pat. No. 10,294,195 B2

At Column 11, Line number 67, "12," should read -- 12; --.

At Column 12, Line numbers 14-15, "–C(=O)–O–)" should read -- (–C(=O) –O–) --.

At Column 12, Line number 19, "(I)," should read -- (I); --.

At Column 15, Line number 23, "CONR$_3$R$_4$" should read -- CONR$^3$R$^4$ --.

At Column 17, Line number 59, "–(CH$_2$)$_n$CONR$^3$R$^4$" should read -- –(CH$_2$)$_n$–CONR$^3$R$^4$ --.

At Column 22, Line number 16, "endometiosis" should read -- endometriosis --.

At Column 23, Line number 52, "C14H26N2O6[M+]+" should read -- C14H26N2O6[M+H]+ --.

At Column 25, Line number 66, "323.2," should read -- 323.2; --.

At Column 26, Line numbers 10-36, in [Chem. 10], "9" should read -- 13 --.

At Column 26, Line numbers 10-36, a line break should be inserted into the diagram between Compound 12 and Compound 1 of [Chem. 10].

At Column 26, Line number 40, "(30 mL)" should read -- (30 mL). --.

At Column 27, Line number 12, "Hz 12 Hz," should read -- Hz, 12 Hz, --.

At Column 28, Line number 14, "(1H, dd, 3 Hz 12 Hz, CH2)" should read -- (1H, dd, 3 Hz, 12 Hz, CH2) --.

At Column 28, Line number 27, "manner" should read -- manner. --.

At Column 28, Line numbers 28-50, Compound 18 of [Chem. 12] should be accurately depicted as:

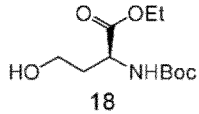

At Column 29, Line number 10, "C112" should read -- CH2 --.

At Column 30, Line number 15, "manner" should read -- manner. --.

At Column 32, Line number 44, "manner" should read -- manner. --.

At Column 33, Line number 63, "Compound 35)" should read -- (Compound 35) --.

At Column 34, Line numbers 31-65, a line break should be inserted between Compound 40 and Compound 2 of [Chem. 19].

CERTIFICATE OF CORRECTION (continued)
U.S. Pat. No. 10,294,195 B2

At Column 37, Line numbers 24-50, a line break should be inserted between Compound 46 and Compound 1 of [Chem. 21].

At Column 48, Line number 10, "100%)" should read -- 100%). --.

At Column 51, Line number 57, "manner" should read -- manner. --.

At Column 54, Line number 8, "manner" should read -- manner. --.

At Column 55, Line number 8, "manner" should read -- manner. --.

At Column 56, Line number 65, "(5H, Ph)" should read -- (5H, m, Ph) --.

At Column 58, Line numbers 15-45, a line break should be inserted between Compound 72 and Compound 21 of [Chem. 29].

At Column 59, Line number 26, "1H, in," should read -- 1H, m, --.

At Column 61, Line number 29, "(18.1 mL)" should read -- (18.1 mL). --.

At Column 62, Line number 7, "manner" should read -- manner. --.

At Column 62, Line number 42, "Jz" should read -- Hz --.

In the Claims

At Column 64, Claim number 2, Line number 57, "–SH group, 4-hydroxyphenyl group" should read -- a –SH group, a 4-hydroxyphenyl group --.

At Column 64, Claim number 2, Line number 64, "–(CH2)n–NM2 group" should read -- –(CH2)n–NMe2 group --.

At Column 65, Claim number 2, Line numbers 2-3, "optionally substitution of." should read -- optionally substitution of a phenyl group. --.

At Column 65, Claim number 6, Line number 17, "which a contains" should read -- which contains --.

At Column 66, Claim number 14, Line number 31, "–S–(with" should read -- –S– (with --.